US012759965B2

(12) United States Patent
Wampler et al.

(10) Patent No.: US 12,759,965 B2
(45) Date of Patent: Oct. 13, 2026

(54) SYNTHESIS OF PHEROMONE DERIVATIVES VIA Z-SELECTIVE OLEFIN METATHESIS

(71) Applicant: Provivi, Inc., Santa Monica, CA (US)

(72) Inventors: Keith M. Wampler, Santa Monica, CA (US); Richard L. Pederson, Santa Monica, CA (US)

(73) Assignee: Provivi, Inc., Santa Monica, CA (US)

( * ) Notice: Subject to any disclaimer, the term of this patent is extended or adjusted under 35 U.S.C. 154(b) by 884 days.

(21) Appl. No.: 17/988,238

(22) Filed: Nov. 16, 2022

(65) Prior Publication Data

US 2023/0095259 A1 Mar. 30, 2023

Related U.S. Application Data

(63) Continuation of application No. PCT/US2021/035257, filed on Jun. 1, 2021.

(Continued)

(51) Int. Cl.

*C07C 67/475* (2006.01)
*B01J 31/02* (2006.01)

(Continued)

(52) U.S. Cl.

CPC ......... *C07C 67/475* (2013.01); *B01J 31/0212* (2013.01); *B01J 31/181* (2013.01);

(Continued)

(58) Field of Classification Search

None

See application file for complete search history.

(56) References Cited

U.S. PATENT DOCUMENTS 6,533,960 B2 3/2003 Mimoun
6,921,735 B2 7/2005 Hoveyda et al.

(Continued)

FOREIGN PATENT DOCUMENTS

CN 103319704 A 9/2013
CN 110603240 A 12/2019

(Continued)

OTHER PUBLICATIONS

Chandrasekhar S., et al., "One pot conversion of carylic acids to aldehydes with DIBAL-H", Tetrahedron Letters vol. 39, Issue 8, Feb. 19, 1998, pp. 909-910, https://doi.org/10.1016/S0040-4039(97)10688-8.

(Continued)

*Primary Examiner* — Amy C Bonaparte

(74) *Attorney, Agent, or Firm* — Jacob M. Ward; Fernando Alberdi; Ward Law Office LLC

(57) ABSTRACT

Disclosed herein are methods for synthesizing fatty olefin metathesis products of high Z-isomeric purity from olefin feedstocks of low Z-isomeric purity. The methods include contacting a contacting an olefin metathesis reaction partner, such as acylated alkenol or an alkenal acetal, with an internal olefin in the presence of a Z-selective metathesis catalyst to form the fatty olefin metathesis product. In various embodiments, the fatty olefin metathesis products are insect pheromones. Pheromone compositions and methods of using them are also described.

24 Claims, 5 Drawing Sheets

Related U.S. Application Data

(60) Provisional application No. 63/032,932, filed on Jun. 1, 2020.

(51) Int. Cl.

| | |
|---|---|
| ***B01J 31/18*** | (2006.01) |
| ***B01J 31/22*** | (2006.01) |
| ***C07C 29/157*** | (2006.01) |
| ***C07F 15/00*** | (2006.01) |

(52) U.S. Cl.

CPC ....... *B01J 31/2213* (2013.01); *B01J 31/2226* (2013.01); *B01J 31/226* (2013.01); *B01J 31/2273* (2013.01); *B01J 31/2278* (2013.01); *C07C 29/157* (2013.01); *C07F 15/0046* (2013.01); *B01J 2231/543* (2013.01); *B01J 2531/64* (2013.01); *B01J 2531/821* (2013.01)

(56) References Cited

U.S. PATENT DOCUMENTS

| | | | | |
|---|---|---|---|---|
| 9,938,253 | B2 | 4/2018 | Hoveyda et al. | |
| 10,774,035 | B2 | 9/2020 | Johns et al. | |
| 10,857,350 | B2 | 12/2020 | Meadows | |
| 2002/0022741 | A1* | 2/2002 | Pederson | C07C 6/04 502/200 |
| 2009/0264672 | A1* | 10/2009 | Abraham | B01J 31/2278 562/595 |
| 2015/0025212 | A1 | 1/2015 | Jensen et al. | |
| 2017/0137365 | A1* | 5/2017 | Wampler | C07C 45/41 |
| 2018/0361371 | A1* | 12/2018 | Johns | C07C 6/04 |

FOREIGN PATENT DOCUMENTS

| | | | |
|---|---|---|---|
| JP | 2003531818 | A | 10/2003 |
| JP | 2018535983 | A | 12/2018 |
| JP | 2018538301 | A | 12/2018 |
| JP | 2020507614 | A | 3/2020 |
| WO | 0136368 | A2 | 5/2001 |
| WO | 2011046872 | A2 | 4/2011 |
| WO | 2013163071 | A1 | 10/2013 |
| WO | 2014139030 | A1 | 9/2014 |
| WO | 2017087710 | A2 | 5/2017 |
| WO | 2017100585 | A1 | 6/2017 |
| WO | 2018034931 | A1 | 2/2018 |
| WO | 2018038928 | A1 | 3/2018 |
| WO | 2018150379 | A2 | 8/2018 |
| WO | 2018191373 | A1 | 10/2018 |
| WO | 2019222244 | A1 | 11/2019 |

OTHER PUBLICATIONS

Wuts, Peter G.M. and Greene, Theodora W. "Greene's Protective Groups in Organic Synthesis", 4th Ed, 2007, Wiley-Interscience, New York, ISBN: 9780470053478, 047005347X, https://www.google.com/books/edition/Greene_s_Protective_Groups_in_Organic_Sy/KPyGzoxfAt0C?hl=en, cover only.

Grudzień, Krzysztof, et al., "Mechanistic Studies of Hoveyda-Grubbs Metathesis Catalysts Bearing S-, Br-, I-, and N- coordinating Naphthalene Ligands", Chemistry—A European Journal , vol. 20, Issue10, Mar. 3, 2014, pp. 2819-2828, https://doi.org/10.1002/chem.201303826.

Xu, C. et al., "In Situ Methylene Capping: A General Strategy for Efficient Stereoretentive Catalytic Olefin Metathesis. The Concept, Methodological Implications, and Applications to Synthesis of Biologically Active Compounds," J. Am. Chem. Soc., 139(31):10919-10928, 2017.

Written Opinion of the International Searching Authority for PCT/US2021/035257 dated Sep. 17, 2021.

Liu Zhenxing, et al., "Ru-Based Catechothiolate Complexes Bearing an Unsaturated NHC Ligand: Effective Cross-Metathesis Catalysts for Synthesis of ( Z )-α,β-Unsaturated Esters, Carboxylic Acids, and Primary, Secondary, and Weinreb Amides", Journal of the American Chemical Society, American Chemical Society, (May 1, 2019), vol. 141, No. 17, doi: 10.1021/jacs.9b02318, ISSN 0002-7863, pp. 7137-7146, XP055883323.

Zachmann, Raphael J., and Furstner, Alois; "Light-Driven gem Hydrogenation: An Orthogonal Entry into "Second-Generation" Ruthenium Carbene Catalysts for Olefin Metathesis." Chemistry—A European Journal, vol. 27, Issue28, May 17, 2021, pp. 7663-7666, https://doi.org/10.1002/chem.202101176.

Mimoun, Hubert; "Selective reduction of carbonyl compounds by polymethylhydrosiloxane in the presence of metal hydride catalysts." The Journal of Organic Chemistry, 1999, 64, 7, 2582-2589, https://doi.org/10.1021/jo982314z.

Spasyuk, Denis, et al.,"Chemoselective hydrogenation of carbonyl compounds and acceptorless dehydrogenative coupling of alcohols", Journal of the American Chemical Society, 2015, 137, 11, 3743-3746, https://doi. org/10.1021/ja512389y.

Tan, Xuefeng, et al., "Highly efficient tetradentate ruthenium catalyst for ester reduction: especially for hydrogenation of fatty acid esters", Organic letters 17, No. 3 (2015): 454-457, https://doi.org/10.1021/ol503456j.

Werkmeister, Svenja, et al., "Catalytic hydrogenation of carboxylic acid esters, amides, and nitriles with homogeneous catalysts", Organic process research & development 18, No. 2 (2014): 289-302, https://doi.org/10.1021/op4003278.

* cited by examiner

Oleyl acetate (Z9-18Ac)
+
(Z)-Hex-3-ene (Z)-Dodec-9-en-1-yl acetate (Z9-12Ac)
+
Metathesis co-products

FIG. 4

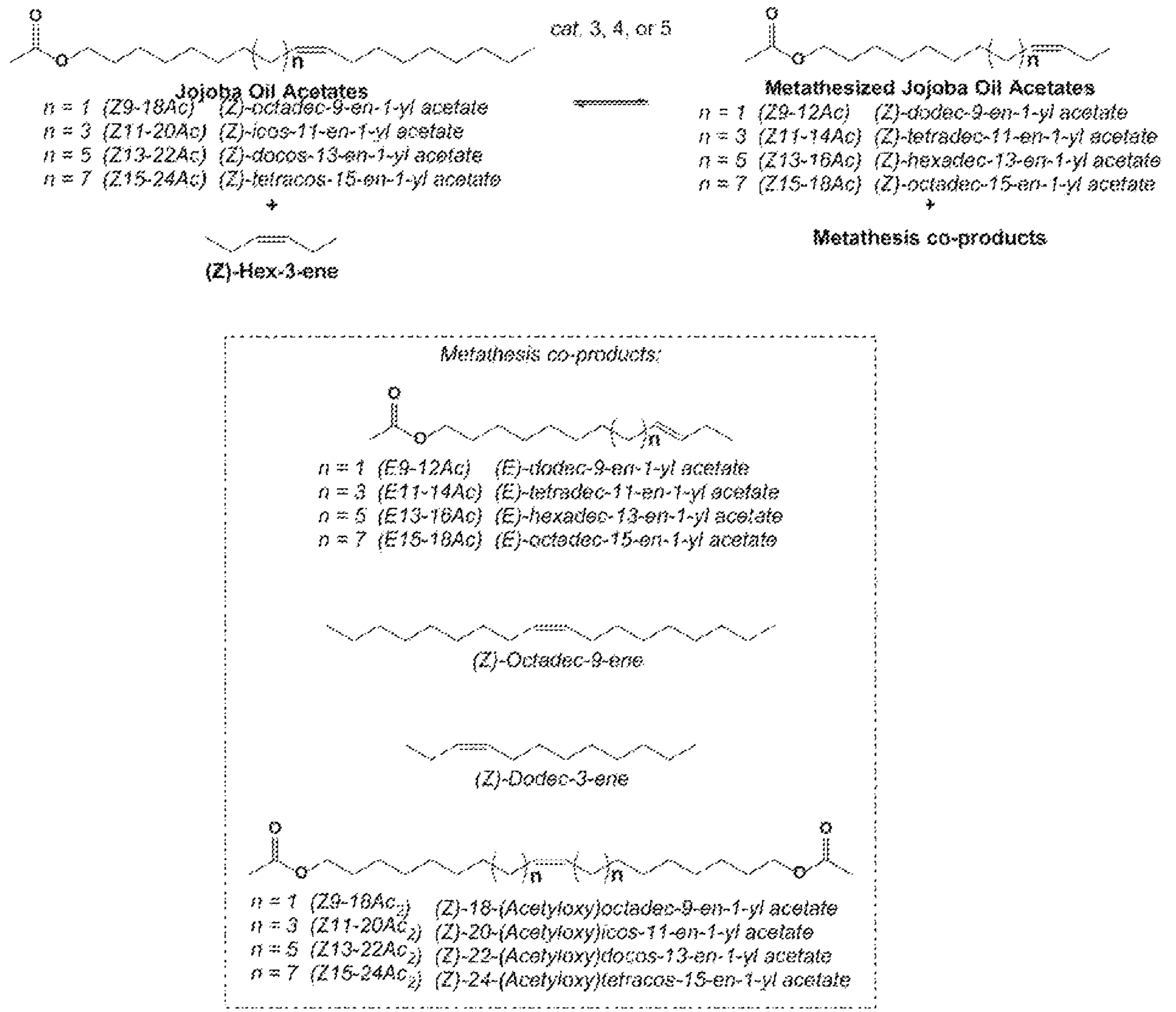

Jojoba Oil Acetates

*n = 1 (Z9-18Ac) (Z)-octadec-9-en-1-yl acetate*
*n = 3 (Z11-20Ac) (Z)-icos-11-en-1-yl acetate*
*n = 5 (Z13-22Ac) (Z)-docos-13-en-1-yl acetate*
*n = 7 (Z15-24Ac) (Z)-tetracos-15-en-1-yl acetate*

\+

(Z)-Hex-3-ene

Metathesized Jojoba Oil Acetates

*n = 1 (Z9-12Ac) (Z)-dodec-9-en-1-yl acetate*
*n = 3 (Z11-14Ac) (Z)-tetradec-11-en-1-yl acetate*
*n = 5 (Z13-16Ac) (Z)-hexadec-13-en-1-yl acetate*
*n = 7 (Z15-18Ac) (Z)-octadec-15-en-1-yl acetate*

\+

Metathesis co-products

*Metathesis co-products:*

*n = 1 (E9-12Ac) (E)-dodec-9-en-1-yl acetate*
*n = 3 (E11-14Ac) (E)-tetradec-11-en-1-yl acetate*
*n = 5 (E13-16Ac) (E)-hexadec-13-en-1-yl acetate*
*n = 7 (E15-18Ac) (E)-octadec-15-en-1-yl acetate*

*(Z)-Octadec-9-ene*

*(Z)-Dodec-3-ene*

*n = 1 (Z9-18Ac₂) (Z)-18-(Acetyloxy)octadec-9-en-1-yl acetate*
*n = 3 (Z11-20Ac₂) (Z)-20-(Acetyloxy)icos-11-en-1-yl acetate*
*n = 5 (Z13-22Ac₂) (Z)-22-(Acetyloxy)docos-13-en-1-yl acetate*
*n = 7 (Z15-24Ac₂) (Z)-24-(Acetyloxy)tetracos-15-en-1-yl acetate*

SYNTHESIS OF PHEROMONE DERIVATIVES VIA Z-SELECTIVE OLEFIN METATHESIS

CROSS-REFERENCES TO RELATED APPLICATIONS

This application is a continuation of International Application No. PCT/US2021/035257, filed on Jun. 1, 2021, which claims priority to U.S. Provisional Application No. 63/032,932, filed on Jun. 1, 2020, the disclosures of which are hereby incorporated by reference in their entirety for all purposes.

BACKGROUND OF THE INVENTION

As the global demand for food grows, there is an increasing need for effective pest control. Conventional insecticides are among the most popular chemical control agents because they are readily available, rapid acting, and highly reliable. However, the overuse, misuse, and abuse of these chemicals have led to resistant pests, alteration of the natural ecology, and in some cases, environmental damage.

The use of insect pheromones to control pest populations has gained increasing popularity as a viable, safe, and environmentally-friendly alternative to conventional insecticides. Since their discovery in the late 1950s, these molecules have shown efficacy in reducing insect populations through a variety of methods, including mass trappings, attract and kill, and mating disruption. The latter method in particular represents a non-toxic means of pest control and utilizes the ability of synthetic pheromones to mask naturally occurring pheromones, thereby causing confusion and mating disruption.

Although pheromones have significant potential in agricultural insect control, the cost of synthesizing pheromones using currently available techniques is very high, which prohibits widespread use of this sustainable technology beyond high-value crops. Thus, there is an existing need to develop novel technologies for the cost-efficient production of insect pheromones and related fragrances, flavors, and polymer intermediates. The present invention addresses this need with the synthetic methods capable of forming a wide-range of unsaturated fatty olefin metathesis products of high Z-isomeric purity, including synthetic insect pheromones, from low-cost feedstocks.

BRIEF DESCRIPTION OF THE DRAWINGS

FIG. 4 shows the synthesis of metathesized jojoba oil acetates via stereo-retentive olefin cross-metathesis using jojoba oil acetates with (Z)-hex-3-ene.

BRIEF SUMMARY OF THE INVENTION

Figure 1:
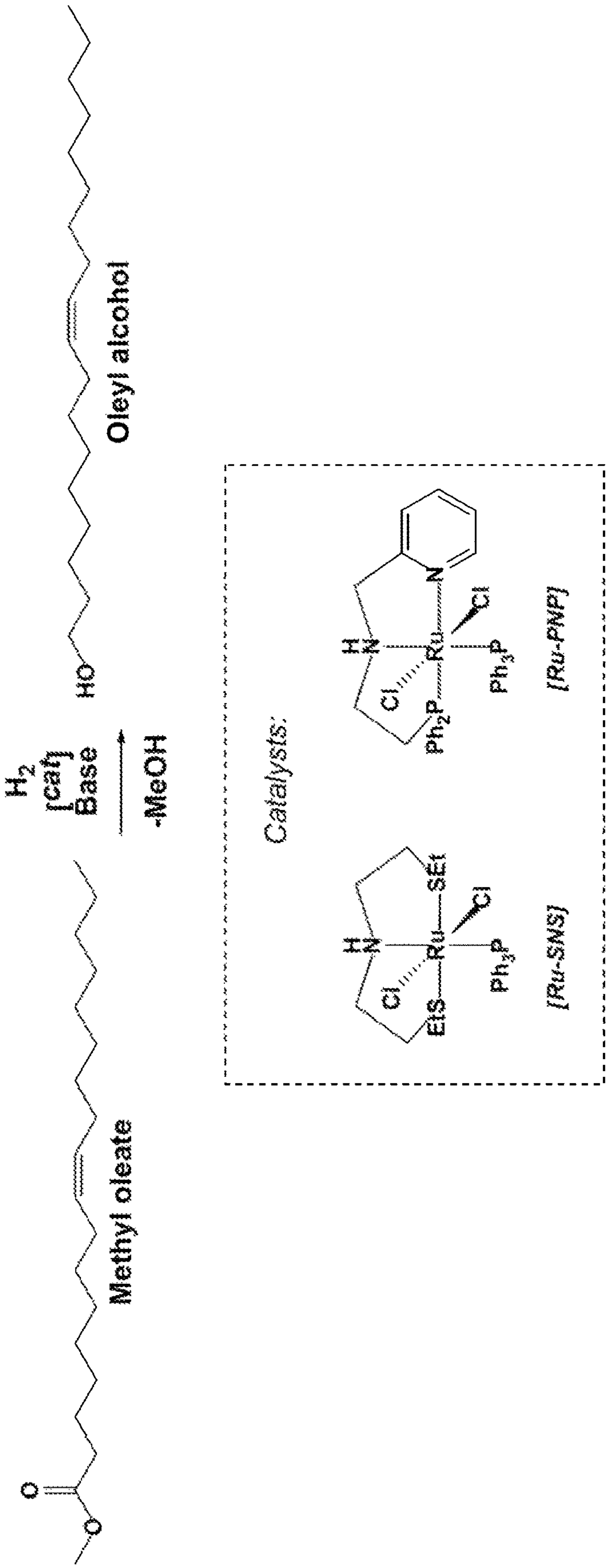
FIG. 1 shows the catalytic hydrogenation of methyl oleate to form oleyl alcohol.

Provided herein are methods for synthesizing a Z-enriched fatty olefin metathesis product. The methods include contacting an olefin metathesis reaction partner with an internal olefin in the presence of a group 8 transition metal metathesis catalyst to form the Z-enriched fatty olefin metathesis product, wherein;

- the fatty olefin metathesis product is an acylated alkenol an alkenal acetal,
- the olefin metathesis reaction partner comprises a mixture of Z olefins and E olefins in a starting Z:E ratio,
- the fatty olefin metathesis product comprises a mixture of Z olefins and E olefins in a product Z:E ratio, and
- the product Z:E ratio is higher than the starting Z:E ratio.

In some embodiments, the invention provides a method for synthesizing a fatty olefin metathesis product according to Formula I:

(I)

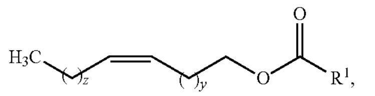

wherein the method includes contacting an olefin metathesis reaction partner according to Formula III (III)

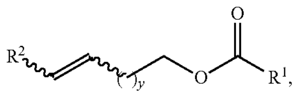

with an internal olefin according to Formula IV (IV)

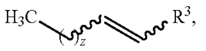

in the presence of a metathesis catalyst to form the fatty olefin metathesis product; wherein:

$R^1$ is selected from the group consisting of H and $C_{1-6}$ alkyl;

$R^2$ is selected from the group consisting of $C_{1-18}$ alkyl and $C_{2-18}$ alkenyl;

$R^3$ is $C_{1-18}$ alkyl;

subscript y is an integer ranging from 0 to 17;

subscript z is an integer ranging from 0 to 17; and the metathesis catalyst is a Z-selective group 8 transition metal catalyst.

In some embodiments, the metathesis catalyst is a Z-selective ruthenium catalyst or a Z-selective osmium catalyst.

In some embodiments, the metathesis catalyst used in the methods for synthesizing a fatty olefin metathesis product of Formula I is a Z-selective metathesis catalyst having a structure according to Formula V:

(V)

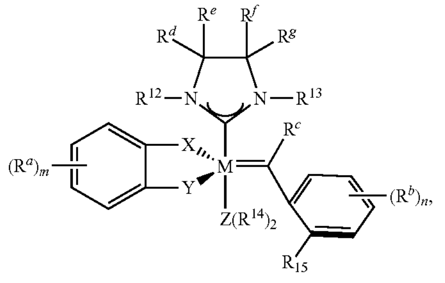

wherein:

M is selected from the group consisting of ruthenium and osmium;

X and Y are independently selected from the group consisting of S and O;

Z is selected from the group consisting of O, S(=O), N, and halogen;

each subscript m and subscript n is an integer independently selected from 0, 1, 2, 3, and 4;

each $R^a$ is independently selected from the group consisting of halogen, $C_1$-$C_6$ alkoxy, aryl, and heteroaryl; or one $R^a$ is taken together with an adjacent $R^a$ to form an unsubstituted substituted bicyclic ring, or an unsubstituted or substituted polycyclic ring;

each $R^b$ is independently selected from the group consisting of halogen, $C_1$-$C_6$ alkyl, alkoxy, aryl, and heteroaryl; or one $R^b$ is taken together with an adjacent $R^b$ to form an unsubstituted or substituted bicyclic ring, or an unsubstituted or substituted polycyclic ring;

$R^c$ is selected from the group consisting of hydrogen and $C_1$-$C_6$ alkyl;

each $R^d$, $R^e$, $R^f$, and $R^g$ is independently selected from the group consisting of hydrogen and $C_1$-$C_6$ alkyl;

$R^{12}$ and $R^{13}$ are independently selected from the group consisting of 2,4,6-tri-iso-propylphenyl, 2,6-di-iso-propylphenyl, 2,6-di-adamantylphenyl, 2-iso-propyl-6-tert-butylphenyl, 2,4,6-tri-tert-butyphenyl, and 2,6-di-tera-butyphenyl;

each $R^{14}$ is independently selected from the group consisting of hydrogen, methyl, ethyl, n-propyl, iso-propyl, n-butyl, tert-butyl, cyclohexyl, benzyl, and phenyl; and $R^{15}$ is selected from the group consisting of hydrogen, halogen, and $C_1$-$C_6$ alkyl, or $R^{15}$ and one $R^{14}$ are taken together to form a bond.

In some embodiments, the method for synthesizing the fatty olefin metathesis product of Formula I further includes forming the olefin metathesis reaction partner of Formula III by contacting an acylating agent with an alkenol according to Formula II (II)

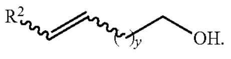

In some embodiments, the method for synthesizing the fatty olefin metathesis product further includes forming the alkenol of Formula II by reducing an unsaturated fatty carboxyl derivative according to Formula IIa (IIa)

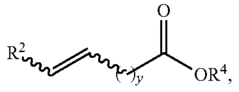

wherein $R^4$ is selected from the group consisting of H and $C_{1-8}$ alkyl.

In some embodiments, the synthesis of the fatty olefin metathesis product comprises forming the internal olefin by contacting a terminal olefin with a metathesis catalyst to form the internal olefin.

DETAILED DESCRIPTION OF THE INVENTION

I. Introduction

The present invention provides methods for the synthesis of high purity fatty olefin derivatives (such as straight-chain lepidopteran pheromones; SCLPs) through the stereo-retentive olefin cross-metathesis of internal olefins having low isomeric purity. Through the use of various low purity fatty olefin derivative-feedstocks and internal olefin-feedstocks in concert with Z-selective olefin metathesis catalysts, a wide variety of pheromones with high Z-purity can be obtained. The invention allows for the use of low isomeric purity, commercially available olefin feedstocks to prepare high purity SCLPs, greatly increasing the industrial applicability of such technology.

II. Definitions

The following definitions and abbreviations are to be used for the interpretation of the invention. The term "invention" or "present invention" as used herein is a non-limiting term and is not intended to refer to any single embodiment but encompasses all possible embodiments.

As used herein, the terms "comprises," "comprising," "includes," "including," "has," "having," "contains," "containing," or any other variation thereof, are intended to cover a non-exclusive inclusion. A composition, mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive "or" and not to an exclusive "or."

The terms "about" and "around," as used herein to modify a numerical value, indicate a close range surrounding that explicit value. If "X" were the value, "about X" or "around X" would indicate a value from 0.9X to 1.1X, and in certain instances, a value from 0.95X to 1.05X or from 0.98X to 1.02X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "099X."

As used herein, the term "substantially" describes a range of values of from about 85 to 100%, such as, for example, 85-99.9%, 90 to 99.9%, 95 to 99.9%, 98 to 99.9%, or from 99 to 99.9%.

As used herein, the term "predominantly" refers to a proportion in the range of above 50%, such as, for example, in the ramie of about 51 to 100%, 75 to 99.9%, 85 to 98.5%, or from about 95 to 99%.

As used in the specification and the appended claims, the singular forms "a," "an," and "the" include plural referents unless the context clearly dictate otherwise. Thus, for example, reference to "a fatty olefin metathesis product" includes a single fatty olefin metathesis product as well as a combination or mixture of two or more fatty olefin metathesis products (e.g., a mixture of fatty Z-olefin and fatty E-olefin metathesis products); reference to "an unsaturated fatty carboxyl derivative" includes a single unsaturated fatty carboxyl derivative as well as a combination or mixture of two or more unsaturated fatty carboxyl derivatives; reference to "an alkenol" includes a single alkenol as well as a combination or mixture of two or more alkenols; reference to "a substituent" encompasses a single substituent as well as two or more substituents, and the like.

As used herein, the term "metathesis product" refers to an olefin containing at least one double bond, the band being formed via a metathesis reaction. As used herein, the term "fatty olefin metathesis product" refers to a type of olefin-containing compound formed via a metathesis reaction (i.e., a type of metathesis product formed from an olefin and a metathesis reaction partner), which has the structure R—C(O)O—R' wherein R is an alkyl group as described below, and R' is a linear alkenyl group comprising at least four carbon atoms, e.g. 4, 6, 8, 10, 12, 14, 16, 18, 20, 22, 24, 26, 28, 30, 32, 34, 36, 38, or 40 carbon atoms. In some embodiments, R' is a $C_4$ to $C_{30}$ linear alkenyl group. As non-limiting, example, an "unsaturated fatty ester acetate" is a fatty olefin metathesis product resulting from the cross-metathesis of an olefin metathesis reaction partner with an olefin, in which R of R—C(O)O—R' is a methyl group and R' is a $C_2$ to $C_{26}$ linear alkenyl group. In the context of the present invention, "$C_8$-$C_{28}$ (Z)-unsaturated fatty ester acetate" is also a non-limiting example of a fatty olefin metathesis product. In some embodiments, a fatty olefin metathesis product is a pheromone, such as, for example, a straight-chain lepidopteran pheromone (SCLPs).

As used herein, the term "metathesis reaction" refers to a catalytic reaction which involves the interchange of alkylidene units (i.e., $R_2C$=units) among compounds, containing one or more carbon-carbon double bonds (e.g., olefinic compounds) via the formation and cleavage of the carbon-carbon double bonds. Metathesis can occur between two molecules having the same structure (often referred to as self-metathesis) and/or between two molecules having different structures (often referred to as cross-metathesis).

As used herein, the term "pheromone" refers to a substance, or characteristic mixture of substances, that is secreted and released by an organism and detected by a second organism of the same species or a closely related species. Typically, detection of the pheromone by the second organism promotes a specific reaction, such as a definite behavioral reaction or a developmental process. Insect pheromones, for example, can influence behaviors such as mating and aggregation. Examples of pheromones include, but are not limited to, compounds produced by Lepidoptera (i.e., moths and butterflies belonging to the *Geometridae, Noctuidae, Arctiidae*, and *Lymantriidae* families) such as $C_{10}$-$C_{18}$ acetates, $C_{10}$-$C_{18}$ alcohols, $C_{10}$-$C_{18}$ aldehydes, and $C_{17}$-$C_{23}$ polyenes. An "unsaturated pheromone" refers to any pheromone having at least one carbon-carbon double bond.

As used herein, the term "contacting" refers to the process of bringing into contact at least two distinct species such that they can react. It should be appreciated, however, that the resulting reaction product can be produced directly from a reaction between the added reagents or from an intermediate from one or more of the added reagents that can be produced in the reaction mixture.

As used herein, the term "metathesis reaction partner" refers to a compound having a carbon-carbon double bond that can react with an olefin in a metathesis reaction to form a new carbon-carbon double bond. The metathesis reaction partner can be a fatty olefin-containing compound, such as an olefin metathesis reaction partner; The term "olefin metathesis reaction partner" refers to a compound having the structure R—C(O)O—R' wherein R is an alkyl group as described below, and R' is a linear alkenyl group comprising at least four carbon atoms, e.g., 4, 6, 8, 10, 12, 14, 16, 18, 20, 22, 24, 26, 28, 30, 32, 34, 36, 38, or 40 carbon atoms. In some embodiments, R' is a $C_6$ to $C_{34}$ linear alkenyl group. For example, an "unsaturated fatty alcohol acetate" is an olefin metathesis reaction partner in which R of R—C(O)O—R' is a methyl group and R' is a $C_4$ to $C_{28}$ linear alkenyi group. Further non-limiting examples of an olefin metathesis reaction partner include "fatty $C_{12}$-$C_{30}$ olefin acetate" and "acetate ester of a $C_{10}$-$C_{28}$ fatty alkenol" in which R of R—C(O)O—R' is a methyl group and R' is a $C_{10}$ to $C_{28}$ linear alkenyl group.

As used herein, the term "olefin" refers to a straight-chain (e.g., linear) or branched hydrocarbon compound containing at least one carbon-carbon double bond and derivatives thereof. The olefin can be unsubstituted or substituted with one or more functional groups including alcohol groups, protected alcohol croups, carboxylate groups, and carboxylic acid ester groups. As used herein, the term "olefin" encompasses hydrocarbons having inure than one carbon-carbon double bond (e.g., di-olefins, tri-olefins, etc.). Hydrocarbons having more than one carbon-carbon double bond and derivatives thereof are also referred to as "polyenes," The term "fatty olefin" refers to an olefin having at least four carbon atoms; fatty olefins can have, for example, 4, 6, 8, 10, 12, 14, 16, 18, 20, 22, 24, 26, 28, 30, 32, 34, 36, 38, or 40 carbon atoms. Olefins may contain terminal double band(s) ("terminal olefin") and/or internal double bond(s) ("internal olefin"). In some embodiments, the olefins used in the methods of the invention have from 4 to 26 carbon atoms. In certain other embodiments, the olefins used in the methods of the present invention comprise a mixture of olefins having anywhere from 4 to 26 carbon atoms.

As used herein, the term "internal olefin" refers to an olefin wherein each of the olefinic carbons (i.e., the carbons of the carbon-carbon double bond; C═C) is substituted by at least one non-hydrogen substituent (e.g., $R^{1'}R^{2'}C{=}CR^{3'}R^{4'}$, wherein at least one of $R^{1'}$ and $R^{2'}$ are not hydrogen and at least one of $R^{3'}$ and $R^{4'}$ are not hydrogen). The internal olefin may be di-substituted, tri-substituted, or tetra-substituted (e.g., di-substituted internal olefin; $R^{5'}HC{=}CHR^{8'}$ and/or $HR^{6'}C{=}CR^{7'}H$; tri-substituted internal olefin: $R^{5'}R^{6'}C{=}CHR^{8'}$, $R^{5'}R^{6'}C{=}CR^{7'}H$, $R^{5'}HC{=}CR^{7'}R^{8'}$, and/or $HR^{6'}C{=}CR^{7'}R^{8'}$; and tetra-substituted internal olefin: $R^{5'}R^{6'}C{=}CR^{7'}R^{8'}$; where $R^{5'}$, $R^{6'}$, $R^{7'}$, and $R^{8'}$ may be the same or different and are each independently optionally substituted aliphatic group, optionally substituted heteroaliphatic group, or a functional group).

As used herein, the term "terminal olefin" refers to an olefin wherein one of the olefinic carbons (i.e., the carbons of the carbon-carbon double bond; C═C) is substituted by at least one non-hydrogen substituent and the other olefinic carbon is unsubstituted (e.g., $R^{9'}R^{10'}C{=}CH_2$, wherein at least one or both of $R^{9'}$ and $R^{10'}$ are not hydrogen). The terminal olefin may be mono-substituted or di-substituted. (e.g., mono-substituted terminal olefin: $R^{9'}HC{=}CH_2$ and/or $HR^{10'}C{=}CH_2$; and di-substituted terminal olefin: $R^{9'}HC{=}CH_2$; where $R^{9'}$ and $R^{10'}$ may be the same or different and are each independently optionally substituted aliphatic group, optionally substituted heteroaliphatic group, or a functional group).

A "fatty olefin derivative" refers to a compound obtained from an olefin starting material, or a fatty olefin starting material used in the methods of the present invention. Examples of fatty olefin derivatives include, but are not limited to, unsaturated fatty alcohols (i.e., alkenols), unsaturated fatty alcohol acetates and unsaturated fatty ester acetates (e.g., olefin metathesis reaction partner and fatty olefin metathesis product), unsaturated fatty aldehydes, unsaturated fatty carboxyl derivative (e.g., unsaturated fatty acids, unsaturated fatty acid alkyl esters), and polyenes. In the context of the instant invention, a "metathesis product" and a "fatty olefin metathesis product" are both types of fatty olefin derivatives. In some embodiments, the fatty olefin derivatives used in the methods of the invention have from 6 to 34 carbon atoms. In some embodiments, the fatty olefin derivatives synthesized according to the methods of the invention have from 6 to 30 carbon atoms. In certain other embodiments, the fatty olefin derivatives used in the methods of the present invention comprise a mixture of fatty olefin derivatives having anywhere from 4 to 34 carbon atoms. In certain other embodiments, the fatty olefin derivatives synthesized according to the methods of the invention comprise a mixture of linty olefin derivatives having anywhere from 4 to 30 carbon atoms.

A $\Delta^9$-unsaturated olefin refers to an olefin wherein the ninth carton-carbon bond from the end of an olefin chain is a double bond (e.g., $\Delta^9$-unsaturated fatty alcohol, $\Delta^9$-unsaturated fatty alcohol acetates, $\Delta^9$-unsaturated fatty ester acetates, $\Delta^9$-unsaturated fatty aldehydes, $\Delta^9$-unsaturated fatty carboxyl derivative, $\Delta^9$-unsaturated fatty acids, $\Delta^9$-unsaturated fatty acid alkyl esters etc.). For example, a $\Delta^9$-unsaturated fatty acid refers to an olefinic carboxylic acid wherein the ninth carbon-carbon bond counted from the carboxylic acid end of the olefin chain is a double bond. Examples of $\Delta^9$-unsaturated fatty acids include, but are not limited to, 9-decenoic acid, oleic acid (i.e., (Z)-octadec-9-enoic acid), and elaidic acid (i.e., (E)-octadec-9-enoic acid). As another non-limiting example, a $\Delta^9$-unsaturated fatty ester acetate refers to an olefinic ester acetate wherein the ninth carbon-carbon bond counted from the acetate end of the olefin chain is a double bond. Examples of $\Delta^9$-unsaturated fatty ester acetates include, but are not limited to, 9-decenyl acetate, (Z)-tetradec-9-en-1-yl acetate, and (E)-tetradec-9-en-1-yl acetate.

Similarly, a $\Delta^{11}$-unsaturated olefin refers to an olefin wherein the eleventh carbon-carbon bond from the end of an olefin chain is a double bond (e.g., $\Delta^{11}$-unsaturated fatty alcohol, $\Delta^{11}$-unsaturated fatty alcohol acetates, $\Delta^{11}$-unsaturated fatty ester acetates, $\Delta^{11}$-unsaturated fatty aldehydes, $\Delta^{11}$-unsaturated fatty carboxyl derivative, $\Delta^{11}$-unsaturated fatty acids, $\Delta^{11}$-unsaturated fatty acid alkyl esters, etc.). For example, a $\Delta^{11}$-unsaturated fatty acid refers to an olefinic carboxylic acid wherein the eleventh carbon-carbon bond counted from the carboxylic acid end of the olefin chain is a double bond. Examples of $\Delta^{11}$-unsaturated fatty acids include, but are not limited to, 11-dodecenoic acid, gondoic acid (i.e., (Z)-icos-11-enoic acid or (Z)-eicos-11-enoic acid), and trans-gondoic acid (i.e., (E)-icos-11-enoic acid or (E)-icos-11-enoic acid). It should be noted that the prefixes "ions" and "eicos" are used interchangeably to refer to a hydrocarbon chain having 20 carbons (e.g., a completely saturated $C_{20}$ hydrocarbon chain, i.e., alkyl; or a $C_{20}$ hydrocarbon chain containing one or more units of unsaturation, i.e., alkenyl or olefin). As another non-limiting example, a $\Delta^{11}$-unsaturated fatty ester acetate refers to an olefinic ester acetate wherein the eleventh carbon-carbon bond counted from the acetate end of the olefin chain is a double bond. Examples of $\Delta^{11}$-unsaturated fatty ester acetates include, but are not limited to, 11-dodecenyl acetate, (Z)-tetradec-11-en-1-yl acetate, and (E)-tetradec-11-en-1-yl acetate.

As used herein, the terms "alkeno" and "fatty alkenol" are used interchangeably and refer to a compound having the structure R'—OR wherein R' is a linear alkenyl group comprising at least four carbon atoms, e.g., 4, 6, 8, 10, 12, 14, 16, 18, 20, 22, 24, 26, 28, or 30 carbon atoms, and R is hydrogen or an alcohol protecting group. In some embodiments, R' is a $C_6$ to $C_{34}$ linear alkenyl group. As non-limiting example, a "$C_{10}$ to $C_{28}$ fatty alkenol" is an alkenol (i.e., fatty alkenol) in which R of R'—OR is hydrogen and R' is a to $C_{10}$ to $C_{28}$ linear alkenyl group.

As used herein, the term "unsaturated fatty carboxyl derivative" refers to fatty olefin compound comprising a carboxyl moiety and used in the methods of Me present invention. The term "carboxyl" as used herein, represents a group of formula "—C(O)O—". In the context of the present invention, unsaturated fatty carbonyl derivatives include "unsaturated fatty acids" and "unsaturated fatty acid alkyl esters." The term "unsaturated fatty acid" as used herein refers to a compound having the structure R'—C(O)OH, wherein R' is a linear alkenyl group comprising at least four carbon atoms, e.g., 4, 6, 8, 10, 12, 14, 16, 18, 20, 22, 24, 26, 28, 30, 32, 34, 36, 38, or 40 carbon atoms. In some embodiments, R' of R'—C(O)OH is a $C_6$ to $C_{34}$ linear alkenyl group. As a non-limiting example, a "$C_{12}$-$C_{30}$ unsaturated fatty acid" is an unsaturated fatty acid in which R' of R'—C(O)OH is a $C_{11}$-$C_{29}$ linear alkenyl group. The term "unsaturated fatty acid alkyl ester" as used herein refers to a compound having the structure R'—C(O)O—R, wherein R' is a linear alkenyl group comprising at least four carbon atoms, e.g., 4, 6, 8, 10, 12, 14, 16, 18, 20, 22, 24, 26, 28, 30, 32, 34, 36, 38, or 40 carbon atoms, and R is an alkyl group as described below. In some embodiments, R' of R'—C(O)O—R is a $C_6$ to $C_{34}$ linear alkenyl group. As a non-limiting example, a "$C_{12}$-$C_{30}$ unsaturated fatty acid methyl ester" is an unsaturated fatty acid alkyl ester in which R of R'—C(O)O—R is a methyl group and R' is a $C_{10}$-$C_{28}$ linear alkenyl group. The unsaturated fatty carboxyl derivative can be a mixture of different unsaturated fatty acids or a mixture of different unsaturated fatty acid alkyl esters. In some embodiments, the unsaturated fatty carboxyl derivative is obtained from a natural oil or a natural oil derivative.

As used herein, the term "isomer" refers to a molecule having the same chemical formula as another molecule, but with a different chemical structure. That is, isomers contain the same number of atoms of each element, but have different arrangements of their atoms Isomers include "structural isomers" and "stereoisomers." In "structural isomers" (also referred to as "constitutional isomers"), the atoms have a different bond-sequence. Structural isomers have different IUPAC names and may or may not belong to the same functional group. This type of isomer includes skeletal isomers wherein hydrocarbon chains have variable amounts of branching, and positional isomers, which deals with the position of a functional group on a chain; and functional group isomerism, in which the molecular formula is the same but the functional group is different.

As used herein, the term "positional isomer" refers to a first compound which has the same carbon skeleton and functional group as a second compound, but differs in the location of the functional group on or in the carbon skeleton, in a particular embodiment, a positional isomer can have a functional group (e.g., alkene, hydroxyl, aldehyde, and acetyl, etc.) located at different locations of a carbon skeleton compared to an positional isomer thereof. For example, a positional isomer of (Z)-tetradec-9-en-1-yl acetate is (Z)-tetradec-11-en-1-yl acetate, because (Z)-tetradec-9en-1-yl acetate is produced via cross-metathesis of (Z)-octadec-9-en-1-yl acetate with (Z)-dec-5-ene, and (Z)-tetradec-11-en-1-yl acetate is produced via cross-metathesis of (Z)-icos-11-en-1-yl acetate with (Z)-hex-3-ene.

In stereoisomers, the bond structure is the same, but the geometrical positioning of atoms and functional groups in space differs. This class of isomers includes enantiomers, which are isomers that are non-superimposable mirror-images of each other, and diastereomers, which are stereoisomers that are not mirror-images. Geometric isomers, or cis/trans isomers, are diastereomers that differ in the stereochemical orientation of substituent atoms at a bond. The double bonds within the olefins and fatty olefin derivatives described herein preclude rotation of the molecules by fixing it in one of two possible configurations, each representing geometric isomers that are different molecules. These geometric isomers are designated either E (from the German word Entgegen, opposite) or Z (Zusammen, together), when the carbon chains are connected on the opposite (trans) or same (cis) side, respectively, of the double bond. Therefore, the olefins and fatty olefin derivatives described herein may be of the (E) configuration, the (Z) configuration, or of a mixture of (E) and (Z) configuration. Another type of isomer, conformational isomers (conformers), may be rotamers, diastereomers, or enantiomers depending on the exact compound.

As used herein, the term “stereoselectivity” describes the ability to produce a particular stereoisomer of a compound (i.e., olefin or fatty olefin derivative described herein) in an isomerically pure fora (e.g., about 90% Z-isomer or about 90% E-isomer) or to specifically produce a particular stereoisomer of a fatty olefin derivative in the presence of a metathesis catalyst according to the methods described herein. In the context of the present invention, “stereoselective” or “selective” refers to a cross-metathesis reaction that preferentially results in one stereoisomer relative to a second stereoisomer, i.e., gives rise to a metathesis product or fatty olefin metathesis product of which the ratio of a desired stereoisomer to a less desired stereoisomer is greater than 1:1.

“Z-stereoselectivity” or “Z-selectivity” describes the ability to produce the Z-isomer of a compound (i.e., olefin or fatty olefin derivative described herein) in a Z-isomerically pure form, or predominantly pure form, or substantially pure form; or to specifically produce the Z-isomer of a fatty olefin derivative from the combination of i.) a mixture of E- and Z-isomers of a metathesis reaction partner (e.g., an acylated olefin metathesis reaction partner); and ii.) an olefin, which may optionally comprise a mixture of E- and Z-isomers, or may be at least 95% Z; in the presence of a metathesis catalyst, according to the methods described herein. Further in the context of the present invention, “Z-stereoselective” or “Z-selective” refers to a cross-metathesis reaction that preferentially results in the Z-isomer relative to the E-isomer, gives rise to a Z-fatty olefin metathesis product of which the ratio of Z-isomer to the E-isomer is greater than 1:1. A “Z-selective catalyst” refers to a group 8 transition metal catalyst, as described herein, which preferentially produces the Z-fatty olefin metathesis product in a cross-metathesis reaction methods of the present invention. The Z-selectivity may also be expressed as a percentage of isomeric product formed. For example, the fatty olefin derivatives (e.g., metathesis products, fatty olefin metathesis products, etc.) prepared according to the methods of the present invention are at least 80% Z, typically greater than 85% Z, or 90% Z, or 95% Z, and preferably greater than 97% Z, or greater than 98% Z, or greater than 99% Z, or greater than 99.5% Z, or greater than 99.9% Z.

In the context of an individual isomer the terms “isomeric purity” or “isomerically pure” are used interchangeably and refer to the amount or concentration of a particular isomer of an olefin or fatty olefin derivative relative to the total amount or concentration of all isomeric forms of the olefin or fatty olefin derivative. Each of the fatty olefin derivatives (e.g., metathesis products, fatty olefin metathesis products, etc.) prepared according to the methods of the present invention are substantially Z-isomerically pure. In other words, the fatty olefin derivatives (e.g., metathesis products, fatty olefin metathesis products, etc.) prepared according to the methods of the present invention are greater than 80% Z-isomer, typically greater than 85% Z-isomer, or 90% Z-isomer, or 95% Z-isoiner, and more preferably greater than 97% Z-isomer, or greater than 98% Z-isomer, or greater than 99% Z-isomer, or greater than 99.5% Z-isomer, or greater than 99.9% Z-isomer.

As used herein, the term “Z:E ratio” refers to proportion of the amount of Z-isomer (e.g., Z-fatty olefin metathesis product) relative to the amount of E-isomer (e.g., E-fatty olefin metathesis product), As used herein, the term “Z-enriched” refers to a material (e.g., a metathesis product) with a higher Z:E ratio than a precursor material (e.g., a metathesis reaction partner).

As used herein, the term “low isomeric purity” refers to olefins, metathesis reaction partners, olefin starting material, olefin-containing reactant, and fatty olefin derivative (e.g., alkenols, unsaturated fatty alcohol acetates, unsaturated fatty ester acetates, olefin metathesis reaction partners, fatty olefin metathesis products, unsaturated fatty aldehydes, unsaturated fatty carboxyl derivatives, metathesis products, etc.) used in or produced from the methods of the instant invention, which are less than 90% Z-isomer (i.e., 10% or more E-isomer), As used herein, the term “highly Z-selective” means that more than 85% of the formed metathesis products and/or fatty olefin metathesis products are in the Z-configuration.

As used herein, the term “metathesis catalyst” refers to any catalyst or catalyst system that catalyzes a metathesis reaction. One of skill in the art will appreciate that a metathesis catalyst cart participate in a metathesis reaction so as to increase the rate of the reaction, but is itself not consumed in the reaction. A “ruthenium catalyst” refers to a metathesis catalyst having one or more ruthenium atoms. An “osmium catalyst” refers to a metathesis catalyst having one or more osmium atoms.

As used herein, the terms “forming” and “converting” are used interchangeably and refer to reacting a starting material with at least one reagent to form an intermediate species or a product. The forming or converting can also include reacting an intermediate with at least one reagent to form a further intermediate species or a product.

The term “functional group” encompasses at functional group that is known in the art.

As used herein, the term “acyl” refers to the functional group —C(O)—R, wherein R is an alkyl group as described below.

As used herein, the term "acylating" refers to converting an alcohol group (—OH), to an ester group (—OC(O)—R), where R is an alkyl group as described below.

As used herein, the term "acylating agent" refers to a compound that is capable of reacting with a substrate compound to add a —C(O)—R moiety to a compound. An acylating agent can be used, for example, to form an ester (i.e., —C(O)O—R) on a compound having a hydroxyl moiety (i.e., —OH). Acylating agents useful in the present invention may be one or more $C_1$-$C_{20}$ straight or branched chain alkyl or aryl carboxylic anhydrides, carboxylic acid halides, diketene or acetoacetic acid esters. Examples of carboxylic anhydrides suitable for use as acylating agents in the present invention include, but are not limited to acetic anhythide propionic anhydride, butyric anhydride, isobutyric anhydride, valeric anhydride, hexanoic anhydride, 2-ethylhexanoic anhydride, nonanoic anhydride, Lauric anhydride, palmitic anhydride, stearic anhydride, benzoic anhydride, substituted benzoic anhydride, phthalic anhydride and isophthalic anhydride. Examples of carboxylic acid halides suitable for use as acylating agents in the present invention include acetyl, propionyl, butyryl, hexanoyl, 2-ethylhexanoyl, lauroyl, palmitoyl and stearoyl chloride. Examples of acetoacetic acid esters suitable for use as acylating agents in the present invention include, but are not limited to, methyl acetoacetate, ethyl acetoacetate, propyl acetoacetate, butyl acetoacetate and tert-butyl acetoacetate.

As used herein, the term "alkenyl" refers to an alkyl group, as defined herein, having one or more double bonds. The term "heteroalikenyl" refers to an alkenyl group wherein one or more carbon atoms is replaced with a heteroatom (i.e., nitrogen, oxygen, or sulfur, including any oxidized form of nitrogen or sulfur, and any quaternized form of a basic nitrogen).

As used herein, the term "reducing" refers to the transfer of electron density from a hydrogenation catalyst or reducing agent to a substrate compound. The electron density transfer typically occurs via a process including addition of hydrogen to the substrate compound.

As used herein, the term "reducing agent" refers to any reagent that is effective reducing a carboxylic acid group (i.e., —C(O)OH) to an alcohol group (i.e., —$CH_2$OH). Examples of reducing agents include, but are not limited to, sodium borohydride, sodium triacetoxyborohydride, sodium cyanoborohydride, lithium aluminum hydride, and sodium bis(2-methoxyethoxy)aluminum hydride.

As used herein, the term "hydrogenation catalyst" refers to any catalyst that is effective in hydrogenating an alkyl ester group (i.e., —C(O)O—R) to an alcohol group (i.e., —$C_2$—OH), wherein R is an alkyl group as described below. The hydrogenation catalyst can be a heterogeneous catalyst or a homogenous catalyst.

In the context of the present invention, the term "heterogeneous" refers to reaction conditions in which one or more reagents or participants (i.e., a heterogeneous catalyst) do not dissolve in a reaction medium; or, in ether words, one or more reagents or participants are in a different phase (for example, a solid catalyst) than the other solvents, reagents, compounds, or substrates (for example, liquid or vapor) when mixed together. The term "homogeneous" refers to reaction conditions in which all the reagents or participants (i.e., a homogenous catalyst) are soluble in a reaction medium (i.e. in the same phase as the other solvents, reagents, compounds, or substrates when mixed together). The terms "heterogeneous" and "homogenous" can also refer to a catalyst. For example a "heterogeneous catalyst" refers to a catalyst which does not dissolve in a reaction medium; or, in other words, a catalyst that is in a different phase (for example, a solid catalyst) than the other solvents, reagents, compounds, or substrates (for example, liquid or vapor) when mixed together. A "homogeneous catalyst" refers to a catalyst which is soluble in a reaction medium (i.e., in the same phase as the other solvents, reagents, compounds, or substrates when mixed together).

The term "aliphatic" or "aliphatic group," as used herein, means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as "carbocycle" or "cycloaliphatic"), that has a single point of attachment to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. In some embodiments, "cycicialiphatic" (or "carbocycle") refers to a monocyclic $C_3$-$C_6$ hydrocarbon, or a $C_8$-$C_{10}$ bicyclic hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as cycloalkyl)alkyl, (cycloalkenyl)alkyl, or (cycloalkyl)alkenyl. The term "heteroaliphatic" refers to an aliphatic group wherein at least one carbon atom of the aliphatic group is replaced with a heteroatom (i.e., nitrogen, oxygen, or sulfur, including any oxidized form of nitrogen or sulfur, and any quaternized form of a basic nitrogen).

As used herein, the term "alkyl" is given its ordinary meaning in the art and includes straight chain (i.e., linear) or branched, saturated, aliphatic radical groups having the number of carbon atoms indicated. A straight chain or branched chain alkyl has about 1-40 carbon atoms in its backbone, e.g., 1, 2, 3, 4, 5, 6, 7, 8, 10, 11, 12, 14, 16, 18, 20, 22, 24, 26, 28, 30, 32, 34, 36, 38, or 40 carbon atoms. In some embodiments, a straight chain or linear alkyl is $C_1$-$C_{30}$, and a branched chain alkyl is $C_3$-$C_{30}$. In some cases, a straight chain or branched chain alkyl has about 1-20 carbon atoms in its backbone. In some embodiments, a linear chain or branched chain alkyl group has about 1-10 carbon atoms in its backbone, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-10}$ alkyl includes, but is not limited to, methyl, ethyl, propyl, isopropyl, butyl, isobutyl, sec-butyl, tert-butyl, pentyl, isopentyl, hexyl, heptyl, octyl, nonyl, decyl, etc. In some embodiments, an alkyl group may be a lower alkyl group, wherein a lower alkyl group comprises 1-4 carbon atoms (e.g., $C_1$-$C_4$ for straight chain lower alkyls).

As used herein, the term "heteroalkyl" is given its ordinary meaning in the art and refers to alkyl groups as described herein in which one or more carbon atoms is replaced with include, are not limited to, alkoxy, poly (ethylene glycol)-, alkyl-substituted amino, and, the like.

As used herein, the term "alkoxy" refers to a moiety —OR wherein R is an alkyl group as defined above. The term "silylalkyl" refers to an alkyl group as defined herein wherein as least one carbon atom is replaced with a silicon atom. The term "silyloxy" refers to a moiety —$OSiR_3$, wherein each R is independently selected from the group consisting of H, alkyl, substituted alkyl, aryl, and substituted aryl as described herein.

As used herein, the term "cycloalkyl" refers to a saturated, monocyclic hydrocarbon, bicyclic hydrocarbon, or tricyclic hydrocarbon group that has a single point of attachment to the rest of the molecule. Cycloalkyl groups include alkyl substituted cycloalkyl groups and cycloalkyl substituted alkyl groups. In some embodiments, cycloalkyl rings have from about 3-10 carbon atoms in their ring structure where such rings are monocyclic or bicyclic, and alternatively about 5, 6 or 7 carbons in the ring structure.

As used herein, the term "alkynyl" refers to an alkyl group, as defined herein, having one or more triple bonds.

As used herein, the term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring," in certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like. The term "aryloxy" refers to a moiety —OR, wherein R is an aryl group as defined above.

As used herein, the terms l"heteroaryl" and "heteroar-," used alone or as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 pi electrons shared in a cyclic arrangement; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen, Heteroaryl groups include, without limitation, thienyl, furanyl, pyrrolyl, imidazolyl, pyrazolyl, triazolyl, tetrazolyl, oxazolyl, isoxazolyl, oxadiaxolyl, thiazolyt, isothiazolyl, thiadiazolyl pyridyl pyridazinyl, pyrimidinyl, pyrazinyl, indolizinyl, purinyl, naphthyridinyl, and pteridinyl. The terms "heteroaryl" and "heteroar-," as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

Examples of aryl and heteroaryl groups include, but are not limited to, phenyl, pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. It should be understood that, when aryl and heteroaryl groups are used as ligands coordinating a metal center, the aryl and heteroaryl groups may have sufficient ionic character to coordinate the metal center. For example, when a heteroaryl group such as pyrrole is used as a nitrogen-containing ligand, as described herein, it should be understood that the pyrrole group has sufficient ionic character (e.g., is sufficiently deprotonated to define a pyrrolyl) to coordinate the metal center. In some cases, the aryl or heteroaryl group may comprise at least one functional group that has sufficient ionic character to coordinate the metal center, such as a biphenolate group, for example.

As used herein, the terms "heterocycle," "hetercyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more heteroatoms (e.g., one to four heteroatoms), as defined above. When used in reference to a ring atom of a heterocycle, the term "nitrogen" includes a substituted nitrogen. As an example, in a saturated or partially unsaturated ring having 1-3 heteroatoms selected from oxygen, sulfur or nitrogen, the nitrogen may be N in 3,4-dihydro-2H-pyrrolyl), NH (as in pyrrolidinyl), or $^+NR$ (as in N-substituted pyrrolidinyl).

A heterocyclic ring can be attached to its pendant group at any heteroatom or carbon atom that results in, a stable structure and any of the ring atoms can be optionally substituted. Examples of such saturated or partially unsaturated heterocyclic radicals include, without limitation, tetrahydrofuranyl, tetrahydrothiophenytyl, pyrrolidinyl, pyrrolinyl, tetrahydroquinolinyl, tetrahydroisoquinolinyl, decahydroquinolinyl, oxazolidinyl, piperzinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl-ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

The terms "halogen" and "halo" are used interchangeably to refer to F, Cl, Br, or I.

As used herein, the term "protecting group" refers to a chemical moiety that renders a functional group unreactive, but is also removable so as to restore the functional group. Examples of "alcohol protecting groups" include, but are not limited to, benzyl; tert-butyl; trityl; tert-butyldimethylsilyl (TBDMS; TBS); 4,5-dimethoxy-2-nitrobenzyloxycarbonyl (Dmnb); propargyloxycarbonyl (Poc); and the like. Examples of "amine protecting groups" include, but are not limited to benzyloxycarbontyl; 9-fluorenylmethyloxycarbonyl (Fmoc); tert-butyloxycarbonyl (Boc); allyloxycarbonyl (Alloc); p-toluene sulfonyl (Tos); 2,2,5,7,8-pentamethylchroman-6-fulfonyl (Pmc); 2,2,4,6,7-pentamethyl-2,3-dihydrobenzofuran-5-sulfonyl (Pbf); mesityl-2-sulfonyl (Mts); 4-methoxy-2,3,6-trimethylphenylsulfonyl (Mtr); acetamido; phthalimido; and the like. Other alcohol protecting groups and amine protecting groups are known to those of skill in the an including, for example, those described by Green and Wuts (*Protective Groups in Organic Synthesis,* 4*th Ed.* 2007, Wiley-Interscience, N.Y.).

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are generally those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; $—(CH_2)_{0-4}R^{\alpha}$; $—(CH_2)_{0-4}OR^{\alpha}$; $—O(CH_2)_{0-4}R^{\alpha}$; $—O—(CH_2)_{0-4}C(O)OR^{\alpha}$; $—(CH_2)_{0-4}CH(OR^{\alpha})_2$; $—(CH_2)_{0-4}SR^{\alpha}$; $—(CH_2)_{0-4}Ph$, which may be substituted with $R^{\alpha}$, $—(CH_2)_{0-4}O(CH_2)_{0-1}Ph$ which may be substituted with $R^{\alpha}$; —CH═CHPh, which may be substituted with $R^{\alpha}$; $—(CH_2)_{0-4}O(CH_2)_{0-1}$-pyridyl which may be substituted with $R^{\alpha}$; $—NO_2$; —CN; $—N_3$; $—(CH_2)_{0-4}N(R^{\alpha})_2$; $—(CH_2)_{0-4}N(R^{\alpha})C(O)R^{\alpha}$; $—N(R^{\alpha})C(S)R^{\alpha}$; $—(CH_2)_{0-4}N(R^{\alpha})C(O)NR^{\alpha}_2$; $—N(R^{\alpha})C(S)NR^{\alpha}_2$; $—(CH_2)_{0-4}N(R^{\alpha})C(O)OR^{\alpha}$; $—N(R^{\alpha})N(R^{\alpha})C(O)R^{\alpha}$; $—N(R^{\alpha})N(R^{\alpha})C(O)NR^{\alpha}_2$; $—N(R^{\alpha})N(R^{\alpha})C(O)OR^{\alpha}$; $—(CH_2)_{0-4}C(O)R^{\alpha}$; $—C(S)R^{\alpha}$; $—(CH_2)_{0-4}C(O)OR^{\alpha}$; $—(CH_2)_{0-4}C(O)SR^{\alpha}$; $—CH_2)_{0-4}C(O)OSiR^{\alpha}_3$; $—(CH_2)_{0-4}OC(O)R^{\alpha}$; $—OC(O)(CH_2)_{0-4}SR—SC(S)SR^{\alpha}$; $—(CH_2)_{0-4}SC(O)R^{\alpha}$; $—(CH_2)_{0-4}C(O)NR^{\alpha}_2$; $—C(S)NR^{\alpha}_2$, $—C(S)SR^{\alpha}$; $—SC(S)SR^{\alpha}$, $—(CH_2)_{0-4}OC(O)NR^{\alpha}_2$; $—C(O)C(O)R^{\alpha}$; $—C(O)CH_2C(O)R^{\alpha}$; $—C(NOR^{\alpha})R^{\alpha}$; $—(CH_2)_{0-4}SSR^{\alpha}$; $—(CH_2)_{0-4}S(O)_2R^{\alpha}$; $—(CH_2)_{0-4}S(O)_2OR^{\alpha}$; $—(CH_2)_{0-4}OS(O)_2R^{\alpha}$; $—S(O)_2NR^{\alpha}_2$; $—(CH_2)_{0-4}S(O)R^{\alpha}$; $—N(R^{\alpha})S(O)_2NR^2_2$; $—N(R^{\alpha})\ S(O)_2R^{\alpha}$; $—N(OR^{\alpha})R^{\alpha}$; $—C(NH)NR^{\alpha}_2$; $—P(O)R^{\alpha}_2$; $—OP(O)R^{\alpha}_2$; $—OP(O)(OR^{\alpha})_2$; $SiR^{\alpha}_3$; $—(C_{1-4}$ straight or branched)alkylene)O—$N(R^{\alpha})_2$; or $—(C_{1-4}$ straight or branched)alkylene)C(O)O—$N(R^{\alpha})_2$, wherein each $R^{\alpha}$ may be substituted as defined below a is independently hydrogen, $C_{1-6}$ aliphatic, $—CH_2Ph$, $—O(CH_2)_{0-1}Ph$, $—CH_2$—(5-6 membered heteroaryl ring), or a 5-6-membered saturated, partially unsaturated, or aromatic ring having 0-4 heteroatoms independently selected from nitrogen, oxygen, and sulfur, or, notwithstanding the definition above, two independent occurrences of $R^{\alpha}$, taken together with their intervening atom(s), form a 3-12-membered saturated, partially unsaturated, or aromatic mono- or bi-cyclic ring having 0-4 heteroatoms independently selected from nitrogen, oxygen, and sulfur, which may be substituted as defined below.

Suitable monovalent substituents on $R^{\alpha}$ (or the ring formed by taking two independent occurrences of $R^{\alpha}$ together with their intervening atoms), are independently halogen, $—(CH_2)_{0-2}R^{\beta}$; -(halo$R^{\beta}$); $—(CH_2)_{0-2}OH$; $—(CH_2)_{0-2}OR^{\beta}$; $—(CH_2)_{0-2}CH(OR^{\beta})_2$; —O(halo$R^{\beta}$); —CN; $—N_3$; $—(CH_2)_{0-2}C(O)R^{\beta}$; $—(CH_2)_{0-2}C(O)OH$; $—(CH_2)_{0-2}C(O)OR^{\beta}$; $—(CH_2)_{0-2}SR^{\beta}$; $—(CH_2)_{0-2}SH$; $—(CH_2)_{0-2}NHR^{\beta}$; $—(CH_2)_{0-2}NR^{\beta}_2$; $—NO_2$; $SiR^{\beta}_3$; $—OSiR^{\beta}_3$; $—C(O)SR^{\beta}$; $—(C_{1-4}$ straight or branched alkylene)$C(O)OR^{\beta}$; or $—SSR^{\beta}$; wherein each $R^{\beta}$ is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aromatic ring having 0-4 heteroatoms independently selected from nitrogen, oxygen, and sulfur. Suitable divalent substituents on a saturated carbon atom of $R^{\alpha}$ include ═O and ═S.

Suitable divalent substituents on a saturated carbon atom of an "optionally substituted" group include the following: ═O; ═S; $═NNR^{\gamma}_2$; $═NNHC(O)R^{\gamma}$; $═NNHC(O)OR^{\gamma}$; $═NNHS(O)_2R^{\gamma}$; $═NR^{\gamma}$; $═NOR^{\gamma}$; $—O(C(R^{\gamma}_2))_{2-3}O—$; or $—S(C(R^{\gamma}_2))_{2-3}S—$; wherein each independent occurrence of $R^{\gamma}$ is selected from hydrogen, $C_{1-6}$ aliphatic which may be substituted as defined below, or an unsubstituted 5-6-membered saturated, partially unsaturated, or aromatic ring having 0-4 heteroatoms independently selected from nitrogen, oxygen, and sulfur. Suitable divalent substituents that are bound to vicinal substitutable carbons of an "optionally substituted" group include: $—O(CR^{\beta}_2)_{2-3}O—$, wherein each independent occurrence of $R^{\beta}$ is selected from hydrogen, $C_{1-6}$ aliphatic which may be substituted as defined below, or an unsubstituted 5-6-membered saturated, partially unsaturated, or aromatic ring having 0-4 heteroatoms independently selected from nitrogen, oxygen, and sulfur.

Suitable substituents on the aliphatic map of $R^{\gamma}$ include halogen, $—R^{\delta}$, -(halo$R^{\delta}$), —OH, $—OR^{\delta}$, —O(halo$R^{\delta}$), —CN, —C(O)OH, $—C(O)OR^{\delta}$, $—NH_2$, $—NHR^{\delta}$, $—NR^{\delta}_2$, or $—NO_2$, wherein each $R^{\delta}$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aromatic ring having 0-4 heteroatoms independently selected from nitrogen, oxygen, and sulfur.

Suitable substituents on a substitutable nitrogen of an "optionally substituted" group include $—R^{\varepsilon}$, $—NR^{\varepsilon}_2$, $—C(O)R^{6}$, $—C(O)C(O)R^{\varepsilon}$, $—C(O)CH_2C(O)R^{\varepsilon}$, $—S(O)_2R^{\varepsilon}$, $—S(O)_2NR^{\varepsilon}_2$, $—C(S)NR^{\varepsilon}_2$, $—C(NH)NR^{\varepsilon}_2$, or $—N(R^{\varepsilon})S(O)_2R^{\varepsilon}$; wherein each $R^{\varepsilon}$ is independently hydrogen, $C_{1-6}$ aliphatic which may be substituted as defined below, unsubstinned —OPh, or an unsubstituted 5-6-membered saturated, partially unsaturated, or aromatic ring having 0-4 heteroatoms independently selected from nitrogen, oxygen, and sulfur, or, notwithstanding the definition above, two independent occurrences of $R^{\varepsilon}$ taken together with their intervening atom(s) form an unsubstituted 3-12-membered saturated, partially unsaturated, or aromatic mono- or bicyclic ring having 0-4 heteroatoms independently selected from nitrogen, oxygen, and sulfur.

Suitable substituents on the aliphatic group of $R^{\varepsilon}$ are independently halogen, $—R^{\delta}$, -(halo$R^{\delta}$), —OH, $—OR^{\delta}$, —CN, $—C(O)OR^{\delta}$, $—NH_2$, $—NHR^{\delta}$, $—NR^{\delta}_2$, or $—NO_2$, wherein each $R^{\delta}$ is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, of aromatic ring having 0-4 heteroatoms independently selected from nitrogen, oxygen, and sulfur.

In some embodiments, the term "substituted" is contemplated to include all permissible substituents of organic compounds, "permissible" being in the context of the chemical rules of valence known to those of ordinary skill in the art. In some cases, "substituted" may generally refer to replacement of a hydrogen atom with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" group must still comprise the phenyl moiety and cannot be modified by substitution, in this definition, to become, e.g., cyclohexyl group. In a broad aspect, permissible substituents include acyclic and cyclic, branched and unbranched, carbocyclic and heterocyclic, aromatic and nonaromatic substituents of organic compounds. Illustrative substituents include, for example, those described herein. Permissible substituents can be one or more and the same or different for appropriate organic compounds. For example, a substituted alkyl group may be $CF_3$. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, arylalkyl, cyclic alkyl, heterocycloalkyl, hydroxy, alkoxy, aryloxy, perhaloalkoxy, arylalkoxy, heteroaryl, heteroaryloxy heteroarylalkyl heteroarylalkoxy, azido amino, halogen, alkylthio oxo, acylalkyl, carboxy esters, carboxyl, carboxamido, nitro, acyloxy, aminoalkyl, alkylaminoaryl, alkylaryl alkylaminoalkyl, alkoxyaryl, arylamino, arylalkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl and the like.

As used herein, the term "natural oil" refers to an oil derived from a plant or animal source. The term "natural oil" includes natural oil derivatives, unless otherwise indicated. The plant or animol sources can be modified plant or animol sources (e.g., genetically modified plant or animol sources), unless indicated otherwise. Examples of natural oils include, but are not limited to, vegetable oils, algae oils, fish oils, animol fats, tall oils, derivatives of these oils, combinations of any of these oils, and the like.

The term "vegetable oils" refers to the natural oil or natural oil derivatives from any suitable component of a plant (e.g., vegetable, fruit, leaf, stem, shrub, flower, seed, or tree nut) or any combination thereof. Representative non-limiting examples of vegetable oils include almond oil, canola oil, avocado oil, argan oil, rapeseed oil, coconut oil, corn oil, cottonseed oil, grape seed oil, olive oil, palm oil, peanut oil, hemp oil, macadamia oil, safflower oil, sesame oil, soybean oil, sunflower oil, linseed oil, palm kernel oil, tung oil, jatropha oil, jojoba oil, mustard oil, pennycress oil, camelina oil, and castor oil. Representative non-limiting examples of animol fats include lard, tallow, poultry fat, yellow grease, and fish oil. Tall oils are by-products of wood pulp manufacture. "Natural seed oil" refers to a type of natural vegetable oil that is obtained specifically from the seeds of the plant, rather than the fruit (or other component) of the plant. Accordingly, not all vegetable oils are seed oils. For example, olive oil and peanut oil are not natural seed oils. Representative non-limiting examples of natural seed oils include almond oil, canola oil, avocado oil, argan oil, rapeseed oil, coconut oil, corn oil, cottonseed oil, grape seed oil, hemp oil, macadamia oil, safflower oil, sesame oil, soybean oil, sunflower oil, linseed oil, palm kernel oil, tung oil, jatropha oil, jojoba oil, mustard oil, pennycress oil, camelina oil, and castor oil.

"Natural oil derivatives" refer to compounds (or mixtures of compounds) derived from natural oils using any one or combination of methods known in the art. Such methods include but are not limited to saponification, fat splitting, transesterification, esterification, hydrogenation (partial or full), isomerization, oxidation, reduction, and metathesis. Representative non-limiting examples of natural oil derivatives include gums, phospholipids, soapstock, acidulated soapstock, distillate or distillate sludge, natty acids, and fatty acid alkyl esters (e.g., non-limiting examples such as 2-ethylhexyl ester), and hydroxy substituted variations thereof. For example, the natural oil derivative may be a fatty acid methyl ester ("FAME") derived from the glyceride of the natural oil.

The term "contaminant" refers broadly and without limitation to any impurity, regardless of the amount in which it is present, admixed with a substrate to be used in olefin metathesis. A "catalyst poisoning contaminant" refers to a contaminant having the potential to adversely affect the performance of a metathesis catalyst. Examples of catalyst poisoning contaminants include, but are not limited to, water, peroxides, and hydroperoxides.

III. Methods for Synthesizing Fatty Olefin Metathesis Products

In some embodiments, the invention provides a method for synthesizing a Z-enriched fatty olefin metathesis product, the method comprising contacting an olefin metathesis reaction partner with an internal olefin in the presence of a group 8 transition metal metathesis catalyst to form the Z-enriched fatty olefin metathesis product, wherein:

the fatty olefin metathesis product is an acylated alkenol or an alkenal acetal, the olefin metathesis reaction partner comprises a mixture of Z olefins and E olefins in a starting Z:E ratio, the fatty olefin metathesis product comprises a mixture of Z olefins and E olefins in a product Z:E ratio, and the product Z:E ratio is higher than the start nm Z:E ratio.

The methods of the invention are highLy Z-selective, wherein more than 80% of the formed metathesis products are in the Z-configuration. More specifically, the methods of the present invention produce fatty olefin metathesis products, e.g., compounds of Formula I, that are at least 97% Z. Furthermore, the present invention provides methods for producing a fatty olefin metathesis product of high Z-isomeric purity from olefin feedstocks of low Z-isomeric purity.

In some embodiments, methods for synthesizing a fatty olefin metathesis product according to Formula I are provided.

(I)

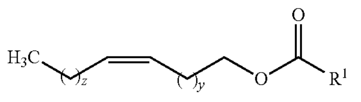

The methods include contacting an olefin metathesis reaction partner according to Formula III (III)

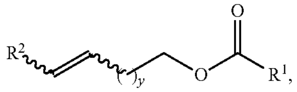

with an internal olefin according to Formula IV (IV)

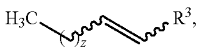

in the presence of a metathesis catalyst to form the fatty olefin metathesis product; wherein:

$R^1$ is selected from the group consisting of H and $C_{1-6}$ alkyl;

$R^2$ is selected from the group consisting of $C_{1-18}$ alkyl and $C_{2-18}$ alkenyl;

$R^3$ $C_{1-18}$ alkyl;

subscript y is an integer ranging from 0 to 17;

subscript z is an integer ranging from 0 to 17; and the metathesis catalyst is a Z-selective group 8 transition metal catalyst.

In some embodiments, the fatty olefin metathesis pr duct is an alkenal acetal of Formula VI:

(VI)

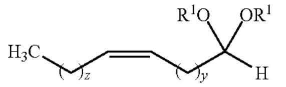

the metathesis reaction partner is a compound of Formula VII:

(VII)

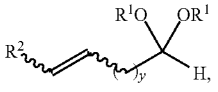

the internal olefin is a compound or Formula IV (IV)

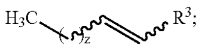

$R^1$ is $C_{1-6}$ alkyl;

$R^2$ is selected from the group consisting of $C_{1-18}$ alkyl and $C_{2-18}$ alkenyl;

$R^3$ is $C_{1-18}$ alkyl;

subscript y is an integer ranging from 0 to 17;

subscript z is an integer ranging from 0 to 17; and the group 8 transition metal metathesis catalyst is a Z-selective group 8 transition metal catalyst.

Metathesis of Fatty Olefin Derivatives

In some embodiments, the method for synthesizing the fatty olefin metathesis product according to Formula I (I)

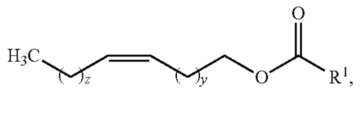

comprises contacting an olefin metathesis reaction partner according to Formula III (III)

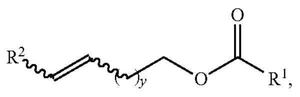

with an internal olefin according to Formula IV (IV)

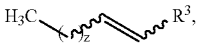

in the presence of a Z-selective group 8 transition metal catalyst metathesis catalyst (e.g., Z-selecfive ruthenium catalyst or a Z-selective osmium catalyst) to form the fatty olefin metathesis product wherein:

$R^1$ is selected from the group consisting of H and $C_{1-6}$ alkyl;

$R^2$ is selected from the group consisting of $C_{1-18}$ alkyl and $C_{2-18}$ alkenyl;

$R^3$ is $C_{1-18}$ alkyl;

subscript y is an integer ranging from 0 to 17, and subscript z is an integer ranging from 0 to 17.

In some embodiments, the method for synthesizing the fatty olefin metathesis product of Formula I further comprises forming the olefin metathesis reaction partner of Formula III by contacting an acylating agent with an alkenol according to Formula II (II)

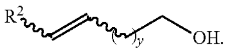

In some embodiments, the acylating agent used to contact the alkenol of Formula II to form the olefin metathesis reaction partner of Formula III is acetic anhydride.

Any acylating agent suitable for forming the olefin metathesis reaction partner of Formula III can be used in the methods of the invention. Examples of suitable acylating agents include acid anhydrides (e.g., acetic anhydride), acid chlorides e.g., acetyl chloride), activated esters (e.g., pentafluorophenyl esters of carboxylic acids), and carboxylic acids used with coupling agents such as dicyclohexylcarbodiimide or carbonyl diimidazole. Typically, 1-10 molar equivalents of the acylating agent with respect to the alkenol will be used. For example, 1-5 molar equivalents of the acylating agent or 1-2 molar equivalents of the acylating agent can be used. In some embodiments, around 1.0, 1.1, 1.2, 1.3, 1.4, or 1.5 molar equivalents of the acylating agent (e.g., acetic anhydride) with respect to the alkenol is used to form the olefin metathesis reaction partner of Formula III.

A base can be used to promote acylation of the alkenol by the acylating agent. Examples of suitable bases include potassium carbonate, sodium carbonate, sodium acetate, Huenig's base (i.e., N,N-diisopropylethylamine), lutidines including 2,6-lutidine (i.e., 2,6-dimethylpyridine), triethylamine, tributylamine, pyridine, 2,6-di-tert-butylpyridine, 1,8-diazabicycloundec-Z-ene (DBU), quinuclidine, and the collidines. Combinations of two or more bases can be used. Typically, less than one molar equivalent of base with respect to the alkenol will be employed in the methods of the invention. For example, 0.05-0.9 molar equivalents or 0.1-0.5 molar equivalents of the base can be used. In some embodiments, around 0.05, 0.1, 0.15, or 0.2 molar equivalents of the base (e.g., sodium acetate) with respect to the alkenol is used in conjunction with the acylating agent: (e.g., acetic anhydride) to form the olefin metathesis reaction partner of Formula III.

Any suitable solvent can be used for acylating the alkenol. Suitable solvents include, but are not limited to, toluene, methylene chloride, ethyl acetate, acetonitrile, tetrahydrofuran, benzene, chloroform, diethyl ether, dimethyl formamide, dimethyl sulfoxide, petroleum ether, and mixtures thereof. Alternatively, an alkenol such as (Z)-octadec-9-en-1-ol (i.e., oleyl alcohol) can be combined with an acylating agent such as acetic anhydride and a base such as sodium acetate without an additional solvent. The acylation reaction is typically conducted at temperatures ranging from around 25° C. to about 100° C. for a period of time sufficient to form the olefin metathesis reaction partner of Formula III. The reaction can be conducted for a period of time ranging from a few minutes to several hours or longer, depending on the particular alkenol and acylating agent used in the reaction. For example, the reaction can be conducted for around 10 minutes, or around 30 minutes, or around 1 hour, or around 2 hours, or around 4 hours, or around 8 hours, or around 12 hours at around 40° C., or around 50° C., or around 60° C. or around 70° C., or around 80° C.

Accordingly, in some embodiments, the invention provides a method for synthesizing a fatty olefin metathesis product according to Formula I:

(I)

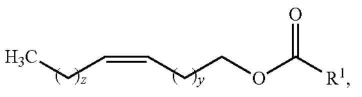

wherein the method includes contacting an acylating agent with an alkenol according to Formula II (II)

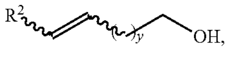

to form an olefin metathesis reaction partner according to Formula III (III)

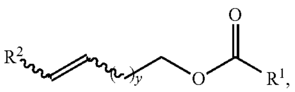

and contacting the olefin metathesis reaction partner with an internal olefin according to Formula IV (IV)

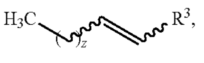

in the presence of a Z-selective ruthenium catalyst or a Z-selective osmium catalyst to form the fatty olefin metathesis product; wherein:

$R^1$ is selected from the group consisting of H and $C_{1-6}$ alkyl;

$R^2$ is selected from the group consisting of $C_{1-18}$ alkyl and $C^{2-18}$ is alkenyl;

$R^3$ is $C_{1-18}$ alkyl;

subscript y is an integer ranging from 0 to 17; and subscript z is an integer ranging from 0 to 17.

In some embodiments, the method for synthesizing the fatty olefin metathesis product further includes arming the alkenol of Formula II by reducing an unsaturated fatty carboxyl derivative according to Formula IIa (IIa)

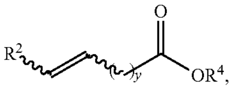

wherein $R^4$ is selected from the group consisting of H and $C_{1-18}$ alkyl.

In some embodiments, forming the alkenol of Formula II comprises contacting the unsaturated fatty carboxyl derivative of Formula IIa with a base in the presence of a hydrogenation catalyst and hydrogen gas. Homogenous or heterogenous conditions can be used. Examples of homogenous conditions include, but are not limited to: hydrogenolysis using ligated transition metal catalysts (Werkmeister, S. et al. *Org. Process Res. Dev.* 2014, 18, 289-302; Tan, et al. *Org. Lett.* 2015, 17 (3), 454; Spasyuk. D. et al. *J. Am. Chem. Soc.* 2015, 137, 3743; WO 2014/139030) and metal hydride-catalyzed reduction using silane reagents (Mimoun, H. *J. Org. Chem.* 1999, 64, 2582; U.S. Pat. No. 6,533,960). Examples of heterogeneous conditions include, but are not limited to, hydrogenolysis of the unsaturated fatty carboxyl derivative of Formula IIa using ZnO or CuO/ZnO supported on chromite, alumina, or other material to form the alkenol of Formula II. Any suitable combination of conditions for reducing the unsaturated fatty carboxyl derivative of Formula IIa to the alkenol of Formula II can be used in the methods of the invention.

In some embodiments, the hydrogenation catalyst used for forming the alkenol of Formula II from the unsaturated fatty carboxyl derivative of Formula IIa is a homogeneous transition metal catalyst containing pincer-type or tri- or tetradentate ligands. Non-limiting examples of suitable homogenous transition metal catalysts include dichlorotriphenylphosphine[bis(2-(ethylthio)ethyl)amine]ruthenium (II) and dichloro-triphenylphosphine[2-(diphenylphosphino)-N-(2-pyridinylmethyl)ethanamine]ruthenium(II). One of skill in the art be able to select suitable hydrogenation catalysts for reducing the unsaturated fatty carboxyl derivative (e.g., an alkyl ester-containing compound) to the corresponding alkenol (e.g., alcohol-containing compound). Other homogeneous transition metal catalysts suitable for hydrogenating an alkyl ester group to an alcohol group are known to those of skill in the art including, for example, those described in Werkmeister, S. et al. *Org. Process Res. Dev.* 2014, 18, 289-302. Typically, the hydrogenation catalyst is used in a sub-stoichiometric amount (e.g. catalytic amount) in the presence of hydrogen gas and a suitable base, such as, for example, sodium ethoxide, sodium methoxide, sodium tert-butoxide, etc. In some embodiments, forming the alkenol of Formula II comprises contacting the unsaturated fatty carboxyl derivative of Formula IIa with a base in the presence of a hydrogenation catalyst and hydrogen gas, wherein the unsaturated fatty carboxyl derivative is an unsaturated fatty acid alkyl ester. In some embodiments, forming the alkenol of Formula II comprises contacting the unsaturated fatty carboxyl derivative of Formula IIa with a base in the presence of a hydrogenation catalyst and hydrogen gas, wherein $R^4$ of Formula IIa is $C_{1-8}$ alkyl.

In some embodiments, forming the alkenol of Formula II comprises contacting the unsaturated fatty carboxyl derivative of Formula IIa with a reducing agent. Any suitable reducing agent can be used for reducing the unsaturated fatty carboxyl derivative of Formula IIa in to the alkenol of Formula II, such as sodium borohydride, sodium triacetoxyborohydride, sodium cyanoborohydride, lithium aluminum hydride, diisobutyl aluminum hydride (CN 103319704 Chandrasekhar, et al. *Tetrahedron Lett.* 1998, 39, 909), and sodium bis(2-methoxyethoxy)aluminum hydride ("SMEAH"; also known by trade names RED-AL, SYNHYDRIDE, and VITRIDE). In some embodiments, the reducing agent is sodium bis(2-methoxyethoxy)aluminumhydride.

Typically, 1-2 molar equivalents of the reducing agent with respect to the unsaturated fatty carboxyl derivative will be used. In some embodiments, around 1.0, 1.1, 1.2, 1.3, 1.4, or 1.5 molar equivalents of the reducing agent with respect to the unsaturated fatty carboxyl derivative is used to form the corresponding alkenol. In some embodiments, forming the alkenol of Formula II comprises contacting the unsaturated fatty carboxyl derivative of Formula IIa with a reducing agent, wherein the unsaturated fatty carboxyl derivative is an unsaturated fatty acid. In some embodiments, forming the alkenol of Formula II comprises contacting the unsaturated fatty carboxyl derivative of Formula IIa with a reducing agent, wherein $R^4$ of Formula IIa is H. The unsaturated fatty acid reduction reaction is typically conducted at temperatures ranging from around −78° C. to about 25° C. for a period of time sufficient to form the alkenol. The reaction can be conducted for a period of time ranging flow a few minutes to several hours or longer, depending on the particular unsaturated fatty acid and reducing agent used in the reaction. For example, the reduction of (Z)-icos-11-enoic acid with an aluminum reagent (e.g. sodium bis(2-methoxyethoxy)-oluminumhydride) can be conducted for 1-2 hours at a temperature ranging from around 0° C. to around 2° C.

Any suitable solvent can be used for reducing the unsaturated fatty carboxyl derivative of Formula IIa (e.g., base with hydrogenation catalyst and hydrogen gas or reducing agent). Suitable solvents include, but are not limited to, toluene, methylene chloride, ethyl acetate, acetonitrile, tetrahydrofuran, benzene, chloroform, diethyl ether, dimethyl formamide, dimethyl sulfoxide, petroleum ether, and mixtures thereof.

Accordingly, in some embodiments, the invention provides a method for synthesizing a fatty olefin metathesis product according to Formula I:

(I)

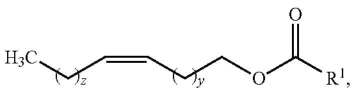

wherein the method includes reducing an unsaturated fatty carboxyl derivative according to Formula IIa (IIa)

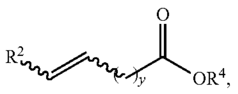

to form an alkenol according to Formula II (II)

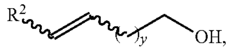

contacting an acylating agent with the alkenol to form an olefin metathesis reaction partner according to Formula III (III)

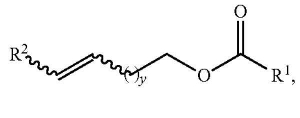

and contacting the olefin metathesis reaction partner with an internal olefin according to Formula IV (IV)

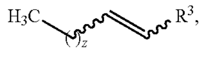

in the presence of a Z-selective ruthenium catalyst or a Z-selective osmium catalyst to form the fatty olefin metathesis product; wherein:

$R^1$ is selected from the group consisting of H and $C_{1-6}$ alkyl;

$R^2$ is selected from the group consisting of $C_{1-18}$ alkyl and $C_{2-18}$ alkenyl;

$R^3$ is $C_{1-18}$ alkyl;

$R^4$ is selected from the group consisting of H and $C_{1-8}$ alkyl;

subscript y is an integer ranging from 0 to 17; and subscript z is an integer ranging from 0 to 17.

In some embodiments, synthesizing the fatty olefin metathesis product of Formula I according to any of the methods described herein optionally further comprises contacting the olefin metathesis reaction partner of Formula III with a pretreatment reagent prior to contacting the olefin metathesis reaction partner with the olefin. In some embodiments, the pretreatment reagent is selected from the group consisting of alumina and magnesium aluminum isopropoxide. In some embodiments, the pretreatment reagent is alumina. In some embodiments, the pretreatment reagent is magnesium aluminum isopropoxide.

In some embodiments, $R^1$ of Formula I and Formula III is selected from the group consisting of H and $C_{1-6}$ alkyl. In some embodiments, $R^1$ is H. In some embodiments, $R^1$ as $C_{1-6}$ alkyl. In some embodiments, $R^1$ is selected from the group consisting of methyl, ethyl, n-propyl, isopropyl, n-butyl, 2-butyl, isobutyl, tert-butyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, and 1-ethyl-2-methylpropyl. In some embodiments, $R^1$ is selected from the group consisting of methyl, ethyl, n-propyl, n-butyl, n-pentyl, and n-hexyl. In some embodiments, $R^1$ is selected from the group consisting of H and $C_{1-3}$ alkyl. In some embodiments, $R^1$ is selected from the group consisting of H, methyl, ethyl, and propyl. In some embodiments, $R^1$ is selected from the group consisting of H, methyl, and ethyl. In some embodiments, $R^1$ is selected from the group consisting of H and methyl. In some embodiments, $R^1$ is methyl.

In some embodiments, $R^2$ of Formula IIa, Formula II, and Formula III is selected from the group consisting of $C_{1-18}$ alkyl and $C_{2-18}$ alkenyl. In some embodiments, $R^2$ is $C_{1-18}$ alkyl. In some embodiments, $R^2$ is $C_{2-18}$ alkenyl. In some embodiments, $R^2$ s selected from the roup consisting of $C_{1-18}$ alkyl, $C_{2-18}$ alkyl, $C_{3-18}$ alkyl, $C_{4-18}$ alkyl, $C_{5-18}$ alkyl, $C_{6-18}$ alkyl, $C_{7-18}$ alkyl, $C_{8-18}$ alkyl, $C_{9-18}$ alkyl, $C_{10-18}$ alkyl, $C_{11-18}$ alkyl, $C_{12-18}$ alkyl, $C_{13-18}$ alkyl, $C_{14-18}$ alkyl, $C_{15-18}$ alkyl, $C_{16-18}$ alkyl, and $C_{17-18}$ alkyl. In some embodiments, $R^2$ is selected from the group consisting of $C_{2-18}$ alkenyl, $C_{3-18}$ alkenyl, $C_{4-18}$ alkenyl, $C_{5-18}$ alkenyl, $C_{6-18}$ alkenyl, $C_{7-18}$ alkenyl, $C_{8-18}$ alkenyl, $C_{9-18}$ alkenyl, $C_{10-18}$ alkenyl, $C_{11-18}$ alkenyl, $C_{12-18}$ alkenyl, $C_{13-18}$ alkenyl, $C_{14-18}$ alkenyl, $C_{15-18}$ alkenyl, $C_{16-18}$ alkenyl, and $C_{17-18}$ alkenyl. In some embodiments, $R^2$ is linear $C_{1-18}$ alkyl selected from the group consisting of methyl, ethyl, propyl, butyl, pentyl, hexyl heptyl, octyl, nonyl, decyl, undecyl, dodecyl, tridecyl, tetradecyl, pentadecyl, hexadecyl, heptadecyl, and octadecyl. In some embodiments, $R^2$ is linear $C_{2-18}$ alkenyl having a carbon-carbon double bond at any position within the hydrocarbon chain, wherein $C_{2-18}$ alkenyl is selected from the group consisting of the selected from the group consisting of vinyl, propenyl, n-butenyl, n-pentenyl, n-hexenyl, n-heptenyl, n-octenyl, n-nonenyl, n-decenyl, n-undecenyl, n-dodecenyl, n-tridecenyl, n-tetradecenyl, n-pentadecenyl, n-hexadecenyl, n-heptadecenyl, and n-octadecenyl.

In some embodiments. $R^2$ of Formula IIa, Formula II, and Formula III is selected from the group consisting of $C_{1-12}$ alkyl and $C_{2-12}$ alkenyl. In some embodiments, $R^2$ is selected from the group consisting of methyl, ethyl, n-propy, n-butyl, n-pentyl, n-hexyl, n-heptyl, n-octyl, n-nonyl, n-decyl, n-undecyl, n-dodecyl, propenyl, n-butenyl, n-pentenyl, n-hexenyl, n-heptenyl, n-octenyl, n-nonenyl, n-decenyl, n-undecenyl, and n-dodecenyl. In some embodiments, $R^2$ is $C_{1-12}$ alkyl. In some embodiments, $R^2$ is selected from the group consisting of methyl, ethyl, n-propyl, n-butyl, n-pentyl, n-hexyl, n-heptyl, n-octyl, n-nonyl, n-decyl, n-undecyl, and n-dodecyl. In some embodiments, $R^2$ is selected from the group consisting of n-butyl, n-pentyl, n-hexyl, n-heptyl, n-octyl, n-nonyl, and n-decyl. In some embodiments, $R^2$ is selected from the group consisting of n-pentyl, n-hexyl, n-heptyl, n-octyl, and n-nonyl. In some embodiments, $R^2$ is selected from the group consisting of n-hexyl, n-heptyl, and n-octyl. In some embodiments, $R^2$ is n-octyl. In some embodiments, $R^2$ is not H.

In some embodiments, $R^3$ of Formula III is $C_{1-18}$ alkyl. In some embodiments, $R^3$ is selected from the group consisting of $C_{1-18}$ alkyl, $C_{1-17}$ alkyl, $C_{1-16}$ alkyl, $C_{1-15}$ alkyl, $C_{1-14}$ alkyl, $C_{1-13}$ alkyl, $C_{1-12}$ alkyl, $C_{1-11}$ alkyl, $C_{1-10}$ alkyl, $C_{1-9}$ alkyl, $C_{1-8}$ alkyl, $C_{1-7}$ alkyl, $C_{1-6}$ alkyl, $C_{1-5}$ alkyl, $C_{1-4}$ alkyl, $C_{1-3}$ alkyl, and $C_{1-2}$ alkyl. In some embodiments, $R^3$ is linear. $C_{1-18}$ alkyl selected from the group consisting of methyl, ethyl, propyl, butyl, pentyl, hexyl heptyl, octyl, nonyl, decyl, undecyl, dodecyl, tridecyl, tetradecyl, pentadecyl, hexadecyl, heptadecyl, and octadecyl. In some embodiments, $R^3$ is $C_{1-12}$ alkyl. In some embodiments, $R^3$ is selected from the group consisting of methyl, ethyl, n-propyl, n-butyl, n-pentyl, n-hexyl, n-heptyl: n-octyl, n-nonyl, n-decyl, n-undecyl, and n-dodecyl. In some embodiments, selected from the group consisting of methyl, ethyl, n-propyl, n-butyl, n-pentyl, n-hexyl, n-heptyl, and n-octyl. In some embodiments, $R^3$ is selected from the group consisting of methyl, ethyl, n-propyl, n-pentyl, n-hexyl, and n-heptyl. In some embodiments, $R^3$ is selected from the group consisting of ethyl, n-propyl, n-butyl, n-pentyl, and n-hexyl. In some embodiments, $R^3$ is n-butyl. In some embodiments, $R^3$ is n-propyl. In some embodiments, $R^3$ is ethyl. In some embodiments, $R^3$ is not H.

In some embodiments, $R^4$ of Formula IIa is selected from the group consisting of H and $C_{1-8}$ alkyl. In some embodiments, $R^4$ is H. In some embodiments, $R^4$ is $C_{1-8}$ alkyl. In some embodiments, $R^4$ is selected from the group consisting of methyl, ethyl, n-propyl, isopropyl, n-butyl, 2-butyl, isobutyl, tert-butyl, pentyl, 1-methylbutyl, 2-methylbutyl, 3-methylbutyl, 2,2-dimethylpropyls, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,3-dimethylbutyl, 2,2-dimethylbutyl, 2,3-dimethylbutyl 3,3-dimethylbutyl, 1-ethylbutyl, 2-ethylbutyl, 1,2-trimethylpropyl, 1,2,2-trimethylpropyl, 1-ethyl-1-methylpropyl, 1-ethyl-2-methylpropyl, heptyl and octyl. In some embodiments, $R^4$ is selected from the group consisting of methyl, ethyl, n-propyl, n-butyl, n-pentyl, n-hexyl, n-heptyl, and n-octyl. In some embodiments, $R^4$ is selected from the group consisting of H and $C_{1-3}$ alkyl. In some embodiments, $R^4$ is selected from the group consisting of H, methyl, ethyl, and propyl. In some embodiments, $R^4$ is selected from the group consisting of H, methyl, and ethyl. In some embodiments, $R^4$ is selected from the group consisting of H and methyl. In some embodiments, $R^4$ is H. In some embodiments, $R^4$ is methyl. When $R^4$ is H, the unsaturated fatty carbonyl derivative of Formula IIa is an unsaturated fatty acid. When $R^4$ is $C_{1-8}$ alkyl or $C_{1-3}$ alkyl, the unsaturated fatty carboxyl derivative of Formula IIa is an unsaturated fatty acid alkyl ester.

In some embodiments, subscript y of Formula I, Formula IIa, Formula II, and Formula III is an integer ranging from 0 to 17. In some embodiments, subscript y is 0, 1, 2, 3, 4, 5, 6, 7, 8, 9, 10, 11, 12, 13, 14, 15, 16, or 17. In some embodiments, subscript y is 1, 2, 3, 4, 5, 6, 7, 8, 9, 10, 11, 12, 13, 14, 15, or 16. In some embodiments, subscript y is 2, 3, 4, 5, 6, 7, 8, 9, 10, 11, 12, 13, 14, or 15. In some embodiments, subscript y is an integer ranging from 5 to 15. In some embodiments, subscript y is 5, 6, 7, 8, 9, 10, 11, 12, 13, 14, or 15. In some embodiments, subscript y is 6, 7, 8, 9, 10, 11, 12, or 13. In some embodiments, subscript y is 7, 9, 11, or 13. In some embodiments, subscript y is 7. In some embodiments, subscript y is 9. In some embodiments, subscript z of Formula I and Formula IV is an integer ranging from 0 to 17. In some embodiments, subscript z is 0, 1, 2, 3, 4, 5, 6, 7, 8, 9, 10, 11, 12, 13, 14, 15, 16, or 17. In some embodiments, subscript z is 0, 1, 2, 3, 4, 5, 6, 7, 8, 9, 10, 11, 12, 13, or 14. In some embodiments, subscript z is an integer ranging from 0 to 7. In some embodiments, subscript z is 0, 1, 2, 3, 4, 5, 6, or 7. In some embodiments, subscript z is an integer ranging from 0 to 5. In some embodiments, subscript z is 0, 1, 2, 3, 4, or 5. In some embodiments, subscript z is 1, 2, 3, or 4. In some embodiments, subscript z is 1. In some embodiments, subscript z is. In some embodiments, subscript z is 3.

In some embodiments, the methods described herein are used to prepare a fatty olefin metathesis product according to Formual I, wherein y is 0 and z is 4; or y is 1 and z is 3; or y is 3 and z is 1; y is 4 and z is 0; or y is 0 and z is 5; or y is 1 and z is 4; or y is 2 and z is 3; or y is 3 and z is 2; or y is 4 and z is 1; or y is 5 and z is 0; or y is 0 and z is 6; or y is 1 and z is 5; or y is 2 and z is 4; or y is 4 and z is 2; or y is 5 and z is 1; or y is 6 and z is 0; or y is 0 and z is 7; or y is 1 and z is 6; y is 2 and z is 5; or y is 3 and z is 4; or y is 4 and z is 3; or y is 5 and z is 2; or y is 6 and z is 1; or y is 7 and z is 0; or y is 0 and z is 8; or y is 1 and z is 7; or y is 2 and z is 6; or y is 3 and z is 5; or y is 5 and z is 3; or y is 6 and z is 2; y is 7 and z is 1; or y is 8 and z is 0; or y is 0 and z is 9; or y is 1 and z is 8; or y is 2 and z is 7; or y is 3 and z is 6; or y is 4 and z is 5; or y is 5 and z is 4; or y is 6 and z is 3; or y is 7 and z is 2; or y is 8 and z is 1; or y is 9 and z is 0; or y is 0 and z is 10; or y is 1 and z is 9; or y is 2 and z is 8; or y is3 and z is 7; or y is 4 and z is 6; or y is 6 and z is 4; or y is 7 and z is 3; or y is 8 and z is 2; or y is 9 and z is 1; y is 10 and z is 0; or y is 0 and z is 11; or y is 1 and z is 10; or y is 2 and z is 9; or y is 3 and z is 8; or y is 4 and z is 7; or y is 5 and z is 6; or y is 6 and z is 5; or y is 7 and z is 4; or y is 8 and z is 3; or y is 9 and z is 2; or y is 10 and z is 1; or y is 11 and z is 0; or y is 0 and z is 12; or y is 1 and z is 11; or y is 2 and z is 10; y is 3 and z is 9; or y is 4 and z is 8; or is 5 and z is 7; or y is 7 and z is 5; or y is 8 and z is 4; or y is 9 and z is 3; or y is 10 and z is 2; or y is 11 and z is 1; or y is 12 and z is 0; or y is 0 and z is 13; or y is 1 and z is 12; or y is 2 and z is 11; or y is 3 and z is 10; y is 4 and z is 9; or y is 5 and z is 8; or y is 6 and z is 7; or y is 7 and z is 6; of y is 8 and z is 5; or y is 9 and z is 4; or y is 10 and z is 3; or y is 11 and z is 2; or y is 12 and z is 1; or y is 13 and z is 0; or y is 0 and z is 14; or y is 1 and z is 13; or y is 2 and z is 12; or y is 3 and z is 11; or y is 4 and z is 10; or y is 5 and z is 9; or y is 6 and z is 8; or y is 8 and z is 6; or y is 9 and z is 5; or y is 10 and z is 4; or y is 11 and z is 3; or y is 12 and z is 2; or y is 13 and z is 1; or y is 14 and z is 0; or y is 0 and z is 15; or y and z is 14; or y is 2 and z is 13; or y is 3 and z is 12; or y is 4 and z is 11; or y is 5 and z is 10; or y is 6 and z is 9; or y is 7 and z is 8; or y is 8 and z is 7; or y is 9 and z is 6; or y is 10 and z is 5; or y is 11 and z is 4; or y is 12 and z is 3; or y is 13 and z is 2; or y is 14 and z is 1; or y is 15 and z is 0; or y is 0 and z is 16; or y is 1 and z is 15; or y is 2 and z is 14; or y is 3 and z is 13; or y is 4 and z is 12; or y is 5 and z is 11; or y is 6 and z is 10; or y is 7 and z is 9; or y is 9 and z is 7; or y is 10 and z is 6; or y is 11 and z is 5; or y is 12 and z is 4; or y is 13 and z is 3; or y is 14 and z is 2; or y is 15 and z is 1; or y is 16 and z is 0; or y is 1 and z is 16; or y is 2 and is 15; or y is 3 and z is 14; or y is 4 and z is 13; or y is 5 and z is 12; or y is 6 and z is 11; y is 7 and z is 10; y is 8 and z is 9; or y is 9 and z is 8; or y is 10 and z is 7; or y is 11 and z is 6; or y is 12 and z is 5; y is 13 and z is 4; or y is 14 and z is 3; or y is 15 and z is 2; or y is 16 and z is 1; or y is 17 and z is 0; or y is 0 and z is 17; or y is 1 and z is 17; or y is 2 and z is 16; or y is 3 and z is 15; or y is 4 and z is 14; or y is 5 and z is 13; or y is 6 and z is 12; or y is 7 and z is 11; or y is 8 and z is 10; or y is 10 and z is 8; or y is 11 and z is 7; or y is 12 and z is 6; or y is 13 and z is 5; or y is 14 and z is 4; or y is 15 and z is 3; or y is 16 and z is 2; or y is 17 and z is 1. In some embodiments, both y and z are 0, 1, 2, 3, 4, 5, 6, 7, 8, 9, 10, 11, 12, 13, 14, 15, 16, or 17.

In some embodiments, the method for synthesizing the fatty olefin metathesis product according to Formula I comprises contacting an olefin metathesis reaction partner of Formula III with an internal olefin according to Formula IV, wherein $R^1$ is $C_{1-3}$ alkyl, $R^2$ s $C_{1-12}$ alkyl, $R^3$ is $C_{1-12}$ alkyl, y is an integer ranging from 5 to 15, and z is an integer ranging from 0 to 7. In some embodiments, the method for synthesizing the fatty olefin metathesis product according to Formula I comprises contacting an olefin metathesis reaction partner of Formula III with an internal olefin according to Formula IV, wherein $R^1$ is selected from the group consisting of H and methyl; $R^2$ is n-butyl, n-pentyl, n-hexyl, n-heptyl, n-octyl, n-nonyl, and n-decyl; $R^3$ is selected from the group consisting of methyl, ethyl, n-propyl, n-butyl, n-pentyl, n-hexyl, and n-heptyl; y is an integer ranging from 6 to 14, and is an integer ranging from 1 to 4. In some embodiments, the method fix synthesizing the fatty olefin metathesis product according to Formula I comprises contacting an olefin metathesis reaction partner of Formula III with an internal olefin according to Formula IV, wherein $R^1$ is methyl; $R^2$ is selected from the group consisting of n-hexYl, n-heptyl, and n-octyl; $R^3$ is selected from the group consisting of ethyl, n-propyl, n-butyl, n-pentyl, and n-hexyl; y is an integer selected from the group consisting of 7, 9, 11, and 13; and z is an integer selected from the group consisting, of 1, 2, and 3. In some embodiments, the method for synthesizing the fatty olefin metathesis product according to Formula I comprises contacting an olefin metathesis reaction partner of Formula III with an internal olefin according to Formula IV, wherein $R^1$ is methyl; $R^2$ is n-octyl; $R^3$ is selected from the group consisting of ethyl and n-butyl; y is an integer selected from the group consisting of 7, 9, 11, and 13; and z is an integer selected from the group consisting of 1 and 3.

In some embodiments, the method for synthesizing the fatty olefin metathesis product according to Formula I comprises contacting an olefin metathesis reaction partner of Formula III with an internal olefin according to Formula IV, wherein the metathesis reaction partner according to Formula III is a fatty $C_{12}$-$C_{30}$ olefin acetate; the internal olefin according to Formula IV is a $C_4$-$C_{20}$ internal olefin; and the fatty olefin metathesis product according, to Formula I is a $C_8$-$C_{28}$ (Z)-unsaturated fatty ester acetate. In some embodiments, the metathesis reaction partner according to Formula III is a fatty $C_{16}$-$C_{28}$ olefin acetate; the internal olefin according to Formula IV is a $C_4$-$C_{12}$ internal olefin; and the fatty olefin metathesis product according to Formula I is a $C_{12}$-$C_{24}$ (Z)-insaturated fatty ester acetate. In some embodiments, the metathesis ivaction partner according to Formula III is a fatty $C_{18}$-$C_{26}$ olefin acetate; the internal olefin according to Formula IV is a $C_6$-$C_{10}$ internal olefin; and the fatty olefin metathesis product according to Formula I is a $C_{14}$-$C_{22}$ (Z)-unsaurated fatty ester acetate.

In some embodiments, the invention provides methods for synthesizing a fatty olefin metathesis product according to Formula I as described herein wherein the olefin metathesis reaction partner of Formula III is selected from the group comprising octadec-9-en-1-yl acetate, icos-11-en-1-yl acetate, docos-13-en-1-yl acetate, tetracos-15-en-1-yl acetate, or mixtures thereof. In some embodiments, the olefin metathesis reaction partner consists of octadec-9-en-1-yl acetate and at least one member selected from the group consisting of icos-11-en-1-yl acetate, docos-13-en-1-yl acetate, and tetracos-15-en-1-yl acetate. In some embodiments, the olefin metathesis reaction partner is selected from the group consisting of octadec-9-en-1-yl acetate, icos-11-en-1-yl acetate, docos-13-en-1-yl acetate, and tetracos-15-en-1-yl acetate. In some embodiments, the olefin metathesis reaction partner is octadec-9-en-1-yl acetate. In some embodiments, the olefin metathesis reaction partner is icos-11-en-1-yl acetate. In some embodiments, the olefin metathesis reaction partner is docos-13-en-1-yl acetate. In some embodiments, the olefin metathesis reaction partner is tetracos-15-en-1-yl acetate.

In some embodiments, the invention provides methods for synthesizing a fatty olefin metathesis product according to Formula I as described herein wherein the olefin of Formula IV is selected from the group comprising hexadec-8-ene, tetradec-7-ene, dodec-6-ene, dec-5-ene, oct-4-ene, or hex- 3-ene. In some embodiments, the olefin is selected from the group consisting of hexadec-8-ene, tetradec-7-ene, dodec-6-ene, dec-5-ene, oct-4-ene, and hex-3-ene. In some embodiments, the olefin is selected from the group consisting of tetradec-7-ene, dodec-6-ene, dec-5-ene, oct-4-ene and hex-3-ene. In some embodiments, the olefin is selected from the group consisting of dodec-6-ene, dec-5-ene, oct-4-ene, and hex-3-ene. In some embodiments, the olefin is selected from the group consisting of dec-5-ene, oct-4-ene, and hex-3-ene. In some embodiments, the olefin is dec-5-ene. In some embodiments, the olefin is oct-4-ene. In some embodiments, the olefin is hex-3-ene.

In some embodiments, the invention provides methods for synthesizing a fatty olefin metathesis product according to Formula I as described herein wherein the fatty olefin metathesis product is selected from the group comprising (Z)-tetradec-9-en-1-yl acetate, (Z)-hexadec-11-en-1-yl acetate, (Z)-octadec-13-en-1-yl acetate, (Z)-icos-15-en-1-yl acetate, (Z)-tridec-9-en-1-yl acetate, (Z)-pentadee-11-en-1-yl acetate, (Z)-beptader-13-en-1-yl acetate, (Z)-nonadec-15-en-1-yl acetate, (Z)-dodec-9-en-1-yl acetate, (Z)-tetradec-11-en-1-yl acetate, (Z)-hexadec-13-en-1-yl acetate, (Z)-ortadec-15-en-1-yl acetate, or mixtures thereof. In some embodiments, the fatty olefin metathesis product comprises at least one member selected from the group consisting of (Z)-tetradec-9-en-1-yl acetate, (Z)-hexadec-11-en-1-yl acetate, (Z)-octadec-13-en-1-yl acetate, and (Z)-icos-15-en-1-yl acetate. In some embodiments, the fatty olefin metathesis product comprises at least one member selected from the group consisting of (Z)-tridec-9-en-1-yl acetate, (Z)-pentadec-11-en-1-yl acetate, (Z)-heptadec-13-en-1-yl acetate, and (Z)-nonadec-15-en-1-yl acetate. In some embodiments, the fatty olefin metathesis product comprises at least one member selected from the group consisting of (Z)-dodec-9-en-1-yl acetate, (Z)-tetradec-11-en-1-yl acetate, (Z)-hexadec-3-en-1-yl acetate, and (Z)-octadec-15-en-1-yl acetate. In some embodiments, the fatty olefin metathesis product is selected from the group consisting of (Z)-tetradec-9-en-1-yl acetate, (Z)-dodec-9-en-1-yl acetate, and (Z)-tetradec-11-en-1-yl acetate.

In some embodiments, the method for synthesizing the fatty olefin metathesis product according to Formula I comprises contacting an olefin metathesis reaction partner of Formula III with an internal olefin according to Formula IV, wherein the olefin metathesis reaction partner according to Formula III comprises at least one member selected from the group consisting of (Z)-octadec-9-en-1-yl acetate, (Z)-icos-11-en-1-yl acetate, (Z)-docos-13-en-1-yl acetate, and (Z)-tetracos-15-en-1-yl acetate, the internal olefin according to Formula IV is selected from the group consisting of (Z)-dec-5-ene, (Z)-oct-4-ene, and (Z)-hex-3-ene; and the fatty olefin metathesis product according to Formula I comprises at least one member selected from the group consisting of (Z)-tetradec-9-en-1-yl acetate, (Z)-hexadec-11-en-1-yl acetate, (Z)-octadec-13-en-1-yl acetate, (Z)-icos-15-en-1-yl acetate, (Z)-tridec-9-en-1-yl acetate, (Z)-pentadec-11-en-1-yl acetate, (Z)-heptadec-13-en-1-yl acetate, (Z)-nonadec-15-en-1-yl acetate, (Z)-dodec-9-en-1-yl acetate, (Z)-tetradec-11-en-1-yl acetate, (Z)-hexadec-13-en-1-yl acetate and (Z)-octadec-15-en-1-yl acetate.

In some embodiments, the method for synthesizing, the fatty olefin metathesis product according to Formula I comprises contacting an olefin metathesis reaction partner of Formula III with an internal olefin according to Formula IV, wherein the olefin metathesis reaction partner according to Formula III comprises at least one member selected from the group consisting of (Z)-octadec-9-en-1-yl acetate, (Z)-icos-11-en-1-yl acetate, (Z)-docos-13-en-1-yl acetate, and (Z)-tetractis-15-en-1-yl acetate; the internal olefin according to Formula IV is (Z)-dec-5-ene; and the fatty olefin metathesis product according to Formula I comprises at least one member selected from the group consisting of (Z)-tetradec-9-en-1-yl acetate, (Z)-hexadec-11-en-1-yl acetate, (Z)-octadec-13-en-1-yl acetate, and (Z)icos-15-en-1-yl acetate.

In some embodiments, the method for synthesizing the fatty olefin metathesis product according to Formula I comprises contacting an olefin metathesis reaction partner of Formula III with an internal olefin according to Formula IV, wherein the olefin metathesis reaction partner according to Formula III comprises at least one member selected from the group consisting of (Z)-octadec-9-en-1-yl acetate, (Z)-icos-11-en-1-yl acetate, (Z)-docos-13-en-1-yl acetate, and (Z)-tetracos-15-en-1-yl acetate; the internal olefin according to Formula IV is (Z)-oct-4-ene, and the fatty olefin metathesis product according to Formula I comprises at least one member selected froom the group consisting of (Z)-tridec-9-en-1-yl acetate, (Z)-pentadec-11-en-1-yl acetate, (Z)-heptadec-13-en-1-yl acetate, and (Z)-nonadec-15-en-1-yl acetate.

In some embodiments, the method for synthesizing the fatty olefin metathesis product according to Formula I comprises contacting an olefin metathesis reaction partner of Formula III with an internal olefin according to Formula IV, wherein the olefin metathesis reaction partner according to Formula III comprises at least one member selected from the group consisting of (Z)-octadec-9-en-1-yl acetate, (Z)-icos-11-en-1-yl acetate, (Z)-docos-13-en-1-yl acetate, and (Z)-tetracos-15-en-1-yl acetate; the internal olefin according to Formula IV is (Z)-hex-3-ene; and the fatty olefin metathesis product according to Formula I comprises at least one member selected from the group consisting of (Z)-dodec-9-en-1-yl acetate, (Z)-acetate.

In some embodiments, the method for synthesizing the fatty olefin metathesis product according to Formula I comprises contacting an olefin metathesis reaction partner of Formula III with an internal olefin according to Formula IV, wherein the olefin metathesis reaction partner according to Formula III is (Z)-ocTadec-9-en-1-yl acetate; the internal olefin according to Formula IV is (Z)-dec-5-ene: and the fatty olefin metathesis product according to Formula I is (Z)-tetradec-9-en-1-yl acetate. In some embodiments, the method for synthesizing the fatty olefin metathesis product according to Formula I comprises contacting an olefin metathesis reaction partner of Formula III with an internal olefin according to Formula IV, wherein the olefin metathesis reaction partner according to Formula III is (Z)-octadec-9-en-1-yl acetate; the internal olefin according to Formula IV is (Z)-hex-3-ene and the fatty olefin metathesis product according to Formula I is (Z)-dodec-9-en-1-yl acetate. In some embodiments, the method for synthesizing the fatty olefin metathesis product according to Formula I comprises contacting an olefin metathesis reaction partner of Formula III with an internal olefin according to Formula IV, wherein the olefin metathesis reaction partner according to Formula III is (Z)-icos-11-en-1-yl acetate; the internal olefin according to Formula IV is (Z)-hex-3-ene; and the fatty olefin metathesis product according to Formula is (Z)-tetradec-11-en-1-yl acetate.

In some embodiments, the method for synthesizing the fatty olefin metathesis product according to Formula I comprises contacting an acylating agent with an alkenol according to Formula II to form an olefin metathesis reaction partner according to Formula III, and contacting the olefin metathesis reaction partner of Formula III with an internal olefin according to Formula IV, wherein $R^1$ alkyl is $C_{1-3}$ alkyl, $R^2$ is $C_{1-12}$ alkyl, y is an integer ranging from 5 to 15, and z is an integer ranging from 0 to 7. In some embodiments, the method for synthesizing the fatty olefin metathesis product according to Formula I comprises contacting an acylating agent with an alkenol according to Formula II to form an olefin metathesis reaction partner according to Formula III and contacting the olefin metathesis reaction partner of Formula III with an internal olefin according to Formula IV, wherein $R^1$ is selected from the group consisting of H and methyl; $R^2$ is n-butyl, n-pentyl, n-hexyl, n-heptyl, n-octyl, n-nonyl, and n-decyl; $R^3$ selected from the group consisting of methyl, ethyl, n-propyl, n-butyl, n-pentyl, n-hexyl, and n-heptyl; y is an integer ranging from 6 to 14, and z is an integer ranging from 1 to 4. In some embodiments, the method for synthesizing the fatty olefin metathesis product according to Formula I comprises contacting an acylating agent with an alkenol according to Formula II to form an olefin metathesis reaction partner according to Formula III, and contacting the olefin metathesis reaction partner of Formula III with an internal olefin according to Formula IV, wherein $R^1$ is methyl; $R^2$ is selected from the group consisting of n-hexyl, n-heptyl, and n-octyl; $R^3$ is selected from the group consisting of ethyl, n-propyl, n-butyl, n-pentyl, and n-hexyl; y is an integer selected from the group consisting of 7, 9, 11, and 13; and z is an integer selected from the group consisting of 1, 2, and 3. In some embodiments, the method for synthesizing the fatty olefin metathesis product according to Formula I comprises contacting an acylating agent with an alkenol according to Formula II to form an olefin metathesis reaction partner according to Formula III, and contacting the olefin metathesis reaction partner of Formula III with an internal olefin according to Formula IV, wherein $R^1$ is methyl $R^2$ is n-octyl; $R^3$ is selected from the group consisting of ethyl and n-butyl; y is an integer selected from the group consisting of 7, 9, 11, and 13; and z is an integer selected from the group consisting of 1 and 3.

In some embodiments, the method for synthesizing the fatty olefin metathesis product according to Formula I comprises contacting an acylating agent with an alkenol according to Formula II to form an olefin metathesis reaction partner according to Formula III, and contacting the olefin metathesis reaction partner of Formula III with an internal olefin according to Formula IV, wherein the alkenol according to Formula II is a $C_{10}$-$C_{28}$, fatty alkenol; the metathesis reaction paaccording to Formula III is an acetate ester of the $C_{10}$-$C_{28}$ fatty alkenol; the internal olefin according to Formula IV is a $C_4$-$C_{20}$ internal olefin; and the fatty olefin metathesis product according to Formula I is a $C_8$-$C_{28}$ (Z)-unsaturated fatty ester acetate. In some embodiments, the alkenol according to Formula II is a $C_{14}$-$C_{26}$ fatty alkenol; the metathesis reaction partner according to Formula III is an acetate ester of the $C_{14}$-$C_{26}$ fatty alkenol; the internal olefin according to Formula IV is a $C_4$-$C_{12}$ internal olefin; and the fatty olefin metathesis product according to Formula I is a $C_{12}$-$C_{24}$ (Z)-unsaurated fatty ester acetate. In some embodiments, the alkenol according to Formula II is a $C_{16}$-$C_{24}$ fatty alkenol; the metathesis reaction partner according to Formula III is an acetate ester of the $C_{16}$-$C_{24}$ fatty alkenol; the internal olefin according to Formula IV is a $C_6$-$C_{10}$ internal olefin; and the fatty olefin metathesis product according to Formula I is a $C_{14}$-$C_{22}$ (Z)-unsaurated fatty ester acetate.

In some embodiments, the invention provides methods for synthesizing a fatty olefin metathesis product according to Formula I as described herein wherein the alkenol according to Formula II is selected from the group comprising octadec-9-en-1-ol, icos-11-en-1ol, docos-13-en-1-ol, tetracos-15-en-ol, or mixtures thereof. In some embodiments, the alkenol is selected from the group consisting of octadec-9-en-1-ol, icos-11-en-1-ol, docos-13-en-1-ol, and tetracos-15-en-ol. In some embodiments, the alkenol is octadec-9-en-1-ol. In some embodiments, the alkenol is icos-11-en-1-ol. In some embodiments, the alkenol is docos-13-en-1-ol. In some embodiments, the alkenol is tetracos-15-en-ol.

In some embodiments, the method for synthesizing the fatty olefin metathesis product according to Formula I comprises contacting an acylating agent with an alkenol according to Formula II form an olefin metathesis reaction partner according to Formula III, and contacting the olefin metathesis reaction partner of Formula III with an internal olefin according to Formula IV, wherein the alkenol according to Formula II comprises at least one member selected from the group consisting of (Z)-ortadec-9-en-1-ol, (Z)-docos-13-en-1-ol, and (Z)-tetracos-15-en-ol; the olefin metathesis reaction partner according to Formula III comprises at least one member selected from the group consisting of (Z)-octadec-9-en-1-yl acetate, (Z)-icos-11-en-1-yl acetate, (Z)-docos-13-en-1-yl acetate, and (Z)tetracos-15-en-1-yl acetate; the internal olefin according to Formula IV is selected from the group consisting of (Z)-dec-5-ene, (Z)-oct-4-ene, and (Z)-hex-3-ene; and the fatty olefin metathesis product according to Formula I comprises at least one member selected from the group consisting of (Z)-tetradec-9-en-1-yl acetate, (Z)-hexadec-11-en-1-yl acetate, (Z)-octadec-13-en-1-yl acetate, (Z)-icos-15-en-1-yl acetate, (Z)-tridec-9-en-1-yl acetate, (Z)-pentadec-11-en-1 acetate, (Z)-heptadec-13-en-1-yl acetate, (Z)-nonadec-15-en-1-yl acetate, (Z)-dodec-9-en-1-yl acetate, (Z)-tetradec-11-en-1-yl acetate, (Z)-hexadec-13-en-1-yl acetate and (Z)-octadec-15-en-1-yl acetate.

In some embodiments, the method for ssynthesizing the fatty olefin metathesis product according to Formula I comprises contacting an acylating agent with an alkenol according to Formula II to form an olefin metathesis reaction partner according to Formula III, and contacting the olefin metathesis reaction partner of Formulae III with an internal olefin according to Formula IV, wherein the alkenol according to Formula II comprises at least one member selected from the group consisting of (Z)-octadec-9-en-1-ol, (Z)-docos-13-en-1-ol and (Z)-tetracos-15-en-ol; the olefin metathesis reaction partner according to Formula III comprises at least one member selected from the group consisting of (Z)-octadec-9-en-1-yl acetate, (Z)-icos-11-en-1-yl acetate, (Z)-docos-13-en-1-yl acetate, and (Z)-tetracos-15-en-1-yl acetate; the internal olefin according to Formula IV is (Z)-dec-5-ene; and the fatty olefin metathesis product according to Formula I comprises at least one member selected from the group consisting of (Z)-tetradec-9-en-1-yl acetate, (Z)-hexadec-11-en-1-yl acetate, (Z)-octadec-13-en-1-yl acetate, and (Z)-icos-15-en-1-yl acetate.

In some embodiments, the method for synthesizing the fatty olefin metathesis product according to Formula I comprises contacting an acylating agent with an alkenol according to Formula II to form an olefin metathesis reaction partner according to Formula III, and contacting the olefin metathesis reaction partner of Formula III with an internal olefin according to Formula IV, wherein the alkenol according to Formula II comprises at least one member selected from the group consisting of (Z)-octadec-9-en-1-ol, (Z)-icos-11-en-1-ol, (Z)-docos-13-en-1-ol, and (Z)-tetracos-15-en-ol; the olefin metathesis reaction partner according to Formula III composes at least one member selected from the group consisting of (Z)-octadec-9-en-1-yl acetate, (Z)-icos-11-en-1-yl acetate, (Z)-docos-13-en-1-yl acetate, and (Z)-tetracos-15-en-1-yl acetate; the internal olefin according to Formula IV is (Z)-oct-4-ene; and the fatty olefin metathesis product according to Formula I comprises at least one member selected from the group consisting of (Z)-tridec-9-en-1-yl acetate, (Z)-pentadec-11-en-1-yl acetate, (Z)-heptadec-13-en-1-yl acetate, and (Z)-nonadec-15-en-1-yl acetate.

In some embodiments, the method for synthesizing the fatty olefin metathesis product according to Formula I comprises contacting an acylating agent with an alkenol according to Formula II to form an olefin metathesis reaction partner according to Formula III, and contacting the olefin metathesis reaction partner of Formula III with an internal olefin according to Formula IV, wherein the alkettol according to Formula II comprises at least one member selected from the group consisting of (Z)-octadec-9-en-1-ol, (Z)-icos-11-en-1-ol, (Z)-docos-13-en-1-ol, and (Z)-tetracos-15-en-ol; the olefin metathesis reaction partner according to Formula III comprises at least one member selected from the group consisting of (Z)-octadec-9-en-1-yl acetate, (Z)-icos-11-en-1-yl acetate, (Z)-docos-13-en-1-yl acetate, and (Z)-tetracos-15-en-1-yl acetate; the internal olefin according to Formula IV is (Z)-hex-3-ene; and the fatty olefin metathesis product according to Formula I comprises at least one member selected from the group consisting of (Z)-dodec-9-en-1-yl acetate, (Z)-tetradec-11-en-1-yl acetate, (Z)-hexadec-13-en-1-yl acetate, and (Z)-octadec-15-en-1-yl acetate.

In some embodiments, the method for synthesizing the fatty olefin metathesis product according to Formula I comprises contacting an acylating agent with an alkenol according to Formula II to form an olefin metathesis reaction partner according to Formula III, and contacting the olefin metathesis reaction partner of Formula III with an internal olefin according to Formula IV, wherein the alkenol according to Formula II is (Z)-octadec-9-en-1-ol; the olefin metathesis reaction partner according to Formula III is (Z)-octadec-9-en-1-yl acetate; the internal olefin according to Formula IV is (Z)-dec-5-ene; and the fatty olefin metathesis product according to Formula I is (Z)-tetradec-9-en-1-yl acetate. In some embodiments, the method for synthesizing the fatty olefin metathesis product according to Formula I comprises contacting an acylating agent with an alkenol according to Formula II to form an olefin metathesis reaction partner according to Formula III, and contacting the olefin metathesis reaction partner of Formula III an internal olefin according to Formula IV, wherein the alkenol according to Formula II is (Z)-octadec-9-en-1-ol, the olefin metathesis reaction partner according to Formula III is (Z)-octadec-9-en-1-yl acetate; the internal olefin according to Formula IV is (Z)-hex-3-ene; and the fatty olefin metathesis product according to Formula I is (Z)-dodec-9-en-1-yl acetate. In some embodiments, the method for synthesizing the fatty olefin metathesis product according to Formula I comprises contacting an acylating agent with an alkenol according to Formula II to form an olefin metathesis reaction partner according to Formula III, and contacting the olefin metathesis reaction partner of Formula III with an internal olefin according to Formula IV, wherein the alkenol according to Formula II is (Z)-icos-11-en-1-ol; the olefin metathesis reaction partner according to Formula III is (Z)-icos-11-en-1-yl acetate; the internal olefin according to Formula IV is (Z)-hex-3-ene; and the fatty olefin metathesis product according to Formula I is (Z)-tetradec-11-en-1-yl acetate.

In some embodiments, the method for synthesizing the fatty olefin metathesis product according to Formula I comprises reducing an unsaturated fatty carboxyl derivative according to Formula IIa to form an alkenol according to Formula II, contacting an acylating agent with an alkenol according to Formula II to form an olefin metathesis reaction partner according to Formula III, and contacting the olefin metathesis reaction partner of Formula III an internal olefin according to Formula IV, wherein $R^1$ is $C_{1-3}$ alkyl, $R^2$ is $C_{1-12}$ alkyl, $R^3$ is $C_{1-12}$ alkyl, $R^4$ is selected from the group consisting of H and $C_{1-3}$ alkyl, y is an integer ranging from 5 to 15, and is an integer ranging from 0 to 7. In some embodiments, $R^1$ is $C_{1-3}$ alkyl, $R^2$ is $R^2$ alkyl, $R^3$ is $C_{1-12}$ alkyl, $R^4$ is $C_{1-3}$ alkyl, and z rs an integer ranging from 1 to 5. In some embodiments, $R^1$ is $C_{1-3}$ alkyl, $R^2$ is $C_{1-12}$ alkyl, $R^3$ is $C_{1-12}$ alkyl, $R^4$ is H, y is an integer ranging from 5 to 15, and z is an integer ranging from 1 to 5.

In some embodiments, the method for synthesizing the fatty olefin metathesis product according to Formula I comprises reducing an unsaturated fatty carboxyl derivative according to Formula IIa to form an alkenol according to Formula II, contacting, an acylating agent with an alkenol according to Formula II to form art olefin metathesis reaction partner according to Formula III, and contacting the olefin metathesis reaction partner of Formula III with an internal olefin according to Formula IV, wherein $R^1$ is selected from the group consisting of H and methyl; $R^2$ is to n-butyl, n-pentyl, n-hexyl, n-heptyl, n-octyl, n-nonyl, and n-decyl; $R^3$ is selected from the group consisting of methyl, ethyl, n-propyl, n-butyl, n-pentyl, n-hexyl, and n-heptyl; $R^4$ is selected from the group consisting of H and methyl; y is an integer ranging from 6 to 14, and z is an integer ranging from 1 to 4. In some embodiments, $R^1$ is methyl; $R^2$ is selected from the group consisting of n-hexyl, n-heptyl, and n-octyl; $R^3$ is selected from the group consisting of ethyl, n-propyl, n-butyl, n-pentyl, and n-hexyl; $R^4$ is methyl; y an integer selected from the group consisting of 7, 9, 11, and 13; and z is an integer selected front the group consisting of 1, 2, and 3. In some embodiments, $R^1$ is methyl; $R^2$ is selected from the group consisting of n-hexyl, n-heptyl, and n-octyl; $R^3$ is selected from the group consisting of ethyl, n-propyl, n-butyl, n-pentyl, and n-hexyl; $R^4$ is H; y is an integer selected from the group consisting of 7, 9, 11, and 13; and z is an integer selected from the group consisting of 1, 2, and 3.

In some embodiments, the method for synthesizing the fatty olefin metathesis product according to Formula I comprises reducing an unsaturated fatty carboxyl derivative according to Formula IIa to form an alkenol according to Formula II, contacting an acylating agent with an alkenol according to Formula II to form an olefin metathesis reaction partner according to Formula III, and contacting the olefin metathesis reaction partner of Formula III with an internal olefin according to Formula IV, wherein $R^1$ is methyl; $R^2$ is n-octyl; $R^3$ is selected front the group consisting of ethyl and n-butyl; $R^4$ is methyl; y is an integer selected from the group consisting of 7, 9, 11, and 13; and z is an integer selected from the group consisting of 1 and 3. In some embodiments, $R^1$ is methyl; $R^2$ is n-octyl; $R^3$ is selected from the group consisting of ethyl and n-butyl; $R^4$ is methyl; y is an integer selected front the group consisting of 7; and z is an integer selected front the group consisting of 1 and 3. In some embodiments, $R^1$ is methyl; $R^2$ is n-octyl; $R^3$ is selected from the group consisting of ethyl and n-butyl; $R^4$ is H; y is an integer selected from the group consisting of 7, 9, 11, and 13; and z is an integer selected from the group consisting of 1 and 3. In some embodiments, $R^1$ is methyl; $R^2$ is n-octyl; $R^3$ is selected from the group consisting of ethyl and n-butyl;

$R^4$ is H; y is an integer selected from the group consisting of and z is an integer selected front the group consisting of 1 and 3.

In some embodiments, when $R^4$ of Formula IIa is alkyl (e.g., $C_{1-3}$ alkyl, methyl, etc.), the unsaturated fatty carboxyl derivative is an unsaturated fatty acid alkyl ester. Accordingly, in some embodiments, the method for synthesizing the fatty olefin metathesis product according to Formula I comprises reducing an unsaturated fatty acid alkyl ester according to Formula IIa to form an alkenol according to Formula II, contacting an acylating agent with an alkenol according to Formula II to form an olefin metathesis reaction partner according to Formula III and contacting the olefin metathesis reaction partner of Formula III with an internal olefin according to Formula IV, wherein the unsaturated fatty acid alkyl ester according to Formula IIa is $C_{11}$-$C_{29}$ unsaturated fatty acid methyl ester; the alkenol according to Formula II is a $C_{10}$-$C_{28}$ fatty alkenol; the metathesis reaction partner according to Formula III is an acetate ester of the $C_{10}$-$C_{28}$ fatty alkenol; the internal olefin according to Formula IV is a $C_4$-$C_{20}$ internal olefin; and the fatty olefin metathesis product according to Formula I is a $C_8$-$C_{28}$ (Z)-unsaturated fatty ester acetate. In some embodiments, the unsaturated fatty acid alkyl ester according to Formula IIa $C_{15}$-$C_{27}$ unsaturated fatty acid methyl ester; the alkenol according to Formula II is a $C_{14}$-$C_{26}$ fatty alkenol; the metathesis reaction partner according to Formula III is an acetate ester of the $C_{14}$-$C_{26}$ fatty alkenol; the internal olefin according to Formula IV is a $C_4$-$C_{12}$ internal olefin; and the fatty olefin metathesis product according to Formula I is a $C_{12}$-$C_{24}$ (Z)-unsaturated fatty ester acetate. In some embodiments, the unsaturated fatty acid alkyl ester according to Formula IIa is $C_{17}$-$C_{25}$ unsaturated fatty acid methyl ester: the alkenol according to Formula II is a $C_{16}$-$C_{24}$ fatty alkenol; the metathesis reaction partner according to Formula III is an acetate ester of the $C_{16}$-$C_{24}$ fatty alkenol; the internal olefin according to Formula IV is a $C_6$-$C_{10}$ internal olefin; and the fatty olefin metathesis product according to Formula I is a $C_{14}$-$C_{22}$ (Z)-unsaturated fatty ester acetate.

In some embodiments, the invention provides methods for synthesizing a fatty olefin metathesis product according to Formula I as described herein wherein the unsaturated fatty acid alkyl ester of Formula IIa is selected from the group comprising methyl octadec-9-enoate, methyl icos-11-enoate, methyl docos-13-enoate, methyl tencos-15-enoate, or mixtures thereof. In some embodiments, the unsaturated fatty acid alkyl ester consists of methyl octadec-9-enoate and at least one member selected from the group consisting of methyl icos-11-enoate, methyl docos-13-enoate, and methyl tetracos-15-enoate. In some embodiments, the unsaturated fatty acid alkyl ester is selected from the group consisting of methyl octadec-9-enoate, methyl icos-11-enoate, methyl docos-13-enoate, and methyl tetracos-15-enoate. In some embodiments, the unsaturated fatty acid alkyl ester is methyl octadec-9-enoate. In some embodiments, the unsaturated fatty acid alkyl ester is methyl icos-11-enoate. In some embodiments, the unsaturated fatty acid alkyl ester is methyl docos-13-enoate. In some embodiments, the unsaturated fatty acid alkyl ester is methyl tetracos-15-enoate.

In some embodiments, the method for synthesizing the fatty olefin metathesis product according to Formula I comprises reducing an unsaturated fatty acid alkyl ester according to Formula IIa to form an alkenol according to Formula II, contacting an acylating agent with an alkenol according to Formula II to form an olefin metathesis reaction partner according to Formula III, and contacting the olefin metathesis reaction partner of Formula III with an internal olefin according to Formula IV, wherein the unsaturated fatty acid alkyl ester according to Formula IIa comprises at least one member selected from the group consisting of methyl (Z)-octadec-9-enoate, methyl (Z)-icos-11-enoate, methyl (Z)-docs-13-enoate, and methyl (Z)-tetracos-15-enoate; the alkenol according to Formula II comprises at least one member selected from the group consisting of (Z)-octadec-9-en-1-ol, (Z)-icos-11-en-1-ol, (Z)-docos-13-en-1-ol, and (Z)-tetracos-15-en-ol; the olefin metathesis reaction partner according to Formula III comprises at least one member selected from the group consisting of (Z)-octadec-9-en-1-yl acetate, (Z)-icos-11-en-1-yl acetate, (Z)-docos-13-en-1-yl acetate, and (Z)-tetracos-15-en-1-yl acetate; the internal olefin according to Formula IV is selected from the group consisting of (Z)-dec-5-ene, (Z)oct-4-ene, and (Z)-hex-3-ene; and the fatty olefin metathesis product according to Formula I comprises at least one member selected from the group consisting of (Z)-tetradec-9-en-1-yl acetate, (Z)-hexadec-11-en-1-yl acetate, (Z)-octadec-13-en-1-yl acetate, (Z)-icos-15-en-1-yl acetate, (Z)-tridec-9-en-1-yl acetate, (Z)-pentadec-11-en-1-yl acetate, (Z)-heptadec-13-en-1-yl acetate, (Z)-nonadec-15-en-1-yl acetate, (Z)-dodec-9-en-1-yl acetate, (Z)-tetradec-11-en-1-yl acetate, (Z)-hexadec-13-en-1-yl acetate, and (Z)-octadec-15-en-1-yl acetate.

In some embodiments, the method for synthesizing the fatty olefin metathesis product according to Formula I comprises reducing an unsaturated ratty acid alkyl ester according to Formula IIa to form an alkenol according to Formula II, contacting an acylating agent with an alkenol according to Formula II to form an olefin metathesis reaction partner according to Formula III, and contacting the olefin metathesis reaction partner of Formula III with an internal olefin according to Formula IV, wherein the unsaturated fatty acid alkyl ester according to Formula IIa is methyl (Z)-octadec-9-enoate; the alkenol according to Formula II is (Z)-octadec-9-en-1-ol; the olefin metathesis reaction partner according to Formula III is (Z)-octadec-9-en-1-yl acetate; the internal olefin according to Formula IV is (Z)-dec-5-ene; and the fatty olefin metathesis product according to Formula I is (Z)-tetradec-9-en-1-yl acetate.

In some embodiments, the method for synthesizing the fatty olefin metathesis product according to Formula I comprises reducing an unsaturated fatty acid alkyl ester according to Formula IIa to form an alkenol according to Formula II, contacting an acylating agent with an alkenol according to Formula II to form an olefin metathesis reaction partner according to Formula III, and contacting the olefin metathesis reaction partner of Formula III with an internal olefin according to Formula IV, wherein the unsaturated fatty acid alkyl ester according to Formula IIa is methyl (Z)-octadec-9-enoate; the alkenol according to Formula II is (Z)-octadec-9-en-1-ol; the olefin metathesis reaction partner according to Formula III is (Z)-octadec-9-en-1-yl acetate; the internal olefin according to Formula IV is (Z)-hex-3-ene; and the fatty olefin metathesis product according to Formula I is (Z)-dodec-9-en-1-yl acetate.

In some embodiments, the method for synthesizing the fatty olefin metathesis product according to Formula I comprises reducing an unsaturated fatty acid alkyl ester according to Formula IIa to form an alkenol according to Formula II, contacting an acylating agent with an alkenol according to Formula II to form an olefin metathesis reaction partner according to Formula III and contacting the olefin metathesis reaction partner of Formula III with an internal olefin according to Formula IV, wherein the unsaturated fatty acid alkyl ester according to Formula IIa is methyl (Z)-eicos-11-enoate; the alkenol according to Formula II is (Z)-eicos-11-en-1-ol the olefin metathesis reaction partner according to Formula III is (Z)-eicos-11-en-1-yl acetate; the internal olefin according to Formula IV is (Z)-hex-3-ene; and the fatty olefin metathesis product according to Formula I is (Z)-tetradec-11-en-1-yl acetate. The prefixes "icos" and "eicos" are used interchangeably to refer to a hydrocarbon chain having carbons (i.e., methyl (Z)-eicos-11-enoate, (Z)-eicos-11-en-1-ol, and (Z)-eicos-11-en-1-yl acetate correspond to methyl (Z)-icos-11-enoate, (Z)-icos-11-en-1-ol, and (Z)-icos-11-en-1-yl acetate, respectively).

In some embodiments, when $R^4$ of Formula IIa is H, the unsaturated fatty carboxyl derivative is an unsaturated fatty acid. Accordingly, in some embodiments, the method for synthesizing the fatty olefin metathesis product according to Formula I comprises reducing an unsaturated fatty acid, according to Formula IIa to form an alkenol according to Formula II, contacting an acylating agent with an alkenol according to Formula II to form an olefin metathesis reaction partner according to Formula III, and contacting the olefin metathesis reaction partner of Formula III with an internal olefin according to Formula IV, wherein the unsaturated fatty acid according to Formula IIa is $C_{10}$-$C_{28}$ unsaturated fatty acid; the alkenol according to Formula II is a $C_{10}$-$C_{28}$ fatty alkenol; the metathesis reaction partner according to Formula III is an acetate ester of the $C_{10}$-$C_{28}$ fatty alkenol; the internal olefin according to Formula IV is a $C_4$-$C_{20}$ internal olefin; and the fatty olefin metathesis product according to Formula I is a $C_8$-$C_{28}$ (Z)-unsaturated fatty ester acetate. In some embodiments, the unsaturated fatty acid according to Formula IIa is $C_{14}$-$C_{26}$ unsaturated fatty acid; the alkenol according to Formula II is a $C_{14}$-$C_{26}$ fatty alkenol; the metathesis reaction partner according to Formula III is an acetate ester of the $C_{14}$-$C_{26}$ fatty alkenol; the internal olefin according to Formula IV is a $C_4$-$C_{12}$ internal olefin; and the fatty olefin metathesis product according to Formula I is a $C_{12}$-$C_{24}$ (Z)-unsaturated fatty ester acetate. In some embodiments, the unsaturated fatty acid according to Formula IIa is $C_{16}$-$C_{24}$ unsaturated fatty acid; the alkenol according to Formula II is a $C_{16}$-$C_{24}$ fatty alkenol; the metathesis reaction partner according to Formula III is art acetate ester of the $C_{16}$-$C_{24}$ fatty alkenol; the internal olefin according to Formula IV is a $C_6$-$C_{10}$ internal olefin; and the fatty olefin metathesis product according to Formula I is a $C_{14}$-$C_{22}$ (Z) unsaturated fatty ester acetate.

In some embodiments, the invention provides methods for synthesizing a fatty olefin metathesis product according to Formula I as described herein wherein the unsaturated fatty add according to Formula IIa is selected from the group comprising octadec-9-enoic add, icos-11-enoic acid, docos-13-enoic acid, tetracos-15-enoic acid, or mixtures thereof. In some embodiments, the unsaturated fatty acid consists of octadec-9-enoic acid and at least one member selected from the group consisting of icos-11-enoic acid, docos-13-enoic acid, and tetracos-15-enoic acid. In some embodiments, the unsaturated fatty acid is selected from the group consisting of octadec-9-enoic acid, icos-11-enoic acid, docos-13-enoic acid, and tetracos-15-enoic acid. In some embodiments, the unsaturated fatty acid, is octadec-9-enoic acid. In some embodiments, the unsaturated fatty acid is icos-11-enoic acid. In some embodiments, the unsaturated fatty acid is docos-13-enoic acid. In some embodiments, the unsaturated fatty acid is tetracos-15-enoic acid.

In some embodiments, the method for synthesizing the fatty olefin metathesis product according to Formula I comprises reducing an unsaturated fatty acid according to Formula IIa to form an alkenol according to Formula II, contacting an acylating agent with at alkenol according to Formula II to form an olefin metathesis reaction partner according to Formula III, and contacting the olefin metathesis reaction partner of Formula III with an internal olefin according to Formula IV, wherein the unsaturated fatty acid according to Formula IIa comprises at least one member selected from the group consisting of (Z)-octadec-9-enoic acid. (Z)-icos-11-enoic acid, (Z)-docos-13-enoic acid, and (Z)-tetracos-15-enoic acid; the alkenol according to Formula II comprises at least one member selected from the group consisting of (Z)-octadec-9-en-1-ol, (Z)-icos-11-en-1-ol, (Z)-docos-13-en-1-ol, and (Z)-tetracos-15-en-ol; the olefin metathesis reaction partner according to Formula III comprises at least one member selected from the group consisting of (Z)-octadec-9-en-1-yl acetate, (Z)-icos-11-en-1-yl acetate, (Z)-docos-13-en-1yl acetate, and (Z)-tetracos-15-en-1-yl acetate; the internal olefin according to Formula IV is selected from the group consisting of (Z)-dec-5-ene, (Z)-oct-4-ene, and (Z)-hex-3-ene; and the fatty olefin metathesis product according to Formula I comprises at least one member selected from the group consisting of (Z)-tetradec-9-en-1-yl acetate, (Z)-hexadec-11-en-1-yl acetate, (Z)-octadec-13-en-1-yl acetate, (Z)-icos-15-en-1-yl acetate, (Z)-tridec-9-en-1-yl acetate, (Z)-pentadec-11-en-1-yl acetate, (Z)-heptadec-13-en-1-yl acetate, (Z)-nonadec-15-en-1-yl acetate, (Z)-dodec-9en-1-yl acetate, (Z)-tetradec-11-en-1-yl acetate, (Z)-hexadec-13-en-1-yl acetate, and (Z)-octadec-15-en-1-yl acetate.

In some embodiments, the unsaturated fatty carboxyl derivative of Formula IIa is derived from a natural oil. In some embodiments, the unsaturated fatty carboxyl derivative of Formula IIa is an unsaturated fatty acid obtained from a natural oil or a natural oil derivative. A natural oil or natural oil derivative suitable for use in the methods of the instant invention include natural oils and/or derivatives thereof which comprise (Z)-octadec-9-enoic acid, (Z)-icos-11-enoic acid, (Z)-docos-13-enoic acid, (Z)-tetracos-15-enoic acid, or mixtures thereof. In some embodiments, the unsaturated fatty acids of Formula IIa are obtained from a natural oil selected from the group consisting of almond oil, canola oil, avocado oil, argan oil, rapeseed oil, coconut oil, corn oil, cottonseed oil, grape seed oil, olive oil, palm oil, peanut oil, hemp oil, macadamia oil, safflower oil, sesame oil, soybean oil, sunflower oil, linseed oil, palm kernel oil, tung oil, jatropha oil, jojoba sail, mustard oil, pennycress oil, camelina oil, castor oil, and combinations thereof. In some embodiments, the unsaturated fatty acids of Formula IIa are obtained from a natural oil selected from the group consisting of canola oil, avocado oil, olive oil, palm oil, peanut oil, safflower oil, soybean oil, sunflower oil, jojoba oil, and combinations thereof. In some embodiments, the unsaturated fatty acids of Formula IIa are obtained from a natural oil selected from the group consisting of canola oil, avocado oil, olive oil, safflower oil, jojoba oil, and combinations thereof. In some embodiments, the unsaturated fatty acids of Formula IIa are obtained from a natural oil selected from the group consisting of canola oil, avocado oil, jojoba oil, and combinations thereof. In some embodiments, the unsaturated fatty acids of Formula IIa are obtained from a natural oil selected front the group consisting of canola oil and jojoba oil. In some embodiments, the unsaturated fatty acids of Formula IIa are obtained from jojoba oil.

In some embodiments, the method for synthesizing the fatty olefin metathesis product according to Formula I comprises reducing an unsaturated fatty acid according to Formula IIa to form an alkenol according to Formula II, contacting an acylating agent with an alkenol according to Formula II to form an olefin metathesis reaction partner according to Formula III, and contacting the olefin metathesis reaction partner of Formula III with an internal olefin according to Formula IV, therein the unsaturated fatty acid according to Formula IIa is obtained from a natural oil or derivative thereof, and comprises at least one member selected from the group consisting, of (Z)-octadec-9-enoic acid, (Z)-icos-11-enoic acid, (Z)-docos-13-enoic acid, and (Z)-tetracos-15-enoic acid; the alkenol according to Formula II comprises at least one member selected from the group consisting of (Z)-octadec-9-en-1-ol, (Z)-icos-11-en-1-ol, (Z)-docos-13-en-1-ol, and (Z)-tetracos-15-en-ol; the olefin metathesis reaction partner according to Formula III comprises at least one member selected from the group consisting of (Z)-octadec-9-en-1-yl acetate, (Z)-icos-11-en-1-yl acetate, (Z)-docos-13-en-1-yl acetate, and (Z)-tetracox-15-en-1-yl acetate; the internal olefin according to Formula IV is (Z)-dec-5-ene; and the fatty olefin metathesis product according to Formula I comprises at least one member selected from the group consisting of (Z)-tetradec-9-en-1-yl acetate, (Z)-hexadec-11-en-1-yl acetate, (Z)-octadec-13-en-1-yl acetate, and (Z)-icos-15-en-1-yl acetate.

In some embodiments, the method for synthesizing the fatty olefin metathesis product according to Formula I comprises reducing an unsaturated fatty acid according to Formula IIa to form an alkenol according to Formula II, contacting an acylating agent with an alkenol according to Formula II to form an olefin metathesis reaction partner according to Formula III, and contacting the olefin metathesis reaction partner of Formula III an internal olefin according to Formula IV, wherein the unsaturated fatty acid according to Formula IIa is obtained from a natural oil or derivatiye thereof, and comprises at least one member selected from the group consisting of (Z)-octadec-9-enoic acid, (Z)-icos-11-enoic acid, (Z)-docos-13-enoic acid, and (Z)-tetracos-15-enoic acid; the alkenol according to Formula II comprises at least one member selected from the group consisting of (Z)-octadec-9-en-1-ol, (Z)-icos-11-en-1-ol, (Z)-docas-13-en-1-ol, and (Z)-tetracos-15-en-el; the olefin metathesis reaction partner according to Formula III comprises at least one member selected from the group consisting of (Z)-octadec-9-en-1-yl acetate, (Z)-icos-11-en-1-yl acetate, (Z)-docos-13-en-1-yl acetate, and (Z)-tetracas-15-en-1-yl acetate; the internal olefin according to Formula IV is (Z)-oct-4-ene; and the fatty olefin metathesis product according to Formula I comprises at least one member selected from the group consisting of (Z)-tridec-9-en-1-yl acetate, (Z)-pentadec-11-en-1-yl acetate, (Z)-heptadec-13-en-1-yl acetate, and (Z)-nonadec-15-en-1-yl acetate.

In some embodiments, the method for synthesizing the fatty olefin metathesis product according to Formula I comprises reducing, an unsaturated fatty acid according to Formula IIa to form an alkenol according to Formula II, contacting an acylating agent with an alkenol according to Formula II to form an olefin metathesis reaction partner according to Formula III, and contacting the olefin metathesis reaction partner of Formula III with an internal olefin according to Formula IV, wherein the unsaturated fatty acid according to Formula IIa is obtained from a natural oil or derivative thereof, and comprises at least one member selected from the group consisting of (Z)-octadec-9-enoic acid, (Z)-icos-11-enoic acid, (Z)-docos-13-enoic acid, and (Z)-tetracos-15-enoic acid; the alkenol according to Formula II comprises at least one member selected from the group consisting of (Z)-octadec-9-en-1-ol, (Z)-icos-11-en1-ol, (Z)-docos-13-en-1-ol, and (Z)-tetracos-15-en-ol; the olefin metathesis reaction partner according to Formula III comprises at least one member selected from the group consisting of (Z)-octadec-9-en-1-yl acetate. (Z)-icos-11-en-1-yl acetate, (Z)-docos-13-en-1-yl acetate, and (Z)-tetraeos-15-en-1-yl acetate; the internal olefin according to Formula IV is (Z)-hex-3-ene; and the fatty olefin metathesis product according to Formula I comprises at least one member selected from the group consisting of (Z)-dodec-9-en-1-yl acetate, (Z)-tetradec-11-en-1-yl acetate, (Z)-hexadec-13-en-1-yl acetate, and (Z)-octadec-15-en-1-yl acetate.

In some embodiments, the method for synthesizing the fatty olefin metathesis product according to Formula I comprises reducing an unsaturated fatty acid according to Formula IIa to form an alkenol according to Formula II, contacting an acylating agent with an alkenol according to Formula II to form an olefin metathesis reaction partner according to Formula III, and contacting the olefin metathesis reaction partner of Formula III with an internal olefin according to Formula IV, wherein the unsaturated fatty acid according to Formula IIa is (Z)-octadec-9-enoic acid; the alkenol according to Formula II is (Z)-ocladec-9-en-1-ol; the olefin metathesis reaction partner according to Formula III is (Z)-octadec-9-en-1-yl acetate; the internal olefin according to Formula IV is (Z)-dec-5-ene; and the fatty olefin metathesis product according to Formula I is (Z)-tetradec-9-en-1-yl acetate.

In some embodiments, the method for synthesizing the fatty olefin metathesis product according to Formula I comprises reducing an unsaturated fatty acid according to Formula IIa to form an alkenol according to Formula II contacting an acylating agent with an alkenol according to Formula II to form an olefin metathesis reaction partner according to Formula III, and contacting the olefin metathesis reaction partner of Formula III with an internal olefin according to Formula IV, wherein the unsaturated fatty acid according to Formula IIa is (Z)-octadec-9-enoic acid; the alkenol according to Formula II is (Z)-octadec-9-en-1-ol; the olefin metathesis reaction partner according to Formula III is (Z)-octadec-9-en-1-yl acetate; the internal olefin according to Formula IV is (Z)-hex-3-ene; and the fatty olefin metathesis product according to Formula I is (Z)-dodec-9-en-1-yl acetate.

In some embodiments, the method for synthesizing the fatty olefin metathesis product according to Formula I comprises reducing an unsaturated fatty acid according to Formula IIa to form an alkenol according to Formula II, contacting an acylating agent with an alkenol according to Formula II to form an olefin metathesis reaction partner according to Formula III, and contacting the olefin metathesis reaction partner of Formula III with an internal olefin according to Formula IV, wherein the unsaturated fatty acid according to Formula IIa is (Z)-icos-11-enoic acid; the alkenol according to Formula II is (Z)icos-11-en-1-ol; the olefin metathesis reaction partner according to Formula III is (Z)-icos-11-en-1-yl acetate; the internal olefin according to Formula IV is (Z)-hex-3-ene; and the fatty olefin metathesis product according to Formula I is (Z)-tetradec-11-en-1-yl acetate.

(Z)-Metatbesis Products Front (E)-Reaction Partners and Olefins

The methods described herein are used to prepare fatty olefin metathesis products of Formula I from metathesis reaction partners and olefins, wherein the fatty olefin metathesis products are substantially in the Z-configuration and the metathesis reaction partners and/or olefins comprise isomers in the E-configuration. In some embodiments, fatty olefin metathesis products comprising more than 97% of the Z-isomer are formed according to the methods described herein, wherein the metathesis reaction partners comprise 1%, or more of the E-isomer and the olefins comprise from 0% to 15%, or more, of the E-isomer.

Accordingly, in some embodiments, the invention provides a method for synthesizing a fatty olefin metathesis product according to Formula I:

(I)

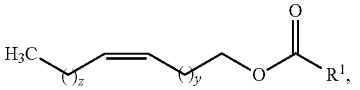

wherein the method includes contacting an olefin metathesis reaction partner according to Formula III (III)

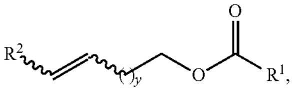

with an internal olefin according to Formula IV (IV)

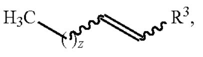

in the presence of a Z-selective ruthenium catalyst or a Z-selective osmium catalyst to form the fatty olefin metathesis product; wherein:

$R^1$ is selected from the group consisting of H and $C_{1-6}$ alkyl;

$R^2$ is selected from the group consisting of $C_{1-18}$ alkyl and $C_{2-18}$ alkenyl;

$R^3$ is $C_{1-18}$ alkyl;

subscript y is an integer ranging from 0 to 17;

subscript z is an integer ranging from 0 to 17; and the fatty olefin metathesis product is at least 97% Z.

In some embodiments, the method for synthesizing a fatty olefin metathesis product according to Formula I:

(I)

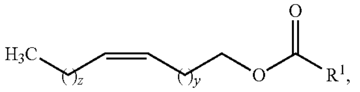

comprises contacting an acylating agent with an alkenol according to Formula II (II)

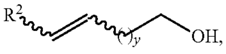

to form an olefin metathesis reaction partner according to Formula III (III)

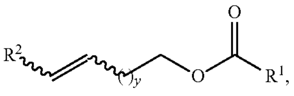

and contacting the olefin metathesis reaction partner with an internal olefin according to Formula IV (IV)

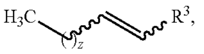

in the presence of a Z-selective ruthenium catalyst or a Z-selective osmium catalyst to Conn the fatty olefin metathesis product; wherein:

$R^1$ is selected from the group consisting of H and $C_{1-6}$ alkyl;

$R^2$ is selected from the group consisting of $C_{1-18}$ alkyl and $C_{2-18}$ alkenyl;

$R^3$ is $C_{1-18}$ alkyl;

subscript y is an integer ranging from 0 to 17;

subscript z is an integer ranging from 0 to 17; and the fatty olefin metathesis product is at least 97% Z.

In some embodiments, the method for synthesizing a fatty olefin metathesis product according to Formula I:

(I)

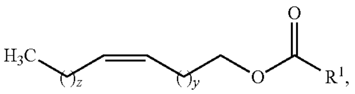

comprising reducing an unsaturated fatty carboxyl derivative according to Formula IIa (IIa)

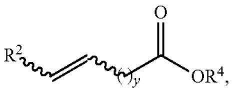

to form an alkenol according to Formula II (II)

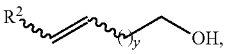

contacting an acylating agent with the alkenol to form an olefin metathesis reaction partner according to Formula III (III)

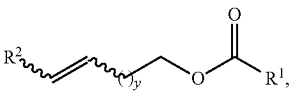

and contacting the olefin metathesis reaction partner with an internal olefin according to Formula IV (IV)

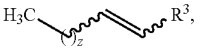

in the presence of a Z-selective ruthenium catalyst or a Z-selective osmium catalyst to form the fatty olefin metathesis product; wherein:

$R^1$ is selected from the group consisting of H and $C_{1-6}$ alkyl;

$R^2$ is selected from the group consisting of $C_{1-18}$ alkyl and $C_{2-18}$ alkenyl;

$R^3$ is $C_{1-18}$ alkyl;

$R^4$ is selected from the group consisting of H and $C_{1-8}$ alkyl;

subscript y is an integer ranging from 0 to 17;

subscript is an integer ranging from 0 to 17; and the fatty olefin metathesis product is at least 97% Z.

In some embodiments, the methods described herein are used to prepare a fatty olefin metathesis product according to Formula I, wherein the fatty olefin, metathesis product is greater than 97% Z. In some embodiments, the fatty olefin metathesis product of Formula I is about 97.1% Z to about 99.9% Z. In some embodiments, the fatty olefin metathesis product of Formula I is about 97.2% Z, 97.4% Z, 97.5% Z, 97.6% Z, 97.8% Z, 97.9% Z, 98.0% Z, 98.1% Z, 98.2% Z, 98.4% Z, 98.5% Z, 98.6% Z, 98.8% Z, 98.9% Z, 99.0% Z, 99.1% Z, 99.2% Z, 99.3% Z, 99.4% Z, 99.5% Z, 99.6% Z, 99.7% Z, 99.8% Z, or about 99.9% Z. In some embodiments, the fatty olefin metathesis product of Formula I is more than 98% Z. In some embodiments, the fatty olefin metathesis product of Formula I is more than 99% Z. In some embodiments, the fatty olefin metathesis product of Formula I is about 99.1% Z, 99.2% Z, 99.3% Z. 99.4% Z, 99.5% Z, 99.6% Z, 99.7% Z, 99.8% Z, about 99.9% Z, or about 100.0% Z.

Accordingly, the invention provides methods for synthesizing a fatty olefin metathesis product according to Formula I as described herein wherein the fatty olefin metathesis product is selected from the group comprising (Z)-tetradec-9-en-1-yl acetate, (Z)-hexadec-11-en-1-yl acetate, (Z)-octadec-13-en-1-yl acetate, (Z)-icos-15-en-1-yl acetate (Z)-tridec-9-en-1-yl acetate, (Z)-pentadec-11-en-1-yl acetate, (Z)-heptadec-13-en-1-yl acetate, (Z)-nonadec-15-en-1-yl acetate, (Z)-dodec-9-en-1-yl acetate, (Z)-tetradec-11-en-1-yl acetate, (Z)-hexadec-13-en-1-yl acetate, (Z)-octadec-15-en-1-yl acetate, or mixtures thereof, wherein the fatty olefin metathesis product is at least 97% Z, more than 98% Z, or more than 99% Z.

In some embodiments, the fatty olefin metathesis product comprises at least one member selected from the group consisting of (Z)-tetradec-9-en-1-yl acetate, (Z)-hexadec-11-en-1-yl acetate, (Z)-octadec-13-en-1-yl acetate, and (Z)-icos-15-en-1-yl acetate, wherein the fatty olefin metathesis product is at least 97% Z, more than 98% Z, or more than 99% Z. In some embodiments, the fatty olefin metathesis product comprises at least one member selected from the group consisting of (Z)-tridec-9-en-1-yl acetate, (Z)-pentadec-11-en-1-yl acetate, (Z)-heptadec-13-en-1-yl acetate, and (Z)-nonadec-15-en-1-yl acetate, wherein the fatty olefin metathesis product is at least 97% Z, more than 98% Z, or more than 99% Z. In some embodiments, the fatty olefin metathesis product comprises at least one member selected from the group consisting of (Z)-dodec-9-en-1-yl acetate, (Z)-tetradec-11-en-1-yl acetate, (Z)-hexadec-13-en-1-yl acetate, and (Z)-octadec-15-en-1-yl acetate, wherein the fatty olefin metathesis product is at least 97% Z, more than 98% Z, or more than 99% Z.

In some embodiments, the fatty olefin metathesis product is selected from the group consisting of (Z)-tetradec-9-en-1-yl acetate, (Z)-dodec-9-en-1-yt acetate, and (Z)-tetradec-11-en-1-yl acetate, wherein the fatty olefin metathesis product is at least 97% Z, more than 98% Z, or more than 99% Z. In some embodiments, the fatty olefin metathesis product is (Z)-tetradec-9-en-1-yl acetate, wherein (Z)-tetradec-9-en-1-yl acetate is at least 97% Z, more than 98% Z, or more than 99% Z. Its some embodiments, the fatty olefin metathesis product is (Z)-dodec-9-en-1-yl acetate, wherein (Z)-dodec-9-en-1-yl acetate is at least 97% Z, more than 98% Z, or more than 99% Z. In some embodiments, the fatty olefin metathesis product is (Z)-tetradec-11-en-1-yl acetate, wherein (Z)-tetradec-11-en-1-yl acetate is at least 97% Z, more than 98% Z, or more than 99% Z.

In some embodiments, the fatty olefin metathesis product according to Formula I is at least 97% Z, more than 98% Z, or more than 99% Z, wherein one or more of the unsaturated fatty carboxyl derivative of Formula IIa, alkenol of Formula II, olefin metathesis reaction partner of Formula III, and/or olefin of Formula IV is at least 1% E. In some embodiments, one or more of the unsaturated fatty carboxyl derivative of Formula IIa, alkenol of Formula II, olefin metathesis reaction partner of Formula III, and/or olefin of Formula IV is about 1.5% E to about 50% E. In some embodiments, the fatty olefin metathesis product according to Formula I is at least 97% Z, more than 98% Z, or more than 99% Z, and one or more of the unsaturated fatty carboxyl derivative of Formula IIa, alkenol of Formula II, olefin metathesis reaction partner of Formula III, and/or olefin of Formula IV is about 1.5% E, about 3.0% E, about 5.0% E, about 8.0% E, about 10% E, about 15% E, about 20% E, about 25% E, about 30% E, about 35% E, about 40% E, about 45% E or about 50% E. In some embodiments, one or more oldie unsaturated fatty carboxyl derivative of Formula IIa, alkenol of Formula II, olefin metathesis reaction partner of Formula III, and/or olefin of Formula IV is about 1.5% E to about 45% E, about 3.0% E to about 40% E, about 5.0% E to about 35% E, about 8.0% E to about 30% E, about 10% E to about 25% E, or about 15% E to about 20% E. In some embodiments, the (trans:cis) ratio of one or more of the unsaturated fatty carboxyl derivative of Formula IIa, alkenol of Formula II, olefin metathesis reaction partner of Formula III, and/or olefin of Formula IV is about 1:30, about 1:20, about 1:10, about 1:6, about 1:4, about 1:3, about 1:2.5, about 1:2, about 1:1.5, about 1:1.2; or about 1:1.

In some embodiments, the fatty olefin metathesis product according to Formula I is at least 97% Z, more than 98% Z, or more than 99% Z, wherein the olefin metathesis reaction partner of Formula III is at least 1% E. In some embodiments, the fatty olefin metathesis product according to Formula I is at least 97% Z, more than 98% Z, or more than 99% Z, and the olefin metathesisreaction partner of Formula III is about 1.5% E to about 50% E. In some embodiments, the fatty olefin metathesis product according to Formula I is at least 97% Z, more than 98% Z, or more than 99% Z, and the olefin metathesis reaction partner of Formula III is about 1.5% E, about 30% E, about 50% E, about 80% E, about 10% E, about 15% E, about 20% E, about 25% E, about 30% E, about 35% E, about 40% E, about 45% E, or about 50% E. In some embodiments, the fatty olefin metathesis product according to Formula I is at least 97% Z, more than 98% Z, or more than 99% Z, and the olefin metathesis reaction partner of Formula III is about 1.5% E to about 45% E, about 3.0% E to about 40% E, about 5.0% E to about 35% E, about 8.0% E to about 30% E, about 10% E to about 25% E, or about 15% E to about 20% E. In some embodiments, the E:Z (trans:cis) ratio of the olefin metathesis reaction partner of Formula III is about 1:30, about 1:20, about 1:10, about 1:6, about 1:4, about 1:3, about 1:2.5, about 1:2, about 1:1.5, about 1:1.2, or about 1:1, and the fatty olefin metathesis product according to Formula I is at least 97% Z, more than 98% Z, or more than 99% Z.

As such, in some embodiments, the fatty olefin metathesis product of Formula I prepared according to any of the methods described herein is at least 97% Z, more than 98% Z, or more than 99% Z, and the olefin metathesis reaction partner of Formula III is selected from the group comprising, octadec-9-en-1-yl acetate, icos-11-en-1-yl acetate, docos-13-en-1-yl acetate, tetracos-15-en-1-yl acetate, or mixtures thereof, wherein the olefin metathesis reaction partner is about 8.0% to about 30% E, about 10% to about 25% E, or about 15% to about 20% E. In some embodiments, the fatty olefin metathesis product of Formula I is at least 97% Z, more than 98% Z, or more than 99% Z, and the olefin metathesis reaction partner consists of octadec-9-en-1-yl acetate and at least one member selected from the group consisting of icos-11-en-1-yl acetate, docos-13-en-1-yl acetate, and tetracos-15-en-1-yl acetate, wherein the olefin metathesis reaction partner is about 8.0% to about 30% E, about 10% to about 25% E, or about 15% to about 20% E. In some embodiments, the fatty olefin metathesis product of Formula I is at least 97% Z, more than 98% Z, or more than 99% Z, and the olefin metathesis reaction partner is selected from the group consisting of octadee-9-en-1-yl acetate, icos-11-en-1-yl acetate, docos-13-en-1-yl acetate, and tetracos-15-en-1-yl acetate, wherein the olefin metathesis reaction partner is about 8.0% to about 30% E, about 10% to about 25% E, or about 15% to about 20% E.

In some embodiments, the fatty olefin metathesis product of Formula I is at least 97% Z, more than 98% Z, or more than 99% Z, and the olefin metathesis reaction partner of Formula III is octadec-9-en-1-yl acetate, wherein the octadec-9-en-1-yl acetate is about 8.0% to about 30% E, about 10% to about 25% E, or about 15% to about 20% E. In some embodiments, the fatty olefin metathesis product of Formula I is at least 97% Z, more than 98% Z, or more than 99% Z, and the olefin metathesis reaction partner is icos-11-en-1-yl acetate, wherein the icos-11-en-1-yl acetate is about 8.0% to about 30% E, about 10% to about 25% E, or about 15% to about 20% E. In some embodiments, the fatty olefin metathesis product of Formula I is at least 97% Z, more than 98% Z, or more than 99% Z, and the olefin metathesis reaction partner is docos-13-en-1-yl acetate, wherein the docos-13-en-1-yl acetate is about 8.0% to about 30% E, about 10% to about 25% E, or about 15% to about 20% E. In some embodiments, the fatty olefin metathesis product of Formula I is at least 97% Z, more than 98% Z, or more than 99% Z, and the olefin metathesis reaction partner is tetracos-15-en-1-yl acetate, wherein the tetracos-15-en-1-yl acetate is about 8.0% to about 30% E, about 10% to about 25% E, or about 15% to about 20% E.

In some embodiments, the fatty olefin metathesis product according to Formula I is at least 97% Z, more than 98% Z, or more than 99% Z, wherein the olefin of Formula IV is at least 1% E. In some embodiments, the fatty olefin metathesis product according to Formula I is at least 97% Z, more than 98% Z, or more than 99% Z, and the olefin of Formula IV is about 1.5% E to about 50% E. In some embodiments, the fatty olefin metathesis product according to Formula I is at least 97% Z, more than 98% Z, or more than 99% Z, and the olefin of Formula IV is about 1.5% E, about 3.0% E, about 5.0% E, about 8.0% E about 10% E, about 15% E, about 20% E, about 25% E, about 30% if about 35% E, about 40% E, about 45%, or about 50% E. In some embodiments, the fatty olefin metathesis product according to Formula I is at least 97% Z, more than 98% Z, or more than 99% Z, and the olefin of Formula IV is about 1.5% E to about 45% E, about 3.0% E to about 40% E, about 5.0% E to about 35% E, about 8.0% E to about 30% E, about 10% E to about 25% E, or about 15% E to about 20% E. In some embodiments, the E:Z (trans:cis) ratio of the olefin of Formula IV is 1:30, about 1:20, about 1:10, about 1:6, about 1:4, about 1:3, about 1:2.5, about 1:2, about 1:1.5, about 1:1.2, or about 1:1, and the fatty olefin metathesis product according to Formula I is at least 97% Z, more than 98% Z, or more than 99% Z.

As such, in some embodiments, the fatty olefin metathesis product of Formula I prepared according to any of the methods described herein is at least 97% Z, more than 98% Z, or more than 99% Z, and the olefin of Formula IV is selected from the group comprising hexadec-8-ene, tetradec-7-ene, dodec-6-ene, dec-5-ene, oct-4-ene, or hex-3-ene, wherein the olefin is about 8.0% to about 30% E, about 10% to about 25% E or about 15% to about 20% E. In some embodiments, the fatty olefin metathesis product of Formula I is at least 97% Z, more than 98% Z, or more than 99% Z, and the olefin is selected from the group consisting of hexadec-8-ene, tetradec-7-ene, dodec-6-ene, dec-5-ene, oct-4-ene, and hex-3-ene, wherein the olefin is about 8.0% to about 30% E, about 10% to about 25% E, or about 15% to about 20% E. In some embodiments the fatty olefin metathesis product of Formula I is at least 97% Z, more than 98% Z, or more than 99% Z, and the olefin is selected from the group consisting of tetradec-7-ene, dodec-6-ene, dec-5-ene, oct-4-ene, and hex-3-ene, wherein the olefin is about 8.0% to about 30% E, about 10% to about 25% E, or about 15% about 20% E.

In some embodiments, the fatty olefin metathesis product of Formula I is at least 97% Z, more than 98% Z, or more than 99% Z, and the olefin of Formula IV is selected from the group consisting of dodec-6-ene, dec-5-ene, oct-4-ene, and hex-3-ene, wherein the olefin is about 8.0% to about 30% E, about 10% to about 25% E, or about 15% to about 20% E. In some embodiments, the fatty olefin metathesis product of Formula I is at least 97% Z, more than 98% Z, or more than 99% Z, and the olefin is selected from the group consisting of dec-5-ene, oct-4-ene, and hex-3-eue, wherein the olefin is about 8.0% to about 30% E, abont 10% to about 25% E or about 15% to about 20% E. In some embodiments, the fatty olefin metathesis product of Formula I is at least 97% Z, more than 98% Z, or more than 99% Z, and the olefin is dec-5-ene, wherein dec-5-ene is about 8.0% to about 30% E, about 10% to about 25% E, or about 15% to about 20% E. In some embodiments, the fatty olefin metathesis product of Formula I is at least 97% Z, more than 98% Z, or more than 99% Z, and the olefin is oct-4-ene, wherein oct-4-ene is about 8.0% to about 30% E, about 10% to about 25% E, or about 15% to about 20% E. In some embodiments, the fatty olefin metathesis product of Formula I is at least 97% Z, more than 98% Z, or more than 99% Z, and the olefin is hex-3-ene,k wherein hex-3-ene is about 8.0% to about 30% E, about 10% to about 25% E, or about 15% to about 20% E.

In some embodiments, the fatty olefin metathesis product according to Formula I is at least 97% Z, more than 98% Z, or more than 99% Z, wherein the alkenol of Formula II is at least 1% E. In some embodiments, the fatty olefin metathesis product according to Formula I is at least 97% Z, more than 98% Z, or more than 99% Z, and the alkenol of Formula II is about 1.5% E to about 50% E. In some embodiments, the fatty olefin metathesis product according to Formula I is ar least 97% Z, more than 98% Z, or more than 99% Z, and the alkenol of Formula II is about 1.5% E, about 3.0% E, about 5.0% E, about 8.0% E, about 10% E, about 15% E, about 20% E, about 25% E, about 30% E, about 35% E, about 40% E, about 45%, or about 50% E. In some embodiments, the fatty olefin metathesis product according to Formula I is at least 97% Z, more than 98% Z, or more than 99% Z, and the alkenol of Formula II is about 1.5% E to about 45%, about 3.0% E to about 40% E, about 5.0% E to about 35% E, about 8.0% E to about 30% E, about 10% E to about 25% E, or about 15% E to about 20% E. In some embodiments, the E:Z (trans:cis) ratio of the alkenol of Formula II, is about 1:30, about 1:20, about 1:10, about 1:6, about 1:4, about 1:3, about 1:2.5, about 1:2, about 1:1.5, about 1:1.2, or about 1:1, and the fatty olefin metathesis product according to Formula I is at least 97% Z, more than 98% Z, or more than 99% Z.

Accordingly, in some embodiments the fluty olefin metathesis product of Formula I prepared according to any of the methods described herein is at least 97% Z, more than 98% Z, or more than 99% Z, and the alkenol of Formula II is selected from the group comprising octadec-9-en-1-ol, icos-11-en-1-ol, docos-13-en-1-ol, tetracos-15-en-ol, or mixtures thereof, wherein the alkenol is about 8.0% to about 30% E, about 10% to about 25% E, or about 15% to about 20% E. In some embodiments, the fatty olefin metathesis product of Formula I is at least 97% Z, more than 98% Z, or more than 99% Z, and the alkenol as selected from the group consisting of octadec-9-en-1-ol, icos-11-en-1-ol, docos-13-en-1-ol, and tetracos-15-en-ol, wherein the alkenol is about 8.0% to about 30% E, about 10% to about 25% E, or about 15% to about 70% E.

In some embodiments, the fatty olefin metathesis product of Formula I is at least 97% Z, more than 98% Z, or more than 99% Z and the alkenol of Formula II is octadec-9-en-1-ol, wherein octadec-9-en-1-ol is about 8.0% to about 30% E, about 10% to about 25% E, or about 15% to about 20% E. In some embodiments, the fatty olefin metathesis product of Formual I is at least 97% Z, more than 98% Z, or more than 99% Z, and the alkenol is icos-11-en-1-ol, wherein icos-11-en-1-ol is about 8.0% to about 30% E, about 10% to about 25% E, or about 15% to about 20% E. In some embodiments, the fatty olefin metathesis product of Formula I is at least 97% Z, more than 98% Z, or more than 99% Z, and the alkenol is docos-13-en-1-ol, wherein docos-13-en-1-ol is about 8.0% to about 30% E, about 10% to about 25% E, or about 15% to about 20% E. In some embodiments, the fatty olefin metathesis product of Formula I is at least 97% Z, more than 98% Z, or more than 99% Z, and the alkenol tetracos-15-en-ol, wherein tetracos-15-en-ol is about 8.0% to about 30% E, about 10% to about 25% E, or about 15% to about 20% E.

In, some embodiments, the fatty olefin metathesis product according to Formula I is at least 97% Z, more than 98% Z, or more than 99% Z, wherein the unsaturated fatty carboxyl derivative of Formula IIa is at least 1% E. In some embodiments, the fatty olefin metathesis product according to Formula I is at least 97% Z, more than 98% Z, or more than 99% Z, and the unsaturated fatty carboxyl derivative of Formula IIa is about 1.5% E to about 50% E. In some embodiments, the fatty olefin metathesis product according to Formula I is at least 97% Z, more than 98% Z, or more than 99% Z, and the unsaturated fatty carboxyl derivative of Formula IIa is about 1.5% E, about 3.0% E, about 5.0% E, about 8.0% E, about 10% E, about 15% E, about 20% E, about 25% E, about 30% E, about 35% E, about 40% E, about 45%, or about 50% E. In some embodiments, the fatty olefin metathesis product according to Formula I is at least 97% Z, more than 98% Z, or more than 99% Z, and the unsaturated fatty carboxyl derivative of Formula IIa is about 1.5% E to about 45%, about 3.0% E to about 40% E, about 5.0% E to about 35% E, about 8.0% E to about 30% E, about 10% E to about 25% E, or about 15% E to about 20% E. In some embodiments, the E:Z (trans:cis) ratio of the unsaturated fatty carboxyl derivative of Formula IIa is about 1:30, about 1:20, about 1:10, 1:6, about 1:4, about 1:3, about 1:2.5, about 1:2, about 1:1.5, about 1:1.2, or about 1:1, and the fatty olefin metathesis product according to Formula I is at least 97% Z, more than 98% Z, or more than 99% Z.

As such, in some embodiments, the fatty olefin metathesis product of Formula I prepared according to any of the methods described herein is at least 97% Z, more than 98% Z, or more than 99% Z, and the unsaturated fatty acid alkyl ester of Formula IIa is selected from the group comprising methyl octadec-9-enoate, methyl icos-11-enoate, methyl docos-13-enoate, methyl tetracos-15-enoate, or mixtures thereof, wherein the unsaturated fatty acid alkyl ester is about 8.0% to about 30% E, about 10% to about 25% E, or about 15% to about 20% E. In some embodiments, the fatty olefin metathesis product of Formula I is at least 97% Z, more than 98% Z, or more than 99% Z, and the unsaturated fatty acid alkyl ester consists of methyl octadec-9-enoate and at least one member selected from the group consisting of methyl icos-11-enoate, methyl docos-13-enoate, and methyl tetracos-15-enoate, wherein the unsaturated fatty acid alkyl ester is about 8.0% to about 30% E, about 10% to about 25% E, or about 15% to about 20% E. In some embodiments, the fatty olefin metathesis product of Formula I is at least 97% Z, or more than 98% Z, or more than 99% Z, and the unsaturated fatty acid alkyl ester is selected from the group consisting of methyl octadec-9-enoate, methyl icos-11-enoate, methyl docos-13-enoate, and methyl tetracos-15-enoate, wherein the unsaturated fatty acid alkyl ester is about 8.0% to about 30% E, about 10% to about 25% E, or about 15% to about 20% E.

In some embodiments, the fatty olefin metathesis product of Formula I is at least 97% Z, more than 98% Z, or more than 99% Z, and the unsaturated fatty acid alkyl ester of Formula IIa is methyl octadec-9-enoate, wherein methyl octadec-9-enoate is about 8.0% to about 30% E, about 10% to about 25% E, or about 15% to about 20% E. In some embodiments, the fatty olefin metathesis product of Formula I is at least 97% Z, more than 98% Z, or more than 99% Z, and the unsaturated fatty acid alkyl ester is methyl icos-11-enoate, wherein methyl icos-11-enoate is about 8.0% to about 30% E, about 10% to about 25% E, or about 15% to about 20% E. In some embodiments, the fatty olefin metathesis product of Formula I is at least, 97% Z, more than 98% Z, or more than 99% Z, and the unsaturated fatty acid alkyl ester is methyl docos-13-enoate, wherein methyl docos-13-enoate is about 8.0% to about 30% E, about 10% to about 25% E, or about 15% to about 20% E. In some embodiments, the fatty olefin metathesis product of Formula I is at least 97% Z, more than 98% Z, or more than 99% Z, and the unsaturated fatty acid alkyl ester is methyl tetracos-15-enoate, wherein methyl tetracos-15-enoate is about 8.0% to about 30% E, about 10% to about 25% E, or about 15% to about 20% E.

As such, in some embodiments, the fatty olefin metathesis product of Formula I prepared according to any of the methods described herein is at least 97% Z, more than 98% Z, or more than 99% Z, and the unsaturated fatty acid according to Formula IIa is selected from the group comprising octadec-9-enoic acid, icos-11-enoic acid, docos-13-enoic acid, tetracos-15-enoic acid, or mixtures thereof, wherein the unsaturated fatty acid is about 8.0% to about 30% E, about 10% to about 25% E, or about 15% to about 20% E. In some embodiments, the fatty olefin metathesis product of Formula I is at least 97% Z, more than 98% Z, or more than 99% Z, and the unsaturated fatty acid consists of octadec-9-enoic acid and at least one member selected from the group consisting of icos-11-enoic acid, doors-13-enoic acid, and tetracos-15-enoic acid, wherein the unsaturated fatty acid is about 8.0% to about 30% E, about 10% to about 25% E, or about 15% to about 20% E. In some embodiments, the fatty olefin metathesis product of Formula I is at least 97% Z, more an 98% Z, or more than 99% Z, and the unsaturated fatty acid is selected from the group consisting of octadec-9-enoic acid, icos-11-enoic acid, docos-13-enoic acid, and tetracos-15-enoic acid, wherein the unsaturated fatty acid is about 8.0% to about 30% E, about 10% to about 25% E, or about 15% to about 20% E.

In some embodiments, the fatty olefin metathesis product of Formula I is at least 97% Z, more than 98% Z, or more than 99% Z, and the unsaturated fatty acid of Formula IIa is octadec-9-enoic acid, wherein octadec-9-enoic acid is about 8.0% to about 30% E, about 10% to about 25% E, or about 15% to about 20% E. In some embodiments, the fatty olefin metathesis product of Formula I is at least 97% Z, more than 98% Z, or more than 99% Z, and the unsaturated fatty acid is icos-11-enoic acid, wherein icos-11-enoic acid is about 8.0% to about 30% E, about 10% to about 25% E, or about 15% to about 20% E. In some embodiments, the fatty olefin metathesis product of Formula I is at least 97% Z, more than 98% Z, or more than 99% Z, and the unsaturated fatty acid is docos-13-enoic acid, wherein docos-13-enoic acid is about 8.0% to about 30% E, about 10% to about 25% E, or about 15% to about 20% E. In some embodiments, the fatty olefin metathesis product of Formula I is at least 97% Z, more than 98% Z, or more than 99% Z, and the unsaturated fatty acid is tetracos-15-enoic acid, wherein tetracos-5-enoic acid is about 8.0% to about 30% E, about 10% to about 25% E, or about 15% to about 20% E.

Metathesis Catalysts

In some embodiments, the metathesis catalyst used in the methods for synthesizing fatty olefin metathesis products as described above is a Z-selective metathesis catalyst having a structure according to Formula V:

(V)

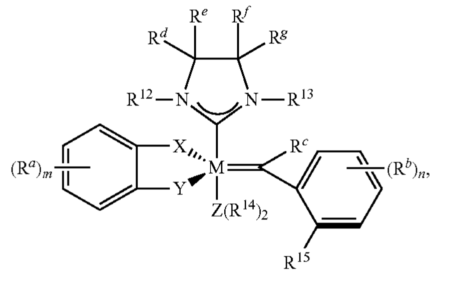

wherein:

M is selected from the group consisting of ruthenium and osmium;

X and Y are independently selected from the group consisting of S and O;

Z is selected from the group consisting of O and S(═O);

each subscript m and subscript n is an integer independently selected from 0, 1, 2, 3, and 4;

each $R^a$ is independently selected front from the group consisting of halogen, $C_1$-$C_6$ alkyl, aryl, and heteroaryl; or one $R^a$ is taken together with an adjacent $R^a$ to form an unsubstituted or substituted bicyclic ring, or an unsubstituted or substituted polycyclic ring;

each $R^b$ is independently selected from the group consisting of halogen, $C_1$-$C_6$ alkyl, alkoxy, aryl and heteroaryl; or one $R^b$ is taken together with an adjacent $R^b$ to form an unsubstituted or substituted bicyclic ring, or an unsubstituted or substituted polycyclic ring;

$R^c$ is selected from the group consisting of hydrogen and $C_1$-$C_6$ alkyl;

each $R^d$, $R^e$, $R^f$, and $R^g$ is independently selected from the group consisting of hydrogenand $C_1$-$C_6$ alkyl;

$R^{12}$ and $R^{13}$ are independently selected from the group consiting of 2,4,6-tri-iso-propylphenyl, 2,6-di-iso-propylphenyl, 2,6-di-adamantylphenyl, 2-iso-propyl-6-tert-butylphenyl, 2,4,6-tri-tert-butylphenyl, and 2,6-di-tert-butylphenyl;

each $R^{14}$ is independently selected from the group consisting of hydrogen, methyl, ethyl, n-propyl, iso-propyl, n-butyl, tert-butyl, cyclobexyl, bentyl, and phenyl; and $R^{15}$ is selected from the group consisting of hydrogen, halogen, and $C_1$-$C_6$ alkyl, or $R^{15}$ and one $R^{14}$ are taken together to form a bond.

In some embodiments, the Z-selective metathesis catalyst has the structure of Formula V, wherein: M is ruthenium; X and Y are S; Z is selected from the group consisting of O and S(═O); subscript m is 2; subscript n is 0; each $R^a$ is independently selected from the group consisting of halogen, $C_1$-$C_6$ alkyl, and aryl; $R^c$ is hydrogen, each $R^d$, $R^e$, $R^f$, and $R^g$ is hydrogen; $R^{12}$ and $R^{13}$ are independently selected from the group consisting of 2,4,6-tri-iso-propylphenyl, 2,6-di-iso-propylphenyl, 2,6-di-adamantylphenyl, 2-iso-propyl-6-tert-butylphenyl, 2,4,6-tri-tert-butylphenyl, and 2,6-di-tert-butylphenyl; each $R^{14}$ is independently selected from the group consisting of methyl, iso-propyl, benzyl, and tert-butyl; and $R^{15}$ is selected from the group consisting of hydrogen, halogen, and $C_1$-$C_6$ alkyl, or $R^{15}$ and one $R^{14}$ are taken together to form a bond.

In some embodiments, the metathesis catalyst used in the methods for synthesizing a fatty olefin metathesis product of Formula I is a Z-selective metathesis catalyst selected from the group consisting of:

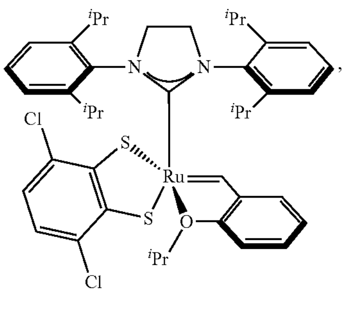,

-continued

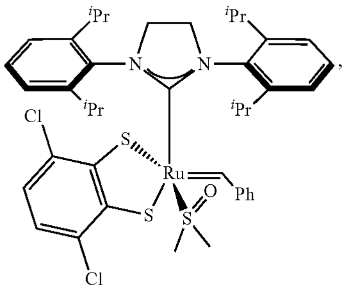

, and

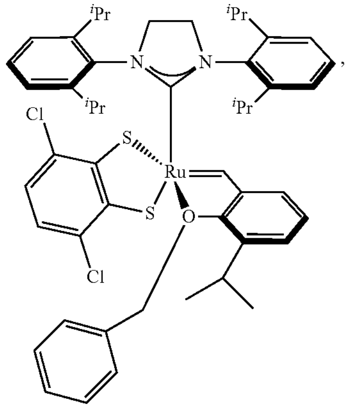

,

In some embodiments, the catalyst is:

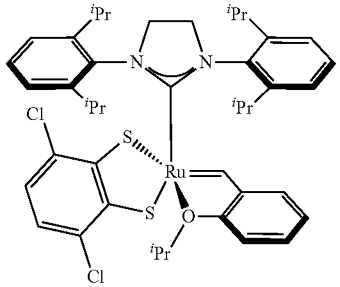

or

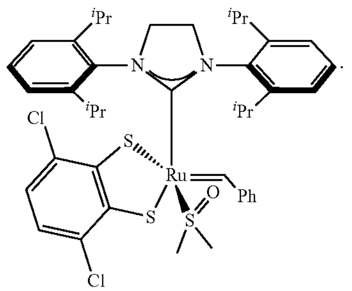

.

Other catalysts useful in the methods provided herein include, but are not limited to, those set forth in WO 2018/191373, WO 2018/038928, WO 2018/034931, WO 2017/100585, and U.S. Pat. Nos. 10,857,350; 10,774,035; 9,938,253; and 6,921,735, which are incorporated herein by reference in their entirety. Catalysts described by Zachmann et al. (*Chem. Eur. J.* 2021, 27, 7663-7666) and Grudezień et al, (*Chem. Eur. J.* 2014, 20,2819-2828) may also be employed.

Metathesis Reaction Conditions

The Z-selective metathesis catalyst is typically provided in the reaction mixture in a sub-stoichiometric amount (e.g., catalytic amount), in certain embodiments, that amount is in the range of about 0.001 to about 50 mol % (0.1-5000 ppm) with respect to the limiting reagent of the chemical reaction, depending upon which reagent is in stoichiometric excess. In some embodiment, the catalyst is present in less than or equal to about 40 mol % relative to the limiting reagent. In some embodiments, the catalyst is present in less than or equal to about 30 mol % relative to the limiting reagent. In some embodiments, the catalyst is present in less than about 20 mol %, less than about 10 mol %, less than about 5 mol less than about 2.5 mol %, less than about 1 mol %, less than about 0.5 mol %, less than about 0.1 mol %, less than about 0.015 mol %, less than about 0.01 mol %, less than about 0.0015 mol or less, relative to the limiting reagent. In some embodiments, the catalyst is present in the range of about 2.5 mol % to about 5 mol %, relative to the limiting reagent. In some embodiments, the reaction mixture contains about 0.01-0.1 mol % catalyst (e.g., 0.5 mol % catalyst). In the case where the molecular formula of the catalyst complex includes more than one metal, the amount of the catalyst complex used in the reaction may be adjusted accordingly.

Catalyst loading can also be expressed in relation to the olefin content of the reaction mixture. For example, the metathesis catalyst may be present in an amount ranging from about 0.1 ppm to about 500 ppm, based on the total number of double bonds in the reaction mixture. The reaction mixture may contain 0.1-100 ppm catalyst per double bond, or about 1-100 ppm, or about 1-75 ppm, or about 1-50 ppm, or about 3-50 ppm.

In some cases, the methods described herein can be performed in the absence of solvent (e.g., neat). In some cases, the methods can include the use of one or more solvents, Examples of solvents that may be suitable for use in the invention include, but are not limited to, benzene, p-cresol, toluene, xylene diethyl ether, glycol, diethyl ether, petroleum ether, hexane, cyclohexane, pentane, methylene chloride, chloroform, carbon tetrachloride, dioxane, tetrahydrofuran (THF), dimethyl sulfoxide, dimethylformamide, hexamethyl-phosphoric triamide, ethyl acetate, pyridine, triethylamine, picoline, and the like, as well as mixtures thereof. In some embodiments, the solvent is selected from benzene, toluene, pentane, methylene chloride, and THF. In certain embodiments, the solvent is benzene.

In some embodiments, the method is performed under reduced pressure. This may be advantageous in cases where a volatile byproduct, such as ethylene, may be produced during the course of the metathesis reaction. For example, removal of the ethylene byproduct from the reaction vessel may advantageously Shift the equilibrium of the metathesis reaction towards formation of the desired product. In some embodiments the method is performed at a pressure of about less than 760 torr. In some embodiments, the method is performed at a pressure of about less than 700 torr. In some embodiments, the method is performed at a pressure of about less than 650 torr. In some embodiments, the method is performed at a pressure of about less than 600 torr. In some embodiments, the method is performed at a pressure of about less than 550 torr. In some embodiments, the method is performed at a pressure of about less than 500 torr. In some embodiments, the method is performed at a pressure of about less than 450 torr. In some embodiments, the method is performed at a pressure of about less than 400 torr. In some embodiments, the method is performed at a pressure of about less than 350 torr. In some embodiments, the method is performed at a pressure of about less than 300 torr. In some embodiments, the method is performed at a pressure of about less than 250 torr. In some embodiments, the method is performed at a pressure of about less than 200 torr. In some embodiments, the method is performed at a pressure of about less than 150 torr. In some embodiments, the method is performed at a pressure of about less than 100 torr. In some embodiments, the method is performed at a pressure of about less than 90 torr. In some embodiments, the method is performed at a pressure of about less than 80 torr. In some embodiments, the method is performed at a pressure of about less than 70 torr. In some embodiments, the method is performed at a pressure of about less than 60 torr. In some embodiments, the method is performed at a pressure of about less than 50 torr. In some embodiments, the method is performed at a pressure of about less than 40 torr. In some embodiments, the method is performed at a pressure of about less than 30 torr. In some embodiments, the method is performed at a pressure of about less than 20 torr. In some embodiments, the method is performed at a pressure of about 20 torr.

In some embodiments, the method is performed at a pressure of about 19 torr. In some embodiments, the method is performed at a pressure of about 18 torr. In some embodiments, the method is performed at a pressure of about 17 torr. In some embodiments, the method is performed at a pressure of about 16 torr. In some embodiments, the method is performed at a pressure of about 15 torr. In some embodiments, the method is performed at a pressure of about 14 torr. In some embodiments, the method is performed at a pressure of about 13 torr. In some embodiments, the method is performed at a pressure of about 12 torr. In some embodiments, the method is performed at a pressure of about 11 torr. In some embodiments, the method is performed at a pressure of about 10 torr. In some embodiments, the method is performed at a pressure of about 10 torr. In some embodiments, the method is performed at a pressure of about 9 torr. In some embodiments, the method is performed at a pressure of about 8 torr. In some embodiments, the method is performed at a pressure of about 7 torr. In some embodiments, the method is performed at a pressure of about 6 torr. In some embodiments, the method is performed at a pressure of about 5 torr. In some embodiments, the method is performed at a pressure of about 4 torr. In some embodiments, the method is performed at a pressure of about 3 torr. In some embodiments, the method is performed at a pressure of about 2 torr. In some embodiments, the method is performed at a pressure of about 1 torr. In some embodiments, the method, is performed at a pressure of less than about 1 torr.

In some embodiments, the two metathesis reactants (i.e., metathesis reaction partner and olefin) are present in equimolar amounts. In some embodiments, the two metathesis reactants are not present in equimolar amounts. In certain embodiments, the two reactants are present in a molar ratio of about 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20. In certain embodiments, the two reactants are present in a molar ratio a about 10:1. In certain embodiments, the two reactants are present in a molar ratio of about 7:1. In certain embodiments, the two reactants are present in a molar ratio of about 5:1. In certain embodiments, the two reactants are present in a molar ratio of about 2:1. In certain embodiments the two reactants are present in a molar ratio of about 1:10. In certain embodiments, the two reactants are present m a molar ratio of about 1:7. In certain embodiments, the two reactants are present in a molar ratio of about 1.5. In certain embodiments, the two reactants are present in a molar ratio of 1:2.

In some embodiments, one molar equivalent of the olefin is contacted with one molar equivalent of the olefin metathesis reaction partner. In some embodiments, about 1.5, 2, 2.5, or 3 molar equivalents of the olefin is contacted with one molar equivalent of the metathesis reaction partner. In some embodiments, about 1.5 molar equivalents of the olefin is contacted with one molar equivalent of the metathesis reaction partner.

In general, the reactions with many of the Z-selective metathesis catalysts disclosed herein provide yields better than 15%, e.g., better than 50%, better than 75%, or better than 90%. In addition, the reactants and products are chosen to provide at least a 5° C. difference, e.g., a greater than 20° C. difference, or a greater than 40° C. difference in boiling points. Additionally, the use of Z-selective metathesis catalysts allows for much faster product formation than byproduct, and it can be desirable to run these reactions as quickly as practical. In particular, the reactions are performed in less than about 24 hours, e.g., less than 12 hours, or less than 8 hours, or less than 4 hours. Advantageously, the methods of the invention provide metathesis products on a scale ranging from a few milligrams to hundreds of kilograms or more. For example, the methods can be conducted using around 1-10 grams of the internal olefin according to Formula IV, or around 10-100 grams of the internal olefin according to Formula IV, or around 100-500 grams of the internal olefin according to Formula IV, or around 500-1000 grams of the internal olefin according to Formula IV. The methods can be conducted using at least 1, 5, 10, 25, 50, 100, or 1,000 kilograms of starting material. The metathesis reactions can be conducted using a metathesis reactor as described, for example, in WO 2011/046872, which reactor can be operated in conjunction with one or more downstream separation units for separating and/or recycling particular product or byproduct streams (e.g., an olefin stream, a $C_2$-$C_3$ compound stream, or a $C_3$-$C_5$ compound stream). The metathesis reactor and separation unit(s) can be operated in conjunction with one or more adsorbent beds to facilitate the separation of the metathesized products from the catalyst, as well as washing and drying units for purification of desired products. The reduction, acylation, and metathesis reactions can be conducted to provide products on the scale of metric tons.

One of skill in the art will appreciate that the time, temperature and solvent can depend on each other, and that changing one can require changing the others to prepare the metathesis products in the methods of the invention. The metathesis steps cart proceed at a variety of temperatures and times. In general, reactions in the methods of the invention are conducted using reaction times of several minutes to several days. For example, reaction times of from about 12 hours to about 7 days can be used. In some embodiments, reaction times of 1-5 days can be used. In some embodiments, reaction times of from about 10 minutes to about 10 hours can be used. In general, reactions in the methods of the invention are conducted at a temperature of from about 0° C. to about 200° C. for example, reactions can be conducted at 15-100° C. In some embodiments, reaction can be conducted at 20-80° C. (e.g., 20-60° C.) In some embodiments, reactions can be conducted at 100-150° C.

Olefins, metathesis reaction partners, olefin starting material, olefin-containing reactant, and fatty olefin derivative (e.g., alkenols, unsaturated fatty alcohol acetates, unsaturated fatty ester acetates, olefin metathesis reaction partners, fatty olefin metathesis products, unsaturated fatty aldehydes, unsaturated fatty carboxyl derivatives, metathesis products, etc.) and other materials used in the methods of the invention can be obtained from any suitable source. In some embodiments, the metathesis reaction partners used in the methods of the invention are obtained from a natural oil and/or a derivative thereof (e.g., unsaturated fatty acids described above).

In some embodiments, materials to be reacted in a metathesis reaction—including those derived from natural oils—will contain one or more contaminants with the potential to adversely affect the performance of a metathesis catalyst. Such contaminants can be referred to as "catalyst poisons" or "catalyst poisoning contaminants." The contaminant levels can be reduced according to the methods described herein. In some embodiments, the material comprises a plurality of contaminants and the method comprises reducing levels of two or more of the contaminants. In some embodiments, the material comprises a plurality of contaminants and the method comprises reducing levels of three or more of the contaminants. In some embodiments, the material comprises a plurality of contaminants and the method comprises reducing levels of four or more of the contaminants. In some embodiments, the material comprises a plurality of contaminants and the method comprises reducing levels of five or more of the contaminants.

Representative contaminants include but are not limited to water, peroxides, peroxide decomposition products, hydroperoxides, protic materials, polar materials, Lewis basic catalyst poisons, and the like, and combinations thereof. It is to be understood that some contaminants may properly be classified in multiple categories (e.g., alcohol can be considered both a protic material and a polar material). It is to be further understood that different catalysts may have different susceptibilities to a particular contaminant, and that a contaminant that adversely affects the performance of one catalyst.

Representative protic materials that may be found as contaminants in a substrate that is to be reacted in a metathesis reaction include but are not limited to materials having a hydrogen atom bonded to oxygen (e.g., carboxylic acids, alcohols, and the like) and/or a hydrogen atom bonded to nitrogen (e.g., primary amines, secondary amines, and the like). In some embodiments, particularly though not exclusively in natural oil substrates, a prone material contaminant may comprise a carboxylic acid functional group, a hydroxyl functional group, or a combination thereof. In some embodiments, the protic material is selected from the group consisting of free fatty acids, hydroxyl-containing materials, MAGs, DAGs, and the like, and combinations thereof.

Representative polar materials that may be found as contaminants in a substrate that is to be reacted in a metathesis reaction include but are not limited to heteroatom-containing materials such as oxygenates. In some embodiments, the polar material is selected from the group consisting of alcohols, aldehydes, ethers, and the like, and combinations thereof.

Representative Lewis basic catalyst poisons that may be found as contaminants in a substrate that is to be reacted in a metathesis reaction include but are not limited to heteroatom-comaining materials. In some embodiments, the Lewis basic catalyst poisons are selected from the group consisting of N-containing materials, P-containing materials, S-containing materials, and the like, and combinations thereof.

Reaction materials containing contaminants can be treated with one or more conditioning agents that mitigate potentially adverse effects of one or more of the contaminants. Conditioning agents that can be used in the methods of the invention (individually, or in combination sequentially or simultaneously) include heat, molecular sieves, alumina (aluminum oxide), silica gel, montmorillonite clay, fuller's earth, bleaching clay, diatomaceous earth, zeolites, kaolin, activated metals (e.g., Cu, Mg, and the like), acid anhydrides (e.g., acetic anhydride and the like), activated carbon (i.e., activated charcoal), soda ash, metal hydrides (e.g., alkaline earth metal hydrides such as $CaH_2$ and the like), metal sulfates (e.g., alkaline earth metal sulfates such as calcium sulfate, magnesium sulfate, and the like; alkali metal sulfates such as potassium sulfate, sodium sulfate, and the like; and other metal sulfates such as aluminum sulfate, potassium magnesium sulfate, arid the like), metal halides (e.g., alkali earth metal halides such as potassium chloride and the like), metal carbonates (e.g., calcium carbonate, sodium carbonate, and the like), metal silicates (e.g., magnesium silicate and the like), phosphorous pentoxide, metal aluminum hydrides (e.g., alkali metal aluminum hydrides such as $LiAlH_4$, and the like), alkyl aluminum hydrides (e.g., DIBALH), metal borohydrides (e.g., alkali metal borohydrides such as $LiBH_4$, $LiBH_4$, and the like), organometallic reagents (e.g., Grignard reagents; organolithium reagents such as n-butyl lithium, t-butyl lithium, sec-butyl lithium; trialkyl aluminums such as triethyl aluminum, tributyl aluminum, triisobutyl aluminum, triisopropyl aluminum, trioctyl aluminum, and the like, metal amides (e.g., lithium diisopropyl amide, metal bis(trimethylsily)amides such as KHMDS, and the like), palladium on carbon. (Pd/C) catalysts, and combinations thereof.

In some embodiments, the conditioning, agent is a metal alkyl compound. In some embodiments, the metal, M, can be lithium, sodium, potassium, magnesium, calcium, zinc, cadmium, aluminum, or gallium. Examples of suitable alkyl radicals, R, include, but are not limited to, methyl, ethyl, butyl, hexyl, decyl, tetradecyl, and eicosyl (i.e., icosyl). Examples of metal alkyl compounds include, but are not limited to, $Mg(CH_3)_2$, $Mg(C_2H_5)_2$, $Mg(C_2H_5)(C_4H_9)$, $Mg(C_4H_9)_2$, $Mg(C_6H_{13})_2$, $Mg(C_{12}H_{25})_2$, $Zn(CH_3)_2$, $Zn(C_2H_5)_2$, $Zn(C_4H_9)_2$, $Zn(C_4H_9)(C_8H_{17})_2$, $Zn(C_6H_{13})_2$, $Zn(C_6H_{13})_2$, $Al(C_2H_5)_3$, $Al(CH_3)_3$, $Al(n\text{-}C_4H_9)_3$, $Al(C_8H_{17})_3$, $Al(iso\text{-}C_4H_9)_3$, $Al(C_{12}H_{25})_3$, and combinations thereof. Metal alkyl compounds also include substances having one or more halogen or hydride groups, such as ethylaluminum dichloride, diethylaluminum chloride, diethylaluminum hydride, Grignard reagents, diisobutylaluminum hydride, and the like.

In some embodiments, the treating of the metathesis reaction material (e.g., a natural oil or a natural oil derivative) can include contacting the reaction material with a metal alkyl compound and, either simultaneously or separately, contacting the reaction material with a hydride-containing compound. In some embodiments, where the reaction material is contacted simultaneously with the metal alkyl compound and the hydride-containing compound, the hydride-containing compounds can be included in the metal alkyl compound. For example, in some instances, processes used to make certain metal alkyl compounds, such as trialkyl aluminum compounds, can lead to the formation of a certain concentration of hydride-containing compounds. In other embodiments, however, the metal alkyl compounds can be combined with one or more hydride-containing compounds. Or, in some embodiments, the metathesis reaction material can be treated by the hydride-containing compounds in a separate treatment step, which can be performed before, after, or both before and after, treatment of the reaction material with the metal alkyl compounds.

Any suitable hydride-containing compounds can be used. In some embodiments, the hydride-containing compounds are selected from the group consisting of metal aluminum hydrides (e.g., alkali metal aluminum hydrides such as $LiAlH_4$, $NaAlH_4$, and the like), alkyl aluminum hydrides (e.g., DIBALH), and combinations thereof. In some embodiments, the hydride-containing compound is an alkyl aluminum hydride, such as DIBALH.

In some embodiments, contacting the metathesis reaction material with the hydride-containing compound occurs in the same step as contacting the reaction material with the metal alkyl compound. In some embodiments, the weight-to-weight ratio of the metal alkyl compound to the hydride-containing compound in the treatment composition is from 2:1, or from 5:1, or from 10:1, or from 15:1, or from 20:1 to 1000:1. In some embodiments, the weight-to-weight ratio of the metal alkyl compound to the hydride-containing compound in the treatment composition is at least 2:1, or at least 5:1, or a least 10:1, or at least 15:1, or at least 20:1.

In certain instances, the efficacy of the Z-selective metathesis catalyst can be improved (e.g., the turnover number can be increased or the overall catalyst loading may be decreased) through slow addition of the catalyst to a substrate. The overall catalyst loading can be decreased by at least 10%, at least 20%, or at least 30% when administered slowly to achieve the same turnover number as a single, full batch loading. The slow addition of overall catalyst loading can include adding fractional catalyst loadings to the reaction materials at an average rate of approximately 10 ppm by weight of catalyst per hour (ppmwt/hr), 5 ppmwt/hr, 1 pmwt/hr, 0.5 ppmwt/hr, 0.1 ppmwt/hr, 0.05 ppmwt/hr or 0.01 ppmwt/hr. In some embodiments, the catalyst is slowly added at a rate of between about 0.01-10 ppmwt/hr, 0.05-5 ppmwt/hr, or 0.1-1 ppmwt/hr. The slow addition of the catalyst can be conducted in batch loadings at frequencies of every 5 minutes, 15 minutes, 30 minutes, 1 hour, 2 hours, 4 hours, 12 hours, or 1 day. In other embodiments, the slow addition is conducted in a continuous addition process.

In some embodiments, an internal olefin (Z5-decene,) and a metathesis reaction partner (e.g., oleyl acetate) are combined in a ratio ranging from 2:1 to 10:1 (e.g., 5:1) and treated with an aluminum reagent (e.g., 1 wt % magnesium aluminum isopropoxide) prior to addition of metathesis catalyst (e.g., ruthenium Cat. 3 as described below) with a loading of 1-100 ppm per double bond (e.g., 3-50).

Preparation of Internal Olefins

In some embodiments, the synthesis of the fatty olefin metathesis product comprises forming the internal olefin by contacting a terminal olefin with a metathesis catalyst to form the internal olefin. In some embodiments, the internal olefin is a compound of Formula VIa:

(VIa)

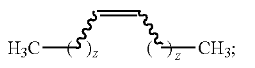

and the terminal olefin is a compound of formula IVb:

(IVb)

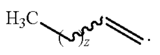

In some embodiments, the internal olefin is prepared using a Z-selective ruthenium catalyst or a Z-selective tungsten catalyst. In some embodiments, the internal olefin is prepared using a metathesis catalyst having a structure according to Formula XI:

(XI)

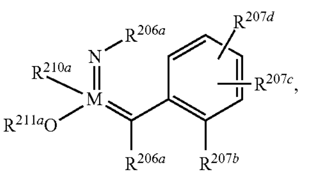

wherein:

M as tungsten $R^{206a}$ is aryl, heteroaryl, alkyl, or cyeloalkyl, each of which is optionally substituted;

$R^{210a}$ is pyrrolyl, imidazolyl, indolyl, pyrazolyi, azaindolyl, or indazolyl, each of which is optionally substituted;

$R^{211a}$ is optionally substituted aryl;

$R^{208a}$ is a hydrogen atom, alkyl, or alkoxy;

$R^{207b}$ is a hydrogen atom, —O—($C_{1-6}$ alkyl), —$CH_2$—O—($C_{1-6}$ alkyl), heteroalkoxy, or —N($C_{1-6}$ alkyl)$_2$; and $R^{207c}$ and $R^{207d}$ are independently a hydrogen atom, $C_{1-6}$ alkyl, $C_{1-6}$ alkoxy, a halogen atom, —$NO_2$, an amide, or a sulfonamide.

In some embodiments, $R^{210a}$ pyrrolyl, imidazolyl, pyrazolyl, azaindolyl, or indazolyl, each of which is optionally substituted; and is a hydrogen atom. $R^{206a}$ is phenyl, 2,6-dichlorophenyl, 2,6-dimethylphenyl, 2,6-diisopropylphenyl, 2-trifluoromethyphenyl, pentafluorophenyl, tert-butyl, or 1-adamantyl. In some embodiments, $R^{207b}$ is methoxy, $R^{207c}$ is hydrogen, and $R^{207d}$ is hydrogen. In some embodiments, $R^{206a}$ is:

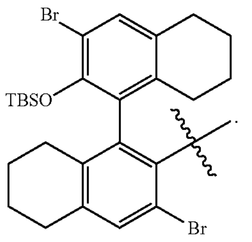 [SMILES: *c1c(Br)cc2c(c1-c1c3c(cc(Br)c1O[Si](C)(C)C(C)(C)C)CCCC3)CCCC2]

In some embodiments, the internal olefin is prepared using a metathesis catalyst having a structure according to Formula XII:

(XII)

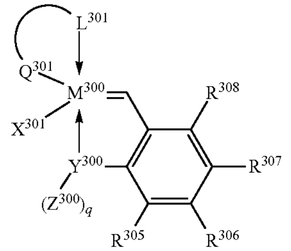

wherein:

$M^{300}$ is ruthenium;

$L^{3001}$ is a ligand having, the structure

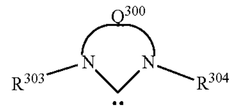

wherein:

$Q^{300}$ is selected from hydrocatbylene, substituted hydrocarbylene, heteroatom-containing hydrocarbylene, or substituted heteroatom-containing hydrocarbylene, wherein two or more substituents on adjacent atoms within Q may also be linked to form an additional cyclic structure, and $R^{303}$ and $R^{304}$ independently, selected from hydrocarbyl, substituted hydrocarbyl, heteroatom containing hydrocarbyl, or substituted heteroatom-containing hydrocarbyl;

$Q^{301}$ is a bond between and a carbon atom of $R^{303}$;

$R^{305}$, $R^{306}$, $R^{307}$, and $R^{308}$ are each independently selected from the group consisting of hydrogen, halogen, alkyl, alkenyl, alkynyl, aryl, heteroalkyl, heteroatom containing alkenyl, heteroalkenyl, heteroaryl, alkoxy, alkenyloxy, aryloxy, alkoxycarbonyl, carbonyl, alkylamino, alkylthio, aminosulfonyl, monoalkylaminosulfonyl, dialkylaminosulfonyl, alkylsulfonyl, nitrile, nitro, alkylsulfinyl, trihaloalkyl perfluoroalkyl, carboxylic acid, ketone, aldehyde, nitrate, cyano, isocyanate, hydroxyl, ester, ether, amine, imine, amide, halogen-substituted amide, trifluoroamide, sulfide, disulfide, sulfonate, carbamate, silane, siloxane, phosphine, phosphate, or borate, wherein any combination of $R^{305}$, $R^{306}$, $R^{307}$ and $R^{308}$ can be linked to form one or more cyclic groups;

$X^{301}$ is selected from the group consisting of halide, nitrate, alkyl, aryl, alkoxy, alkylcarboxylate, aryloxy, alkoxycarbonyl, aryloxycarbonyl, arylcarboxylate, acyl, acyloxy, alkylsulfonato, arylsulfonato, alkylsulfanyl, arylsulfanyl, alkylsulfinyl, and arylsulfinyl;

$Y^{300}$ is a heteroatom selected from the group consisting of N, O, S, and P; subscript q is 1 when $Y^{300}$ is O or S, and subscript q is 2 when $Y^{300}$ is N or P, and $Z^{300}$ is selected from hydrogen, alkyl, aryl, functionalized alkyl, or functionalized aryl wherein the functional group(s) are independently selected from the group consisting of alkoxy, aryloxy, halogen, carboxylic acid, ketone, aldehyde, nitrate, cyano, isocyanate, hydroxyl, ester, ether, amine, imine, amide, trifluoroamide, sulfide, disulfide, carbamate, silane, siloxane, phosphine, phosphate, or borate; methyl, isopropyl, sec-butyl, t-butyl, neopentyl, benzyl, phenyl and trimethylsilyl.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated, and unsaturated species, such as alkyl groups, alkenyl groups, aryl groups, and the like. "Hydrocarbylene" refers to a divalent hydrocarbyl moiety containing 1 to about 30 carbon atoms.

In some embodiments, $Q^{300}$ is a hydrocarbylene group (e.g., ethylene). In some embodiments, ligand $L^{301}$ is 1,3 di-substituted 4,5-dihydroimidazol-2-ylidene moiety. In some embodiments, $R^{303}$ is an adamantyl or substituted admantyl group, or a substituted $C_{3-12}$ cycloalkyl group. In some embodiments, $R^{304}$ is a di-substituted aryl group (e.g., a phenyl group in which both ortho ring positions are substituted, e.g., with isopropyl groups) or a tri-substituted aryl group (e.g., a phenyl group in which both ortho ring positions and the para ring position are substituted, e.g., with methyl groups).

In some embodiments, $R^{305}$, $R^{306}$, $R^{307}$ and $R^{308}$ are hydrogen. In some embodiments $Y^{300}$ is O. In some embodiments, $Z^{300}$ is alkyl (e.g., isopropyl). In some embodiments, $X^{301}$ is nitrate.

Metathesis reactions for preparation of internal olefins (e.g., Z5-decene) from terminal olefins (e.g., 1-hexene) can be carried out as described above for preparation of acylated alkenol metathesis products and alkenal acetal metathesis products. In some embodiments, a terminal olefin according to Formula IVb (e.g., 1-hexene) is combined with a ruthenium catalyst as shown below:

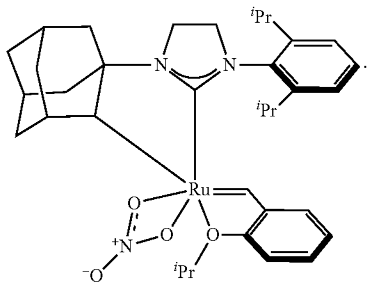

In some embodiments, the catalyst is present in an amount ranging from about 1 ppm to about 50 ppm (e.g., 3-50 ppm, or 5-10 ppm), based on the total number of double bonds in the reaction mixture. In some embodiments, the reactions are conducted for 1-8 hours, or longer, at temperatures ranging from about 20° C. to about 60° C. (e.g., 50° C.). The reactions can be conducted neat, in the absence of additional solvent.

Compositions and Uses Thereof

In some embodiments, the fatty olefin metathesis products prepared according to the methods described herein are pheromones. Accordingly, the pheromones prepared herein can be formulated for use as insect control compositions. The pheromone compositions can include a carrier, and/or be contained in a dispenser. The carrier can be, but is not limited to, an inert liquid or solid.

Examples of solid carriers include but are not limited to fillers such as kaolin, bentonite, dolomite, calcium carbonate, talc, powdered magnesia, Fuller's earth, wax, gypsum, diatomaceous earth, rubber, plastic, silica and China clay. Examples of liquid carriers include, but are not limited to, water; alcohols, such as ethanol, butanol or glycol, as well as their ethers or esters, such as methylglycol acetate; ketones, such as acetone, cyclohexanone, methylethyl ketone, methylisobutylketone, or isophorone; alkanes such as hexane, pentane, or heptanes; aromatic hydrocarbons, such as xylenes or alkyl naphthalenes; mineral or vegetable oils; aliphatic chlorinated hydrocarbons, such as trichloroethane or methylene chloride; aromatic chlorinated hydrocarbons, such as chlorobenzenes; water-soluble or strongly polar solvents such as dimethylformamide, dimethyl sulfoxide, or N-methylpyrrolidone; liquefied gases; and mixtures thereof. Baits or feeding stimulants can also be added to the carrier.

Pheromone compositions can be formulated so as to provide slow release into the atmosphere, and/or so as to be protected from degradation following release. For example, the pheromone compositions can be included in carriers such as microcapsules, biodegradable flakes and paraffin wax-based matrices.

Pheromone compositions can contain other pheromones or attractants provided that the other compounds do not substantially interfere with the activity of the composition. The pheromone compositions can also include insecticides. Examples of suitable insecticides include, but are not limited to, buprofezin, pyriproxyfen flonicamid, acetamiprid, dinotefuran, clothianidin, acephate, malathion, quinolphos, chloropyriphos, profenophos, bendiocarb, bifenthrin, chlorpyrifos cyfluthrin, diazinon, pyrethrum, fenpropathrin, kinoprene, insecticidal soap or oil, and mixtures thereof.

Pheromone compositions can be used in conjunction with a dispenser for release of the composition in a particular environment. Any suitable dispenser known in the an can be used. Examples of such dispensers include but are not limited to bubble caps comprising a reservoir with a permeable barrier through which pheromones are slowly released, pads, beads, tubes rods, spirals or balls composed of rubber, plastic, leather, cotton, cotton wool, wood or wood products that are impregnated with the pheromone composition. For example, polyvinyl chloride laminates, pellets, granules, ropes or spinals from which the pheromone composition evaporates, or rubber septa. One of skill in the art will be able to select suitable carriers and/or dispensers for the desired mode of application, storage, transport or handling.

A variety of pheromones, such as (Z)-tetradec-9-en-1-yl acetate, (Z)dodec-9-en-1-yl acetate, and (Z)-tetradec-11-en-1-yl acetate, can be prepared according to the methods of the invention and formulated as described above. For example, the methods of the invention can be used to prepare fall army worm (*Spodoptera frugiperda*) sex pheromone, which is (Z)-tetradec-9-en-1-yl acetate. The fall army worm sex pheromone can be used in conjunction with a sustained pheromone release device having a polymer container containing a mixture of the fall army worm sex pheromone and a fatty acid ester (such as a sebacate, laurate, palmitate, stearate or arachidate ester) or a fatty alcohol such as undecanol, dodecanol, tridecanol, tridecenol, tetradedanol, tetradecenol, tetradecadienol, pentadecanol, pentadecenol, hexadecenol, hexadecenol, hexadecadienol, octadecenol and octadecadienol). The polymer container can be a tube, an ampule, or a bag made of a polyolefin or an olefin component-containing copolymer. Sex pheromones of other pest insects such the cotton bollworm (*Helicoverpa armigera*), oriental fruit moth (*Grapholita molesta*) and leaf roller (*Tortricidae*) can be used in this type of sustained pheromone release device. The sex pheromones typically include one or more aliphatic acetate compounds having from 10 to 16 carbon atoms (e.g., decyl acetate, decenyl acetate, decadienyl acetate, undecyl acetate, undecenyl acetate, dodecyl acetate, dodecenyl acetate, dodecadienyl acetate, tridecyl acetate, tridecenyl acetate, tridecadienyl acetate, tetradecyl acetate, tetradecenyl acetate, tetradecadienyl acetate, and the like) and/or one or more aliphatic aldehyde compounds having from 10 to 16 carbon atoms (e.g., 7-hexadecenal, 11-hexadecenal, 13-octadecenal, and the like).

Pheromones prepared according to the methods of the invention as well as compositions containing the pheromones, can be used to control the behavior and/or growth of insects in various environments. The pheromones can be used, for example, to attract or repel male or female insects to or from a particular target area. The pheromones can be used to attract insects away from vulnerable crop areas. The pheromones can also be used example to attract insects as part of a strategy for insect monitoring, mass trapping, lure/attract-and-kill or mating disruption.

Mass trapping involves placing a high density of traps in a crop to be protected so that a high proportion of the insects are removed before the crop is damaged. Lure/attract-and-kill techniques are similar except once the insect is attracted to a lure, it is subjected to a killing agent. Where the killing agent is an insecticide, a dispenser can also contain a bait or feeding stimulant that will entice the insects to ingest an effective amount of the insecticide.

It will be appreciated by a person skilled in the art that a variety of different traps are possible. Suitable examples of such traps include water traps, sticky traps, and one-way traps. Sticky traps come in many varieties. One example of a sticky trap is of cardboard construction, triangular or wedge-shaped in cross-section, where the interior surfaces are coated with a non-drying sticky substance. The insects contact the sticky surface and are caught. Water traps include pans of water and detergent that are used to trap insects. The detergent destroys the surface tension of the water, causing insects that are attracted to the pan, to drown in the water. One-way traps allow an insect to enter the trap hut prevent it from exiting. The traps of the invention can be colored brightly, to provide additional attraction for the insects.

The trap is positioned in an area infested (or potentially infested) with insects. Generally, the trap is placed on or close to a tree or large plant and the pheromone attracts the insects to the trap. The insects can then be caught, immobilized and/or killed within the trap, for example, by the killing agent present in the trap.

Pheromones prepared according to the methods of the invention can also be used to disrupt mating. Strategies of mating disruption include confusion, trail-masking and false-trail following. Constant exposure a insects to a high concentration of a pheromone can prevent male insects from responding to normal levels of the pheromone released by female insects. Trail-masking uses a pheromone to destroy the trail of pheromones released by females. False-trail following is carried out by laying numerous spots of a pheromone in high concentration to present the male with many false trails to follow. When released in sufficiently high quantities, the male insects are unable to find the natural source of the sex pheromones (the female insects) so that mating cannot occur.

Insect populations can be surveyed or monitored by counting the number of insects in a target area (e.g., the number of insects caught in a trap). Inspection by a horticulturist can provide information about the life stage of a population. Knowing where insects are, how many of them there are, and their life stage enables informed decisions to be made as to where and when insecticides or other treatments are warranted. For example, a discovery of a high insect population can necessitate the use of methods for removal of the insect. Early warning of an infestation in a new habitat can allow action to be taken before the population becomes unmanageable. Conversely, a discovery of a low insect population can lead to a decision that it is sufficient to continue monitoring the population. Insect populations can be monitored regularly so that the insects are only controlled when they reach a certain threshold. This provides cost-effective control of the insects and reduces the environmental impact of the use of insecticides.

As will be apparent to one of skill in the art, the amount of a pheromone or pheromone composition used for a particular application can vary depending on several factors such as the type and level of infestation; the type of composition used; the concentration of the active components; bow the composition is provided, for example, the type of dispenser used; the type of location to be treated; the length of time the method is to be used for; and environmental factors such as temperature, wind speed and direction, rainfall and humidity, Those of skill in the art will be able to determine an effective amount of a pheromone or pheromone composition for use in a given application.

IV. Examples

Example 1. Synthesis of Oleyl Alcohol

Commercial oleyl alcohol contains isomerization-derived impurities (i.e., elaidyl alcohol) due to the extreme conditions required by the heterogenous catalyst (i.e., copper chromite) used in those processes. High purity oleyl alcohol may optionally be prepared using a homogenous catalyst, such as [Ru-SNS] or [Ru-PNP], and milder conditions (see, FIG. 1).

In a typical preparation, methyl oleate is combined with a base (i.e., sodium ethoxide), optionally a solvent (i.e., tetrahydrofuran), and a catalytic amount of an ester hydrogenation catalyst (i.e., [Ru-SNS] or [Ru-PNP]) in a reactor. The reactor is then heated to 30-60° C. and pressurized with hydrogen gas to 5-30 bar. When the reaction is complete, the reactor is depressurized and the contents washed with water or aqueous solutions (i.e., aqueous hydrochloric acid) to remove reaction by-products. The product may be further purified by methods such as distillation, if required. Olevl alcohol produced using Ru-SNS and Ru-PNP provides >98% Z-selectivity with <1.0% over-reduction of the double bond.

Example 2. Synthesis of Oleyl Acetate

Condition A: A round bottom flask, equipped with a magnetic stat bar, was charged with oleyl alcohol (1 molar equivalent), dichloromethane and $NEt_3$ (3 molar equivalents). The flask was placed under an inert atmosphere and cooled with an external ice bath. Acetic anhydride (2 molar equivalents) was added dropwise to the flask followed by a catalytic amount of 4-dimethylaminopyridine. The reaction mixture was slowly warmed to room temperature overnight. After 16 hours, the reaction was quenched with water and the organic layer washed with a saturated aqueous solution of ammonium chloride. Following additional washes with saturated aqueous solutions of both sodium bicarbonate and sodium chloride, the resultant organic layer was dried using anhydrous magnesium sulfate. The magnesium sulfate was removed by filtration and all volatile components removed. In vacuo to yield as yellow to colorless oil in >95% yield.

Condition B: A round-bottom flask equipped with a magnetic stir bar was charged with oleyl alcohol (1 molar equivalent) and a catalytic amount of anhydrous sodium acetate, The flask was placed under an inert atmosphere and heated to 60° C. with stirrings. Acetic anhydride (1.2 molar equivalents) was added at a rate such that the reaction temperature did not exceed 60° C. After 16 hours the reaction mixture was cooled to ambient temperature and quenched with water. The organic layer was washed with water and then dried using anhydrous magnesium sulfate. The magnesium sulfate was removed by filtration to yield a yellow to colorless oil in >95% yield.

Depending on the commercial source of the oleyl alcohol, the Z:E ratio of the oleyl acetate resulting from these procedures was as low as 80:20 and generally not higher than 95:5.

Example 3. Synthesis of Z-Internal Olefins for Metathesis Reactions

General Procedure for the synthesis of Z-internal olefins. Z-internal olefins are synthesized via metathesis of terminal olefins with a cis-selective metal metathesis catalyst (e.g., a tungsten catalyst or a ruthenium catalyst). The ethylene produced during, the metathesis reaction is purged with an inert gas, e.g., nitrogen or argon. Alternatively, ethylene can be removed by applying the appropriate vacuum to remove ethylene while leaving the starting material in the reaction system.

To a reactor containing a reflux condenser and an optional inert gas in-let port, is added 1.0 mol of terminal olefin (water<100 ppm peroxide value (PV) <0.1 meq/Kg) and degassed with the inert gas for 15 minutes. When a tungsten catalyst is employed, a saturated ester such as mefhyl caprate (1000 to 5000 mol ppm to internal olefin) is added. Triethylaluminum (TEAl; 1000 to 3000 mol ppm to mol terminal olefin) is added and stirred for 1 h to 24 h (e.g., 4 h to 8 h). When a ruthenium catalyst is employed, filtering the starting material through a plug of activated alumina is an efficient pre-treatment to obtain water<100 ppm and PV<0.1 meq/Kg.

Cis-selective catalyst (3 to 50 mol ppm to mol terminal olefin) is added in one portion and stirring is initiated. The inert gas purge is initiated with a flow rate of 15 to 30 L/h/Kg. Alternatively, a vacuum can be used to assist in removing ethylene, with typical pressures in the range of 400 Torr to 30 Torr. The starting material is kept in the reactor by employing a reflux condenser. The metathesis reactions are run from 1 to 30 h, typically 4 to 8 h.

The tungsten catalyst is inactivated with 3000 to 5000 mol ppm to mol terminal olefin of an alcohol (e.g., methanol, ethanol, isopropanol, oleyl alcohol, or the like). The judicious choice of alcohol allows for recycling of starting materials and intermediates. The addition of the alcohol inactivates the metathesis catalyst and decomposes excess triethylaluminum. With ruthenium catalysts, tetraethylenepentamine (TEPA; 100 molar excess to catalyst) is added and heated to reflux for 1 hour. Typical reaction yields for both catalysts are between and 50% and 70% with >97% Z-selectivity.

Synthesis of Z5-decene. The synthesis of Z5-decene involves the self-metathesis of neat 1-hexene with Z-selective catalysts. The ethylene produced is removed from the reaction by vacuum. Efficient removal of the ethylene contributes to high is and high Z-selectivity. To a 250 mL round bottomed 3-necked flask, containing a reflux condenser, an inert gas in-let port and a magnetic stir bar, was added 40.8 g (0.49 mol) of 1-hexene (water concertation of <50 ppm and peroxide value (PV) of <0.1 meg/Kg). The material was degassed with nitrogen for 15 to 30 minutes, while warming to 50° C. Ruthenium Cat. 1 (2.6 mg. $3.92 \times 10^{-6}$ moles, 8 ppm/double bond) was added in one portion. The top of the reflux condenser was connected to a diaphragm pump and vacuum was applied. The vacuum was controlled from 160 Torr to 90 Torr.

Cat. 1

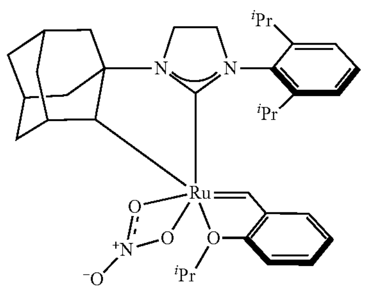

After 7 hours, GC analysis indicated 75.9% yield of Z5-decene with 99% Z-selectivity. TEPA (100 molar equivalents to catalyst) was added to quench the ruthenium catalyst. The reaction mixture was vacuum distilled, Bpt 114° C. at 170 Torr, to yield Z5-decene (24.2 g, 0.17 mol) in 71.4% isolated yield with 99% Z-selectivity. See, Table 1, Exp. 3-14.

manufacture of fine chemicals such as insect pheromones. Ruthenium Cat. 1 was found to consistently provide improved Z:E ratios as compared to other cis-selective catalysts as well as increased yields, e.g., 10% greater yields. These advantages allow for uniquely economical manufacturing processes.

Synthesis of Z5-decene. 1-Hexene was reacted with tungsten Cat. 2 from 20° C. to 40° C., to yield Z5-decene in 60% to 70% yields with Z-selectivity. See Table 2 and Table 3.

Cat. 2

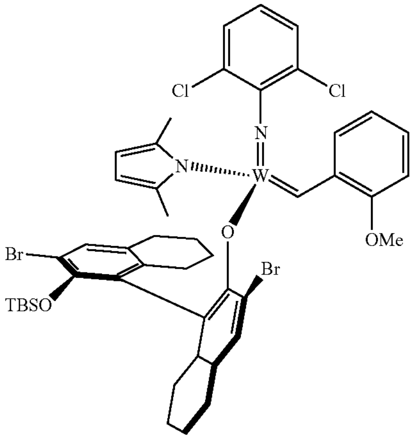

Synthesis of Z3-hexene. 1-Butene is reacted with Cat. 1 or Cat. 2, from −10° C. to 10° C., to yield Z3-hexene, the

TABLE 1

Synthesis of Z5-decene using ruthenium Cat. 1.

| Exp. No. | Cat. 1 loading (ppm/DB) | 1-Hexene (g) | Temp (° C.) | Vacuum (torr) | Time (h) | 1-Hexene[a] | Z5-Decene[a] | Internal Standard[a] | Unknown Impurity[a] | % Z[a] | % yield[b] |
|---|---|---|---|---|---|---|---|---|---|---|---|
| 3-1 | 77.5 | 10.0 | rt | — | 3.5 | 41.0 | 58.1 | 0.9 | 0.0 | — | 47.5 |
| 3-2 | 115 | 10.2 | rt | — | 3.5 | 58.8 | 40.1 | 1.1 | 0.0 | 100.0 | 35.7 |
| | | | | | 20 | 40.3 | 58.0 | 1.1 | 0.7 | 100.0 | 51.6 |
| 3-3 | 50 | 10.1 | 45 | — | 3.5 | 33.5 | 64.7 | 1.1 | 0.8 | 100.0 | 48.5 |
| | | | | | 6 | 34.5 | 64.1 | 1. | 0.4 | 99.0 | 51.0 |
| 3-4 | 75 | 10.2 | 35-37 | — | 3.5 | 48.3 | 50.9 | 0.8 | 0.0 | 100.0 | 42.0 |
| | | | | | 20 | 42.9 | 56.2 | 0.9 | 0.0 | — | 46.4 |
| 3-5 | 85 | 10.3 | 35-36 | — | 3.5 | 44.1 | 53.5 | 1.1 | 1.2 | 100.0 | 46.9 |
| 3-6 | 80 | 10.0 | 34-42 | — | 3.5 | 22.0 | 76.5 | 0.8 | 0.7 | 100.0 | 51.0 |
| 3-7 | 100 | 10.1 | 35-37 | — | 3.5 | 16.5 | 82.5 | 0.6 | 0.4 | 100.0 | 60.7 |
| 3-8 | 100 | 10.1 | 37-42 | — | 1.5 | 18.2 | 79.9 | 1.1 | 0.8 | 100.0 | 61.2 |
| | | | | | 3.5 | 20.3 | 78.3 | 1.0 | 0.4 | 99.2 | 59.9 |
| 3-9 | 50 | 40.9 | 45 | 120-185 | 3.5 | 14.4 | 84.8 | 0.6 | 0.3 | 98.8 | 77.2 |
| 3-10 | 27 | 40.2 | 45 | 130-180 | 3.5 | 24.1 | 75.4 | 0.0 | 0.4 | 98.8 | 67.7 |
| 3-11 | 13 | 40.4 | 45 | 130-160 | 3.5 | 40.3 | 58.9 | 0.3 | 0.4 | 98.9 | 56.9 |
| | | | | | 5.5 | 29.2 | 70.3 | 0.4 | 0.1 | 98.9 | 62.3 |
| 3-12 | 13 | 40.4 | 50 | 130-160 | 3.5 | 28.0 | 71.6 | 0.2 | 0.2 | 99.3 | 65.1 |
| | | | | | 5.5 | 10.3 | 89.6 | 0.0 | 0.2 | 98.9 | 81.4 |
| 3-13 | 13 | 40.4 | 55 | 120-165 | 3.5 | 23.1 | 76.2 | 0.3 | 0.3 | 99.4 | 70.6 |
| | | | | | 5.5 | 18.8 | 80.7 | 0.5 | 0.1 | 98.7 | 72.3 |
| 3-14 | 8 | 40.8 | 50 | 90-160 | 3.5 | 58.0 | 41.8 | 0.0 | 0.2 | 98.9 | 41.9 |
| | | | | | 5.5 | 40.5 | 59.3 | 0.0 | 0.2 | 99.2 | 57.5 |
| | | | | | 7 | 23.9 | 75.9 | 0.0 | 0.2 | 99.0 | 71.4 |
| 3-15 | 4 | 40.6 | 50 | 100-250 | 3.5 | 77.7 | 22.1 | 0.0 | 0.2 | 100.0 | 24.1 |
| | | | | | 5.5 | 69.6 | 30.3 | 0.0 | 0.1 | 99.1 | 32.2 |

[a] GC area (%).

[b] [((Z + E)5-Decene Area % x EOR mass)/theoretical 5-decene mass] x 100

In additional experiments summarized in Table 1, 1-hexene was reacted with ruthenium Cat. 1 from 20° C. to 60° C., to yield Z5-decene in 60% to 80% yields with 99% Z-selectivity. Ruthenium Cat. 1 is tolerant of air and moisture and is particularly advantageous for ease of handling during reaction is worked up when Z-selectivity drops to 97% or after 24 h. Yields in excess of 35% are obtained.

Synthesis of Z4-octene. 1-pentene reacted with. Cat. 1 or Cat. 2, from 15° C. to 30° C., to yield Z4-octene, the reaction is worked up when Z-selectivity drops to 97% or after 24 h. Yields in excess of 50% are obtained.

Synthesis of Z3-hexene and Z5-decene. As a technique to increase the efficiency of 1-butene, to 1-hexene saturated with 1-butene, is reacted with Cat. 1 or Cat. 2, from 10° C. to 40° C., to yield Z5-decene, Z3-octene and Z3-hexene, the reaction is worked up when Z-selectivity drops to 97% or after 24 h. Yields in excess of 60% are obtained for the sum of Z5-decene, Z3-octene and Z3-hexene, based on 1-hexene and 1-butene used.

<1 Torr vacuum, to yield HDDAc2, the reaction is worked up when Z-selectivity drops to 97% or after 24 h. HDDAc2 is purified by wiped film evaporation.

Self-metathesis of 7-Octenyl Acetate to Z7-tetradecen-dinyl 1,14-diacetate (TDDAc2). 7-octenyl acetate is reacted with Cat. 1 or Cat. 2, from 20° C. to 40° C. and under <1 Torr vacuum, to yield Z7-tetradecen-dinyl 1,14-diacetate TDDAc2, the reaction is worked up when Z-selectivity drops to 97% or after 24 h, TDDAc2 is purified by wiped film evaporation.

TABLE 2

Synthesis of Z5-decene using tungsten Cat. 2.
1-Hexene Metathesis Performed with Nitrogen Sparge

| Exp Ref. | 1-Hexene (g) | Temp (° C.) | Time (h) | Sparge Rate (L/h/kg) | Cat. 2 (ppm[mol]) | TEAI (ppm[mol]) | Methyl Caprate (ppm[mol]) | Oleyl Alcohol (ppm[mol]) | Final EOR Mass (g) | Dec-5-ene Yield (%) | (Z) Selectivity (%) |
|---|---|---|---|---|---|---|---|---|---|---|---|
| 3-16 | 249.5 | 20-24 | 3.0 | 15.5 | 12 | 1009 | 1496 | 1533 | 201.8 | 47% | 93% |
| 3-17 | 247.4 | 20-25 | 7.0 | 15.5 | 18 | 1039 | 1525 | 1470 | 189.5 | 49% | 93% |
| 3-18 | 252.5 | 17-23 | 7.0 | 15.5 | 20 | 995 | 1463 | 1403 | 172.7 | 73% | 88% |
| 3-19 | 252.4 | 17-20 | 3.0 | 28.7 | 19 | 994 | 1482 | 1627 | 191.4 | 65% | 96% |
| 3-20 | 251.8 | 17-21 | 7.0 | 28.7 | 9 | 1001 | 1460 | 1506 | 166.3 | 68% | 95% |
| 3-21 | 494.2 | 19-23 | 7.0 | 28.7 | 5 | 1013 | 1498 | 1510 | 328.5 | 56% | 97% |

*Dec-5-ene yield calculated by multiplying GC-FID area % (E + Z) with end of reaction (EOR) mass and dividing by theoretical dec-5-ene mass

TABLE 3

Synthesis of Z5-decene using tungsten Cat. 2.
1-Hexene Metathesis Performed Under Reduced Pressure

| Exp Ref. | 1-Hexene (g) | Temp (° C.) | Time (h) | Pressure (Torr) | Cat. 2 (ppm[mol]) | TEAI (ppm[mol]) | Methyl Caprate (ppm[mol]) | Oleyl Alcohol (ppm[mol]) | Final EOR Mass (g) | Dec-5-ene Yield (%)* | (Z) Selectivity (%) |
|---|---|---|---|---|---|---|---|---|---|---|---|
| 3-22 | 245.7 | 23-27 | 3.5 | 85-185 | 4 | 1021 | 1517 | 1544 | 205.67 | 64% | 97% |
| 3-23 | 226.8 | 23-27 | 3.5 | 108-170 | 4 | 1113 | 1631 | 1493 | 198.3 | 64% | 98% |
| 3-24 | 223.7 | 28-36 | 2.0 | 230-280 | 4 | 1112 | 1649 | 1527 | 195.2 | 63% | 97% |
| 3-25 | 209.1 | 13-18 | 3.5 | 39-102 | 4 | 1146 | 1602 | 1514 | 193.6 | 33% | 98% |
| 3-26 | 392.5 | 32-39 | 3.0 | 265-364 | 3 | 1024 | 1504 | 950 | 357.9 | 33% | 97% |
| 3-27 | 293.1 | 31-36 | 2.5 | 272-315 | 4 | 430 | 629 | 1294 | 252.47 | 64% | 97% |
| 3-28 | 301.5 | 34-39 | 3.3 | 281-322 | 4 | 525 | 752 | 1456 | 263.2 | 62% | 97% |
| 3-29 | 253.0 | 20-36 | 3.5 | 130-246 | 8 | 585 | 887 | 1487 | 214.4 | 63% | 96% |
| 3-30 | 1495.7 | 20-37 | 6.8 | 255-313 | 4 | 539 | 807 | 1516 | 1304.0 | 71% | 97% |

*Dec-5-ene yield calculated by multiplying GC-FID area % (E + Z) with end of reaction (EOR) mass and dividing by theoretical dec-5-ene mass Synthesis of Z7-tetradecene. 1-Octene is reacted with Cat. 1 or Cat. 2, from 15° C. to 30° C., to yield Z7-tetradecene, the reaction is worked up when Z-selectivity drops to 97% or after 24 h. Yields in excess of 50% are obtained.

Synthesis of Z9-octadecene. 1-Decene is reacted with Cat. 1 or Cat. 2, from 15° C. to 30° C., to yield Z9-octadecene, the reaction is worked up when Z-seleetivity drops to 97% or after 24 h. Yields in excess of 60% are obtained.

Self-metathesis of methyl 9-decenoate (9DAME) to Z9-octadecen-dioate 1,18-dimethyl ester (ODDA). 9-DAME is reacted with Cat. 1 or Cat. 2, from 20° C. to 40° C. and under <1 Torr vacuum, to yield ODDA, the reaction is worked up when Z-selectivity drops to 97% or after 24 h. ODDA is purified by wiped film evaporation.

Self-metathesis of 9-decenyl acetate to Z9-octadecen-dinyl 1,18-diacetate (ODDAc2). 9-Decenyl acetate is reacted with Cat. 1 or Cat. 2, from 20° C. to 40° C. and under <1 Torr vacuum, to yield ODDAc2, the reaction is worked up when Z-selectivity drops to 97% or after 24 h. ODDAc2 is purified by wiped film evaporation.

Self-metathesis of 8-Noneyl Acetate to Z8-hexadecen-dinyl 1,16-diacetate (HDDAc2). 8-nonenyl acetate is reacted with Cat. 1 or Cat. 2, from 20° C. to 40° C. and under Self-metathesis of 9-decenal acetal to Z9-octadecen-1,18-dial 1,18-diacetal (ODDA(acetal)2). 9-Decenal acetal (the acetal may be but not limited to dimethyl, diethyl, ethylene glycol, propylene glycol acetals) is reacted with Cat. 1 or Cat. 2, from 20° C. to 40° C. and under <1 Torr vacuum, to yield ODDA(acetal)2, the reaction is worked up when selectivity drops to 97% or after 24 h ODDA(acetal)2 is purified by wiped film evaporation.

Example 4. Cross-Metathesis of Oleyl Acetate with (Z)-dec-5-ene

Commercially available oleyl acetate (Z9-18Ac) is a low cost commodity feedstock for the production of Z9 pheromones such as Z9-12Ac and Z9-14Ac. However, due to the nature of the hydrogenation and distillation used in the manufacturing of oleyl acetate a significant amount (~20%) of cis/trans isomerization occurs leading to the formation of elaidyl alcohol (E9-18Ac). As such, metathesis products prepared from available materials were expected to contain a significant amount of E-olefin impurities. As described in detail below, however, it has now been found that a surprisingly high Z-content (>99%) in the product was obtained when metathesis reactions were conducted with catalysts such as Cat. 3, Cat. 4, and Cat. 5.

Figure 2:
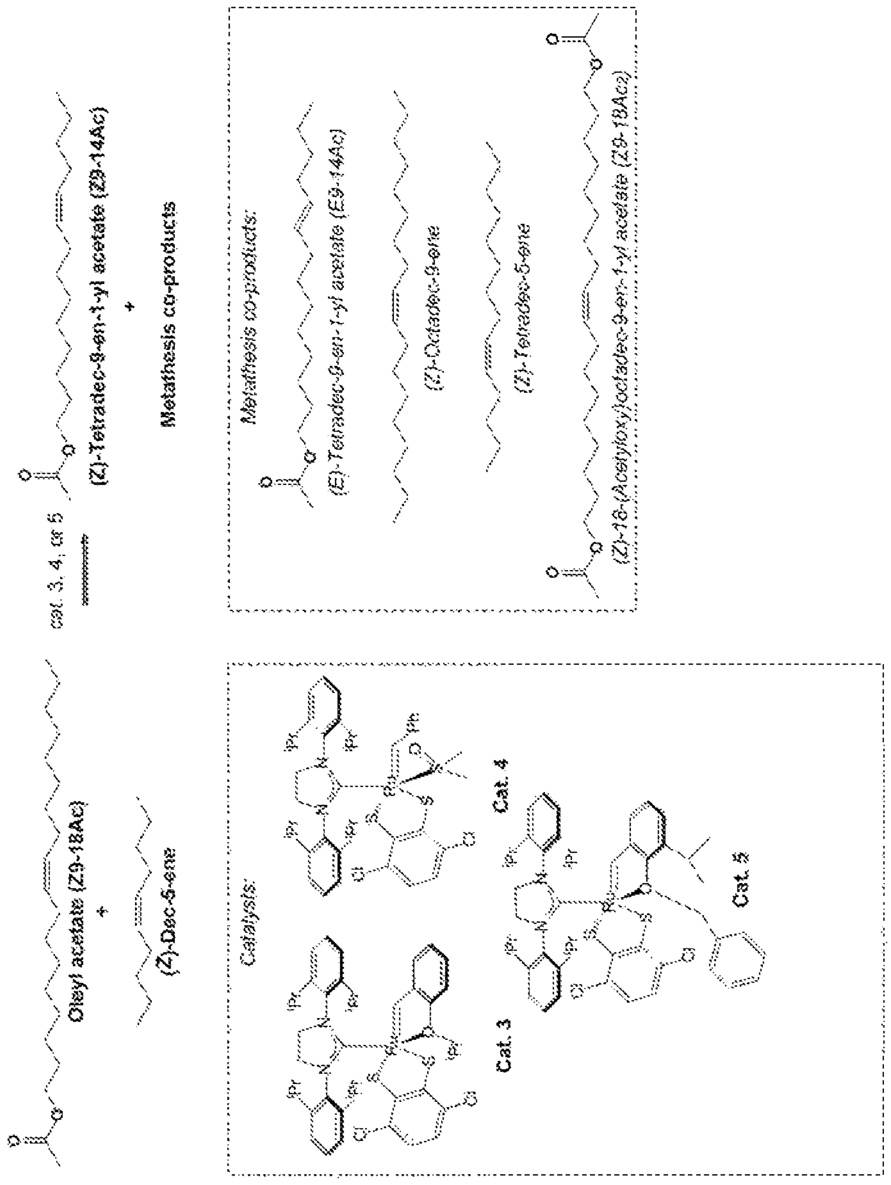
FIG. 2 shows the synthesis of Z9-14Ac via stereo-retentive olefin cross-metathesis using oleyl acetate with (Z)-dec-5-ene.

As in FIG. 2, the cross-metathesis of oleyl acetate (Z9-18Ac or "OA") with (Z)-dec-5-ene in the presence of Cat. 3, 4, or 5 leads to the formation of (Z)-tetradec-9-en-1-yl acetate (Z9-14Ac) and metathesis co-products.

General procedure for cross-metathesis screening reactions. In an inert atmosphere, a vial was charged with olefin feedstocks (i.e., OA and (Z)-dec-5-ene) and a magnetic stir bar. A stock solution of metathesis catalyst (e.g., Cat. 3, Cat. 4, or Cat. 5) was prepared in dichloromethane. The required amount of catalyst solution was added to the vial containing, the oleyl acetate and (Z)-dec-5-ene, and the resultant mixture stirred at ambient temperature (approximately 30° C.). The reactions were typically stirred for two hours before adding excess tris(hydroxymethyl)phosphine, relative to the amount of added metathesis catalyst. Next, water and dichloromethane were added to the quenched sample. The organic layer was then separated, dried over magnesium sulfate, and analyzed by gas chromatography (GC). GC analyses were conducted using either a HP-5 or a HP-88 capillary columns. GC data was analyzed using the equations below:

$$OA\ \%\ \text{Conversion (area \%)} = 100 - \left(\frac{OA\ \text{area \%}}{OA\ \text{area \%} + Z9{-}14Ac\ \text{area \%} + Z9{-}18Ac_2\ \text{area \%}}\right) \times 100$$

$$Z9{-}14Ac\ GC\ \text{Yield (area \%)} = \left(\frac{Z9{-}14Ac\ \text{area \%}}{OA\ \text{area \%} + Z9{-}14Ac\ \text{area \%} + Z9{-}18Ac_2\ \text{area \%}}\right) \times 100$$

$$Z\text{-Selectivity of } Z9{-}14Ac\ \text{(area \%)} = \frac{Z9{-}14Ac\ \text{area \%}}{Z9{-}14Ac\ \text{area \%} + E9{-}14Ac\ \text{area \%}} \times 100$$

Pretreatment of oleyl acetate to maximize catalyst efficiency. Using the general procedure for cross-metathesis above, 0.5 mmol of oleyl acetate (either pretreated or not pretreated), 1.5 mmol of (Z)-dec-5-ene, and either 0.113 µmol or 0.038 µmol of Cat. 3 or Cat. 4 were combined. Pretreated oleyl acetate was either purified by storage over a bed of alumina or by reaction with homogenous magnesium aluminum isopropoxide ($MgAl_2(O\text{-}i\text{-}Pr)_8$). In the case of pretreatment using $MgAl_2(O\text{-}i\text{-}Pr)_8$, the reagent and oleyl acetate feedstock were mixed and stored at ambient temperature for approximately 20 hours before performing the screening reactions without removal of the pretreatment reagent. The reactions were analyzed using GC and the effects of oleyl acetate pretreatment on catalyst efficiency are presented in Table 4.

TABLE 4

| Pretreatment | Catalyst Loading [ppm (mol)] | Catalyst | OA Conversion (area %) | Z9-14Ac GC Yield (area %) |
|---|---|---|---|---|
| 2 wt % | 75 | 3 | 76 | 71 |
| $MgAl_2(O\text{-}i\text{-}Pr)_8$ | | 4 | 75 | 70 |
| | 25 | 3 | 73 | 68 |
| | | 4 | 72 | 68 |
| Alumina | 75 | 3 | 74 | 70 |
| | | 4 | 73 | 68 |
| | 25 | 3 | 68 | 63 |
| | | 4 | 43 | 40 |

TABLE 4-continued

| Pretreatment | Catalyst Loading [ppm (mol)] | Catalyst | OA Conversion (area %) | Z9-14Ac GC Yield (area %) |
|---|---|---|---|---|
| none | 75 | 3 | 75 | 70 |
| | | 4 | 72 | 67 |
| | 25 | 3 | 51 | 47 |
| | | 4 | 24 | 22 |

Triethyl aluminum (TEAl) can also be used for pretreatment, as described below.

Optimization of magnesium aluminum isopropoxide pretreatment conditions. Using the general procedure for cross-metathesis above, above, 0.5 mmol oleyl acetate (either pretreated with $MgAl_2(O\text{-}i\text{-}Pr)_8$ or not pretreated), 1.5 mmol of (Z)-dec-5-ene, and either 0.113 µmol or 0.038 µmol of Cat. 3 or Cat. 4 were combined. Pretreated oleyl acetate was purified by reaction with homogenous $MgAl_2(O\text{-}i\text{-}Pr)_8$, in which the $MgAl_2(O\text{-}i\text{-}Pr)_8$ and oleyl acetate feedstock were mixed and stored at ambient temperature for 1, 2, 4, 8, or 20 days approximately before performing the screening reactions without removal of the pretreatment reagent. The results of the GC analysis of these pretreatment optimization screening reactions are presented in Table 5.

TABLE 5

| $MgAl_2(O\text{-}i\text{-}Pr)_8$ Loading (wt %) | Length of Pre-treat-ment (days) | Cata-lyst Loading [ppm(mol)] | Cata-lyst | OA Conver-sion (area %) | Z9-14Ac GC Yield (area %) |
|---|---|---|---|---|---|
| 2 | 1 | 75 | 3 | 76 | 71 |
| | | | 4 | 75 | 70 |
| | | 25 | 3 | 67 | 63 |
| | | | 4 | 53 | 50 |
| 1 | 2 | 75 | 3 | 76 | 71 |
| | | | 4 | 75 | 70 |
| | | 25 | 3 | 69 | 64 |
| | | | 4 | 63 | 59 |
| 0.5 | 4 | 75 | 3 | 76 | 71 |
| | | | 4 | 74 | 70 |
| | | 25 | 3 | 68 | 64 |
| | | | 4 | 53 | 50 |
| 0.25 | 8 | 75 | 3 | 75 | 70 |
| | | | 4 | 75 | 71 |
| | | 25 | 3 | 62 | 58 |
| | | | 4 | 48 | 45 |
| 0.1 | 20 | 75 | 3 | 75 | 70 |
| | | | 4 | 73 | 69 |
| | | 25 | 3 | 49 | 46 |
| | | | 4 | 37 | 35 |
| 0 | n/a | 75 | 3 | 75 | 70 |
| | | | 4 | 72 | 68 |
| | | 25 | 3 | 47 | 44 |
| | | | 4 | 25 | 23 |

Kinetic study product E/Z isomerization in cross-metathesis of oleyl acetate and (Z)-dec-5-ene. Using the general procedure above, 0.5 mmol of oleyl acetate, 1.5 mmol of (Z)-dec-5-ene, and 0.113 µmol of Cat. 3 or Cat. 4 were combined. Aliquots were taken at 0.5, 2, 3, 4 or 5 hours after the start of the reaction and analyzed by GC to determine the effect of extended reaction time on the Z-content the product. The results of the GC analysis of these E/Z isomerization screening reactions are presented in Table 6.

TABLE 6

| Catalyst | Reaction Length (hours) | Z9-14Ac Z-Selectivity (area %) |
|---|---|---|
| 3 | 0.5 | 99.8 |
| | 1 | 99.8 |
| | 2 | 99.7 |
| | 3 | 99.7 |
| | 4 | 99.7 |
| | 5 | 99.6 |
| 4 | 0.5 | 99.9 |
| | 1 | 99.8 |
| | 2 | 99.6 |
| | 3 | 99.5 |
| | 4 | 99.4 |
| | 5 | 99.4 |

Preparative scale cross-metathesis of oleyl acetate of (Z)-dec-5-ene. Inside an argon-filled glovebox, a three liter round bottom flask with a stir bar was charged with (Z)-dec-5-ene (620.4 g, 4.42 mol) and oleyl acetate (458.5 g, 1.48 mol) both of which were previously treated with activated alumina. Ruthenium Cat. 3 (0.375 g, 0.442 mmol) was added to the flask and the reaction was stirred at ambient temperature. After five hours, the contents of the flask were transferred to a five liter jacketed flask. Tris(hydroxymethyl) phosphine (30 mL, of 1 M iso-propanol solution 68 equiv.) was added and the contents were stirred at 60° C. for 18 hours. The reaction mixture was then washed twice with 1 liter of water. The organic layer was separated, dried over anhydrous magnesium sulfate, and filtered through a medium porosity fritted funnel to give a pale-yellow liquid. The mixture was purified by fractional vacuum distillation at <0.1 Torr. A 183 g main fraction, found to be 85% pure Z9-14Ac (0.63 mol, 43% molar yield based on oleyl acetate) by GC analysis, was collected at a head temperature of 89-100° C.

Example 5. Cross-Metathesis of Oleyl Acetate with (Z)-hex-3-ene

Figure 3:
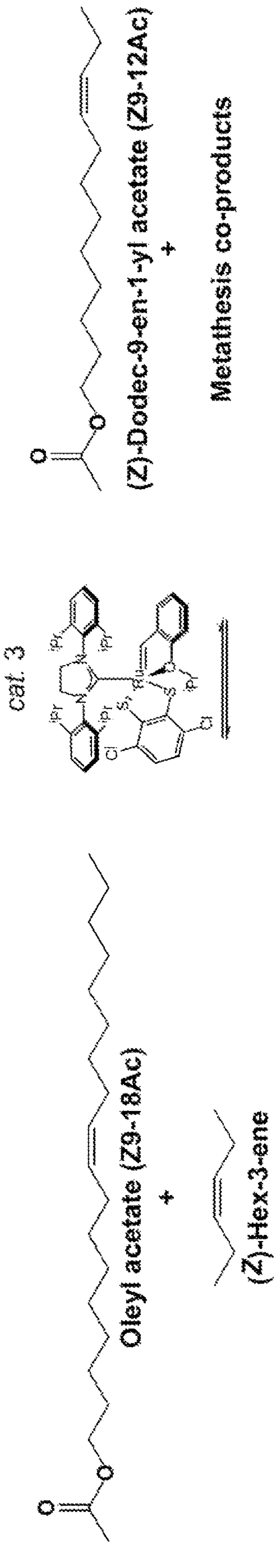
FIG. 3 shows the synthesis of Z9-12Ac via stereo-retentive olefin cross-metathesis using oleyl acetate with (Z)-hex-3-ene.

As shown in FIG. 3, the cross-metathesis of oleyl acetate (Z9-18Ac or "OA") with (Z)-hex-3-ene in the presence of Cat. 3 will lead to the formation of (Z)-dodec-9-en-1-yl acetate (Z9-12Ac) and metathesis co-products (not shown).

A flask with a stir bar is charged with (Z)-hex-3-ene (3 mol) and oleyl acetate (1 mol) both of which had previously treated purified. The required amount Cat. 3 required to reach equilibrium conversion is added to the flask and the reaction is stirred at ambient temperature. When the reaction is complete, the catalyst is deactivated by addition of tris (hydroxymethyl)phosphine and heating the contents with stirring. The reaction mixture is then washed water and the organic layer was separated. The organic layer is dried and then purified by fractional vacuum distillation to yield pure (Z)-dodec-9-en-1-yl acetate (Z9-12Ac).

Example 6. Study of Starting Material Composition in Cross-Metathesis of Oleyl Acetate with (Z)-dec-5-ene Synthesis of Z9-14Ac (Z9-tetradecenyl acetate) from ofeyl acetate and Z5-decene. Oleyl alcohol (Jarchem or BASF) was acetylated with acetic anhydride and catalytic amount of sodium acetate, worked up, and purified by wiped film evaporation. The Z:E ratio of the oleyl acetate was as low 80:20 and generally not higher than 95:5. To a 2 L round bottomed 3-necked flask, containing an inert gas in-let port and a magnetic stir bar, was added oleyl acetate (310 g, 1.0 mob and Z5-decene (700 g, 5.0 mol), both with water concentration of <100 ppm and PV<0.1 meq/Kg. The reaction mixture was degassed with nitrogen for 30 minutes. Magnesium aluminum isopropoxide (CAS #69207-83-6) (10 g, 1 wt %) was added and reaction was stirred, at 45° C., for 24 h. Ruthenium stereorententive metathesis Cat. 4 (304 mg, 0.4 mmol; 50 mol ppm to mol internal double bonds) was added in one portion, and stirring was initiated. The reaction was stirred at 45° C. for 5 hours. After 5 hours, TEPA (100 molar excess to catalyst) was added and heated to 120° C. for 1 hour. The reaction was cooled to 45° C., 250 mL of 1 M HCl was remove excess and TEPA-catalyst complex. Sodium bicarbonate (200 mL, saturated in water) was added, mixed and the aqueous phase was removed.

The crude reaction mixture was purified via vacuum distillation with a fraction distillation column containing a minimum of 8 theoretical plates. The Z5-decene and Z5-tetradecene were removed under 160 Torr vacuum. The product Z9-14Ac (203 g, 0.8 mol, Bpt 105° C. to 110° C. at 0.2 Torr) was provided by ruthenium Cat. 4 with good yield and excellent selectivity. The product was isolated in 95% purity with 99.4% Z-selectivity. The major impurity was Z9-octadecene (3%). The Z9-octadecene concentration can be minimized by adding more equivalents of Z5-decene in the metathesis reaction, and by employing refined distillation conditions. In addition, ruthenium Cat. 4 is a crystalline material which does not tend to generate static charge, making it particularly advantageous for handling during manufacturing.

The effect of the bond geometry in unfunctionalized olefins such as Z5-decene was also studied. Oleyl acetate was reacted with mixtures of 5-decene isomers having different E/Z ratios. The isomer mixtures were prepared by mixing Z5-decene (95% Z) and a thermodynamic mixture of 5-decene isomers (E/Z=81.5/18.5%) in different ratios. The results are shown below in Table 7. Remarkable, Z selectivity near 95% was observed even when the decene starting material was around 60% E5-decene.

TABLE 7

| Entry | Decene Z % | Cat. 4 loading (ppm) | TEAI (ppm) | Z9-14Ac, 4 hour reaction Yield (%)[a] | Z (%) |
|---|---|---|---|---|---|
| 5-1 | 90.4 | 50 | 5596 | 38.8 | 100 |
| 5-2 | 81.1 | 50 | 5583 | 36.6 | 99.0 |
| 5-3 | 71.6 | 51 | 5532 | 34.2 | 98.6 |
| 5-4 | 61.9 | 50 | 5433 | 32.3 | 98.0 |
| 5-5 | 41.4 | 51 | 5553 | 22.7 | 94.8 |

[a]Yield calculated by GC area %.

Example 7. Synthesis of Jojoba Oil Acetates

In a round bottom flask, commercial jojoba oil (3.5 kg) was reduced sing 1.2 molar equivalents of sodium bis(2-methoxyethoxy)aluminum hydride in toluene at approximately 0° C. The reaction mixture was quenched with aqueous sulfuric acid and then washed with water. The crude jojoba oil alcohols were then acetylated using an excess of acetic anhydride and a catalytic amount of anhydrous sodium acetate in toluene at 75-95° C. Following work-up, the final molar yield of jojoba oil acetates was >85%. GC analysis showed the composition of the final product was 5.2 area % (Z)-octadec-9-en-1-yl acetate, 55.6 area % (Z)-icos- 11-en-1-yl acetate, 30.4 area % (Z)-docos-13-en-1-yl acetate, 6.17 area % (Z)-tetracos-15-en-1-yl acetate, and 2.6 area % unidentified.

Example 8. Cross-Metathesis of Jojoba Oil Acetates with (Z)-hex-3-ene

As shown in FIG. 4, the cross-metathesis of the mixture of jojoba oil acetates ("JOAs") prepared from commercial jojoba oil with (Z)-hex-3-ene in the presence of Cat 3, Cat. 4, or Cat. 5 leads to the formation of (Z)-dodec-9-en-1-yl acetate (Z9-12Ac), (Z)-tetradec-11-en-1-yl acetate (Z11-14Ac), (Z)-hexadec-13-en-1-yl acetate (Z13-16Ac), (Z)-octadec-15-en-1-yl acetate (Z15-18Ac), and metathesis co-products.

General procedure for cross-metathesis screening reactions. In an inert atmosphere, a flask was charged with olefin feedstocks (i.e., jojoba oil acetates and two to four molar excess of (Z)-hex-3-ene) and a magnetic stir bar. A stock solution of Cat. 3 or Cat. 4 was prepared in dichloromethane. The required amount of catalyst solution was added to the flask containing the jojoba oil acetates (JOAs) and (Z)-hex-3-ene, and the resultant mixture stirred at ambient temperature (approximately 30° C.). The reactions were typically stirred for two hours before adding excess tris(hydroxymethyl)phosphine, relative to the amount of added metathesis catalyst. Next, water and dichloromethane were added to the quenched sample. The organic layer was then separated, dried over magnesium sulfate, and analyzed by gas chromatograpby (GC). GC analyses were conducted using either a HP-5 or a HP-88 capillary columns. GC data was analyzed using the equations below:

$$JOAs\ \%\ \text{Conversion (area \%)} = 100 - \left( \frac{\text{Jojoba Oil Acetates area \%}}{JOAs\ \text{area \%} + \text{Cross-metathesis}\ JOAs\ \text{area \%} + \text{Self-metathesis}\ JOAs\ \text{area \%}} \right) \times 100$$

$$Z\text{-Selectivity of}\ Z11\text{-}14Ac\ \text{(area \%)} = \left( \frac{Z11\text{-}14Ac\ \text{area \%}}{Z11\text{-}14Ac\ \text{area \%} + E11\text{-}14Ac\ \text{area \%}} \right) \times 100$$

Cross-metathesis of jojoda all acetates and varying amounts of (Z)-hex-3-ene, Using the general procedure for cross-metathesis above, 100 mmol of the prepared JOAs and either two or four molar equivalents of (Z)-hex-3-ene were combined with 75 ppm (mol) per double bond of Cat 3. were combined for one hour to examine the effect of substrate loading on reaction yield and selectivity. The reactions were analyzed using GC, and the results are shown in Table 8.

TABLE 8

| (Z)-hex-3-ene Molar Excess | Jojoba Oil Acetates Conversion (area %) | Z11-14Ac Content of Product Mixture (area %) | Z11-14Ac Z-Selectivity (area %) |
|---|---|---|---|
| 2 | 61.7 | 33.0 | 99.4 |
| 3 | 68.9 | 33.7 | 99.6 |

Cross-metathesis of jojoba oil acetates and (Z)-hex-3-ene with Cat. 3 or Cat. 4. Using the general procedure for cross-metathesis above, 100 mmol of the prepared JOAs and 300 mmol of (Z)-hex-3-ene were combined with either 2000, 300 or 150 ppm (mol) per double bond of Cat. 3 or Cat. 4 to examine the effect of the catalyst on reaction yield and selectivity. The reactions were analyzed using GC, and the results are shown in Table 9.

TABLE 9

| Catalyst | Catalyst Loading (ppm (mol) per double bond) | Jojoba Oil Acetates Conversion (area %) | Z11-14Ac Content of Product Mixture (area %) | Z11-14Ac Z-Selectivity (area %) |
|---|---|---|---|---|
| 3 | 2000 | 85.2 | 21.5 | 97.8 |
| | 300 | 83.5 | 21.4 | 99.0 |
| | 150 | 78.1 | 22.1 | 99.6 |
| 4 | 2000 | 84.7 | 22.8 | 99.3 |
| | 300 | 82.0 | 23.1 | 99.1 |
| | 150 | 70.1 | 19.5 | 99.5 |

Cross-metathesis of jojoba oil acetates and (Z)-hex-3-ene with varying amounts of catalysts. Using the general procedure for cross-metathesis above, 100 mmol of the prepared JOAs and 300 mmol of (Z)-hex-3-ene were combined with either 2000, 300 or 150 ppm (mol) per double bond of Cat. 3 to examine the effect of catalyst loading on reaction yield and selectivity. The reactions were analyzed using GC, and the results are shown in Table 10.

TABLE 10

| Catalyst Loading (ppm (mol) per double bond) | Reaction Length (hours) | Jojoba Oil Acetates Conversion (area %) | Z11-14Ac Content of Product Mixture (area %) | Z11-14Ac Z-Selectivity (area %) |
|---|---|---|---|---|
| 2000 | 1 | 85.2 | 40.6 | 97.8 |
| | 2.5 | 85.9 | 43.2 | 96.6 |
| 300 | 1 | 83.5 | 40.9 | 99.0 |
| 150 | 1 | 85.4 | 42.0 | 99.3 |

Example 9. Cross-metathesis of Jojoba Oil with (Z)-hex-3-ene

Figure 5:
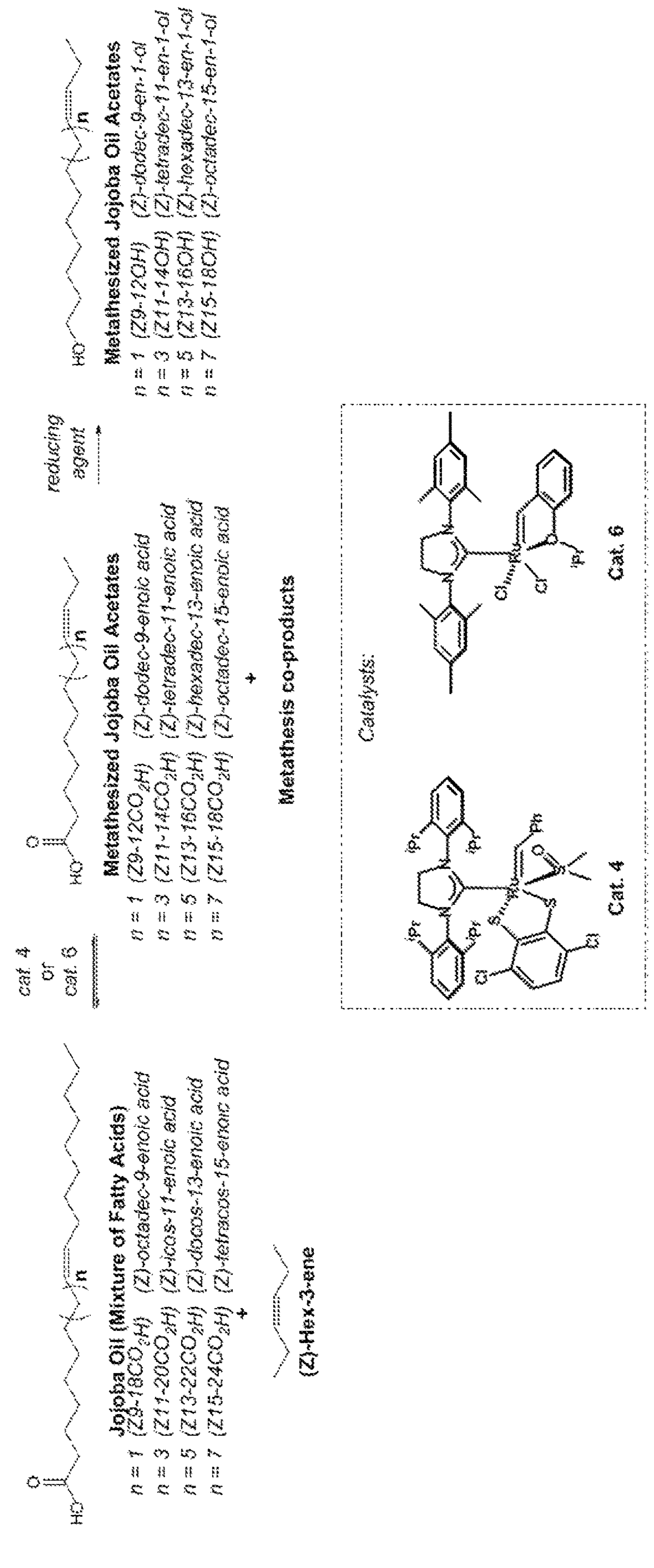
FIG. 5 shows the synthesis of cross-metathesized jojoba oil alcohols via stereo-retentive olefin cross-metathesis using commercial jojoba oil with (Z)-hex-3-ene, followed by reduction.

As shown below in FIG. 5, the cross-metathesis of commercial jojoba oil (i.e., fatty acid mixture) with (Z)-hex-3-ene in the presence of Cat. 4 or Cat. 6 leads to the formation of cross-metathesized jojoba oil fatty acids and metathesis co-products (not shown). The cross-metathesized jojoba oil fatty acids are then reduced to the corresponding cross-metathesized jojoba oil alcohols (Z)-dodec-9-en-1-ol (Z9-12OH), (Z)-tetradec-1-en-1-ol (Z11-14OH), (Z)-hexadec-13-en-1-ol (Z13-16OH), and (Z)-octadec-15-en-1-ol (Z15-18OH).

Cross-metathesis of jojoba oil acetates and (Z)-hex-3-ene with Cat. 4 or Cat. 6. Using the general procedure for cross-metathesis above, commercial jojoba oil ("JO") (50 mmol) and (Z)-hex-3-ene (300 mmol) underwent cross-metathesis using either metathesis Cat. 4 or Cat. 6. Reactions were performed at ambient temperature for two hours. Prior to GC analysis, the cross-metathesized JO samples (i.e., mixture ofeross-metathesized jojoba oil fatty acids) underwent reduction using sodium bis(2-methoxyethoxy)aluminum hydride according to the procedure described in Example 7, 'Synthesis of jojoba oil acetates.' The resulting cross-metathesized JO alcohols were then analyzed without further analysis to determine the content of (Z)-tetradec-11-en-1-ol (Z11-14OH) and the Z-selectivity of the Z11-14OH product. GC data was analyzed using the equations below, and the results are shown in Table 11.

Jojoba Oil Alcohols ("*JO Alc.*") % Conversion (area %) =

$$100 - \left( \frac{JO\ Alc.\ \text{area}\ \%}{JO\ Alc.\ \text{area}\ \% + \text{Cross-metathesis}\ JO\ Alc.\ \text{area}\ \% + \text{Self-metathesis}\ JO\ Alc.\ \text{area}\ \%} \right) \times 100$$

$Z$-Selectivity of $Z11$-$14OH$ (area %) =

$$\left( \frac{Z11\text{-}14OH\ \text{area}\ \%}{Z11\text{-}14OH\ \text{area}\ \% + E11\text{-}14OH\ \text{area}\ \%} \right) \times 100$$

TABLE 11

| Catalyst | Catalyst Loading (ppm (mol) per double bond) | Jojoba Oil Alcohol Conversion (area %) | Z11-14OH Content of Product Mixture (area %) | Z11-14OH Z-Selectivity (area %) |
|---|---|---|---|---|
| 6 | 300 | 72.4 | 6.5 | 16.3 |
| 4 | 300 | 39.6 | 15.8 | >99 |
| | 200 | 33.9 | 13.1 | >99 |

Example 10. Synthesis of Functionalized Olefin Products for use in Agricultural Applications General cross-metathesis reaction conditions with a ruthenium stereorententive metathesis catalyst. To a reactor with an inert gas in-let port is added 1.0 mol of functionalized internal olefin (e.g., oleyl acetate) and 3 to 6 molar equivalents of non-functionalized Z-intemai olefin (e.g., Z5-decene), both with water<100 ppm and PV<0.1 meq/Kg. The internal olefins are degassed with the inert gas for 15 minutes. Triethylaluminum (1000 to 3000 mol ppm to mol internal olefins) is added and stirred for 1 h to 24 h. Alternatively, filtering the starting materials through a plug of activated alumina is an efficient pre-treatment to obtain <100 ppm and PV<0.1 meq/Kg. A ruthenium stereorententive metathesis catalyst such as Cat. 3, Cat. 4, Cat 5, or the like (3 to 50 ppm per internal double bond) is added in one portion and stirring is initiated. The reactions are typically run between 20° C. and 60° C. TEPA (100 molar excess to catalyst) is added and heated to reflux for 1 hour to deactivate the catalyst. Typical reaction yields for both catalysts are between and 50% and 85% with >97% Z-selectivity. Purification and isolation is accomplished by packed bed fractional vacuum distillation.

Synthesis of Z9-14Ac from ODDAc2 and Z5-decene. ODDAc2 (1 mol) and Z5-decene (4 to 8 mol of Z5-decene per mol of ODDAc2) are stirred, degassed with nitrogen for 15 minutes and treated with triethylaluminum. Ruthenium stereorententive metathesis catalyst (e.g., Cat. 3, Cat. 4, or Cat. 5) is added and the reaction in monitored by GC analysis. Z9-14Ac is isolated by fractional vacuum packed bed distillation to yield Z9-14Ac with >97% Z-selectivity.

Synthesis of Z9-12Ac (Z7-dodecenyl acetate) from oleyl acetate and Z3-Hexene. Oleyl alcohol is converted to oleyl acetate and purified as described above. Oleyl acetate (1 mol) and Z3-hexene 3 to 6 mol of Z3-hexene per mol of oleyl acetate) are stirred, degassed with nitrogen for 15 minutes and treated with triethylaluminum. Ruthenium stereorententive metathesis catalyst (e.g., Cat. 3, Cat. 4, or Cat. 5) is added and the reaction in monitored by GC analysis, Z9-12Ac is isolated by fractional vacuum packed bed distillation, with >97% selectivity. Levels of impurities such as Z9-octadecene are kept to <3%.

Synthesis of Z9-12Ac from ODDAc2 and Z3-decene. ODDAc2 (1 mol) and Z3-hexene (4 to 8 mol of Z3-hexene per mol of ODDAc2) are stirred, degassed with nitrogen for 15 minutes and treated with triethylaluminum for 1 to 8 hours. Ruthenium stereorententive metathesis catalyst (e.g., Cat. 3, Cat. 4, or Cat. 5) is added and the reaction in monitored by GC analysis. Z9-12Ac is isolated by fractional vacuum packed bed distillation to yield Z9-12Ac with >97% Z-selectivity.

Synthesis of Z9-14Ac and Z9-12Ac from oleyl acetate and Z3-octene. Oleyl alcohol is converted to oleyl acetate and purified as described above. Oleyl acetate (1 mol) and Z3-octene (3 to 6 mol of Z3-octene per mol of oleyl acetate) are stirred, degassed with nitrogen for 15 minutes and treated with triethylaluminum. Ruthenium stereorententive metathesis catalyst (e.g., Cat. 3, Cat. 4, or Cat. 5) is added and the reaction in monitored by GC analysis, Z9-14Ac and Z9-12Ac are isolated by fractional vacuum-packed bed distillation. Both Z9-14Ac and Z9-12Ac are isolated in >95% purity and in >97% Z-selectivity. Levels of impurities such as Z9-octadecene are kept to <3%.

Synthesis of Z9-14Ac and Z9-12Ac from ODDAc2 and Z3-octene. ODDAc2 (1 mol) and Z3-octene (4 to 8 mol Z3-octene per mol of ODDAc2) are stirred, degassed with nitrogen for 15 minutes and treated with triethylaluminum. Ruthenium stereorententive metathesis catalyst (e.g. Cat. 3, Cat. 4, or Cat. 5) is added and the reaction in monitored by GC analysis, Z9-14Ac and Z9-12Ac are isolated by fractional vacuum-packed bed distillation. Both Z9-14Ac and Z9-12Ac are isolated in >95% purity with >97% Z-selectivity.

Synthesis of Z8-12Ac (Z8-dodeeenyl acetate) from HDDAc2 and Z4-octene. HDDAc2 (1 mol) and Z4-octene (3 to 6 mol of Z4-octene per mol of HDDAc2) are stirred, degassed with nitrogen for 15 minutes and treated with triethylaluminum. Ruthenium stereorententive metathesis catalyst (e.g., Cat. 3, Cat. 4, or Cat. 5) is added and the reaction in monitored by GC analysis. Z8-12Ac is isolated by fractional vacuum-packed bed distillation with >95% purity and with >97% Z-selectivity.

Synthesis of Z7-12Ac from TDDAc2 and Z5-decene, TDDAc2 (1 mol) and Z5-decene (3 to 6 mol of Z5-decene per mol of TDDAc2) are stirred, degassed with nitrogen for 15 minutes and treated with triethytaluminum. Ruthenium stereorententive metathesis catalyst (e.g., Cat. 3, Cat. 4, or Cat. 5) is added and the reaction in monitored by GC analysis, Z7-12Ac is isolated by fractional vacuum-packed bed distillation with >95% purity and with >97% Z-selectivity.

Synthesis of Z9-16Ac (Z9-hexadecenyl acetate) from oleyl acetate and Z7-tetradecene. Oleyl alcohol is converted to oleyl acetate and purified as described above. Oleyl acetate (1 mol) and Z7-tetradecene (4 to mol of Z7-tetradecene per mol of oleyl acetate) are stirred, degassed with nitrogen for 15 minutes and treated with triethylaluminum. Ruthenium stereorententive metathesis catalyst (e.g., Cat. 3, Cat. 4, or Cat. 5) is added and the reaction in monitored by GC analysis. Z9-16Ac is isolated by tractional vacuum-packed bed distillation in >95% purity and with >97% Z-selectivity. Levels of impurities such as Z9-octadecene are kept to <1%.

Synthesis of Z916Ac from ODDAc2 and Z7-tetradecene. ODDAc2 (1 mol) and Z7-tetradecene (4 to 8 mol of Z7-tetradecene per mol of ODDAc2) are stirred, degassed with nitrogen for 15 minutes and treated with triethylaluminurn. Ruthenium stereorententive metathesis catalyst (e.g., Cat. 3, Cat. 4, or Cat. 5) is added and the reaction in monitored by GC analysis, Z9-16Ac is isolated by fractional vacuum-packed bed distillation to isolate Z9-16Ac in >95% purity with >97% Z-selectivity.

Synthesis of Z9-16acetal is Z9-16acetal is Z9-hexadecenal acetal) from ODDA(acetal)2 and Z7-tetradecene. ODDA (acetal)2 (1 mol) and Z7-tetradecene (4 to 8 mol of Z7-tetradecene per mol of ODDA(acetal)2) are stirred, degassed with nitrogen for 15 minutes and treated with triethylaluminum. Ruthenium stereorententive metathesis catalyst (e.g., Cat. 3, Cat. 4, or Cat. 5) is added and the reaction in monitored by GC analysis, Z9-16acetal is isolated by fractional vacuum-packed bed distillation to isolate Z9-16acetal in >90% purity with >95% Z-selectivity.

Synthesis of Z9-18Ac (Z9-18Ac is Z9-octadecenyl acetate) from ODDAc2 and Z9-octadecene. ODDAc2 (1 mol) and Z9-octadecene (4 to 8 mol of Z9-octadecene per mol of ODDAc2) are stirred, degassed with nitrogen for 15 minutes and treated with triethylaluminum. Ruthenium stereorententive metathesis catalyst (e.g., Cat. 3, Cat. 4, or Cat. 5) is added and the reaction in monitored by GC analysis. Z9-18Ac is isolated by fractional vacuum-packed bed distillation to isolate Z9-18Ac in >95% purity with >97% Z-selectivity.

Synthesis of Z9-18acetal (Z9-18acetal is Z9-octadecenal acetal) from ODDA(acetal)2 and Z9-octadecene. ODDA (acetal)2 (1 mol) and Z9-octadecene (4 to 8 mol of Z9-octadecene per mol of ODDAc2) are stirred, degassed with nitrogen for 15 minutes and treated with triethylaluminum. Ruthenium stereorententive metathesis catalyst (e.g., Cat. 3, Cat. 4, or Cat. 5) is added and the reaction in monitored by GC analysis. Z9-18acetal is isolated by fractional vacuum-packed bed distillation to isolate Z9-18acetal in >90% purity and >95% Z-selectivity.

Synthesis of jojoba acetate by reduction and acetylation of jojoba oil to jojoba acetate. Jojoba oil (Greenchem) is diluted with an equal volume of anhydrous toluene, 1.5 molar equivalents of Vitride to 1 mol jojoba ester. After the reduction is complete, the reaction is carefully diluted with sulfuric acid until the aqueous phase is pH<1, and washed with brine. The organic phase is isolated and made anhydrous by azeotroping off water. The anhydrous jojoba alcohol is acetylated as described above for oleyl acetate. Jojoba acetate is purified by wiped-film evaporation in ~80% yields. The jojoba acetate composition is ~5% Z9-18Ac, ~55% Z11-22Ac, ~35% Z13-22Ac and ~5% Z15-24Ac.

Synthesis of Z9-12Ac, Z11-14Ac (Z11-tetradecenyl acetate) and Z13-16Ac (Z13-hexadecenyl acetate) from jojoba acetate and Z3-hexene. Jojoba acetates (1 mol) and Z3-hexene (4 to 8 mol of Z3-hexene per mol of jojoba acetate) are stirred, degassed with nitrogen for 15 minutes and treated with triethylaluminum. Ruthenium stereorententive metathesis catalyst (e.g., Cat. 3, Cat. 4, or Cat. 5) is added and the reaction in monitored by GC analysis. Z9-12Ac, Z11-14Ac and Z13-16Ac are isolated by fractional vacuum-packed bed distillation. Z9-12Ac, Z11-14Ac and Z13-16Ac are isolated in >95% purity and with >97% Z-selectivity.

Synthesis of Z9-14Ac, Z11-16Ac (Z11-hexadecenyl acetate) and Z13-18Ac (Z13-hexadecenyl acetate) from jojoba acetate and Z5-decene. Jojoba acetates (1 mol) and Z5-decene (4 to 8 mol of Z5-decene per mol of jojoba acetate) are stirred, degassed with nitrogen for 15 minutes and treated with triethylaluminum. Ruthenium stereorententive metathesis catalyst (e.g., Cat. 3, Cat. 4, or Cat. 5) is added and the reaction in monitored by GC analysis. Z9-14Ac, Z1116Ac and Z13-18Ac are isolated by fractional vacuum-packed bed distillation. Z9-14Ac, Z11-16Ac and Z13-18Ac are isolated in >95% purity and with >97% Z-selectivity.

Synthesis of jojoba acetal by reduction, oxidation and acetal formation of jojoba oil to jojoba acetals. Jojoba alcohol is prepared as described above. The anhydrous jojoba alcohol is oxidized to aldehyde (e.g., via Stahl oxidation, Swern oxidation, tetrapropylammonium perruthenate (TPAP) oxidation, or the like). Jojoba aldehyde is converted to an acetal (e.g., a dimethyl, diethyl, ethylene glycol, or propylene glycol acetal) using an excess of an alcohol and a catalytic amount of acid. The acetal is purified by wiped-film evaporation in ~70% isolated yield. The jojoba acetal composition is ~5% Z9-18acetal, ~55% Z11-20acetal, ~35% Z13-22acetal and ~5% Z15-24acetal.

Synthesis of Z9-14acetal (Z9-tetradecenal acetal), Z11-16acetal (Z11-hexadecenal acetal) and Z13-18acetal (Z13-octadecenal acetal) from jojoba acetal and Z5-decene. Jojoba acetal (1 mol) and Z5-decene (4 to 8 mol of Z5-decene per mol of jojoba acetal) are stirred, degassed with nitrogen for 15 minutes and treated with triethylaluminum. Ruthenium stereorententive metathesis catalyst (e.g., Cat. 3, Cat. 4, or Cat. 5) is added and the reaction in monitored by GC analysis, Z9-14acetal, Z11-16acetal and Z13-18acetal are isolated by fractional vacuum-packed bed distillation. Z9-14acetal, Z11-16acetal and Z13-18acetal are isolated in >80% purity and with >90% Z-selectivity.

V. Exemplary Embodiments

Exemplary embodiments provided in accordance with the presently disclosed subject matter include, but are not limited to, the claims and the following embodiments:

1. A method for synthesizing a Z-enriched fatty olefin metathesis product, the method comprising contacting an olefin metathesis reaction partner with an internal olefin in the presence of a group 8 transition metal metathesis catalyst to form the Z-enriched fatty olefin metathesis product, wherein:
   - the fatty olefin metathesis product is an acylated alkenol or an alkenal acetal,
   - the olefin metathesis reaction partner comprises a mixture of Z olefins and E olefins in a starting Z:E ratio,
   - the fatty olefin metathesis product comprises a mixture of Z olefins and E olefins in a product Z:E ratio, and
   - the product Z:E ratio is higher than the starting Z:E ratio.
2. The method of embodiment 1, wherein:
   - the fatty olefin metathesis product is an acylated alkenol of Formula I:

(I)

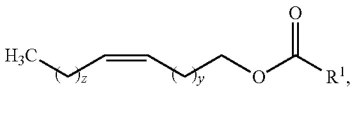

- the metathesis reaction partner is a compound of Formula III (III)

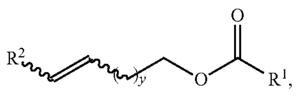

the internal olefin is a compound of Formula IV (IV)

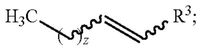

$R^1$ is selected from the group consisting of H and $C_{1-6}$ alkyl;

$R^2$ is selected from the group consisting of $C_{1-18}$ alkyl and $C_{2-18}$ alkenyl;

$R^3$ is $C_{1-18}$ alkyl;

subscript y is an integer ranging from 0 to 17;

subscript z is an integer ranging from 0 to 17; and the group 8 transition metal metathesis catalyst is a Z-selective group 8 transition metal catalyst.

3. The method of embodiment 1 or embodiment 2, wherein the metathesis catalyst is a Z-selective ruthenium catalyst or a Z-selective osmium catalyst.

4. The method of any one of embodiments 1-3, wherein the fatty olefin metathesis product is at least 97% Z.

5. The method of any one of embodiments 1-3, wherein the fatty olefin metathesis product is more than 98% Z.

6. The method of any one of embodiments 1-3, wherein the fatty olefin metathesis product is more than 99% Z.

7. The method of any one of embodiments 1-6, wherein the metathesis reaction partser is about 1% to about 50% E.

8. The method of any one of embodiments 2-7, wherein the synthesis of the fatty olefin metathesis product comprises forming the olefin metathesis reaction partner of Formula III by contacting an acylating agent with an alkenol according to Formula II (II)

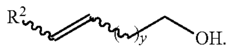

9. The method of embodiment 8, wherein the acylating agent is acetic anhydride.

10. The method of embodiment 8 or embodiment 9, wherein the synthesis of the fatty olefin metathesis reaction partner comprises forming the alkenol of Formula II by reducing an unsaturated fatty carboxyl derivative according to Formula IIa (IIa)

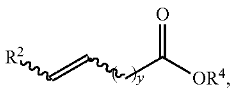

wherein $R^4$ is selected from the group consisting of H and $C_{1-8}$ alkyl.

11. The method of embodiment 10, wherein forming the alkenol of Formula II comprises contacting the unsaturated fatty carboxyl derivative with a base in the presence of a hydrogenation catalyst and hydrogen gas.

12. The method of embodiment 10, wherein forming the alkenol of Formula II comprises contacting the unsaturated fatty carboxyl derivative with a reducing agent.

13. The method of embodiment 12, wherein the reducing agent is sodium bis(2-methoxyethoxy)aluminum hydride.

14. The method or any one of embodiments 8-13, wherein the alkenol of Formula II is about 1% to about 50% E.

15. The method of embodiment 1, wherein:

the fatty olefin metathesis product is an alkenal acetal of Formula VI:

(VI)

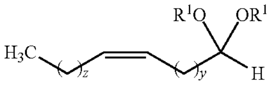

the metathesis reaction partner is a compound of Formula VII:

(VII)

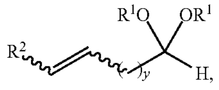

the internal olefin is a compound of Formula IV (IV)

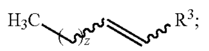

$R^1$ is $C_{1-6}$ alkyl;

$R^2$ is selected from the group consisting of $C_{1-18}$ alkyl and $C_{2-18}$ alkenyl;

$R^3$ is $C_{1-18}$ alkyl;

subscript y an integer ranging from 0 to 17;

subscript z is an integer ranging from 0 to 17; and the group 8 transition metal metathesis catalyst is a Z-selective group 8 transition metal catalyst.

16. The method of embodiment 15, further comprising, converting the metathesis product to an alkenal of Formula VIII:

(VIII)

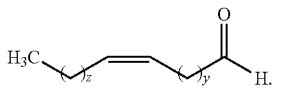

17. The method of any one of embodiments 1-16, wherein the synthesis of the fatty olefin metathesis product comprises forming the internal olefin by contacting a terminal olefin with a metathesis catalyst to form the internal olefin.

18. The method of embodiment 20, wherein the internal olefin is a compound of Formula VIa:

(VIa)

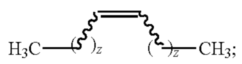

and the terminal olefin is a compound of Formula IVb:

(IVb)

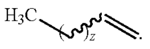

19. The method of embodiment 17 or embodiment 18, wherein the metathesis catalyst for forming the internal olefin is a Z-selective ruthenium catalyst or a Z-selective tungsten catalyst.

20. A method for synthesizing a fatty olefin metathesis product according to Formula I:

(I)

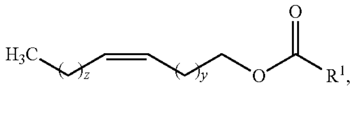

the method comprising contacting an acylating agent with an alkenol according to Formula II (II)

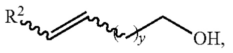

to form an olefin metathesis reaction partner according to Formula III (III)

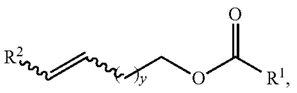

and contacting the olefin metathesis reaction partner with an internal olefin according to Formula IV (IV)

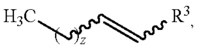

in the presence of a Z-selective ruthenium catalyst or Z-selective osmium catalyst to form the fatty olefin metathesis product; wherein:

$R^1$ is selected from the group consisting of H and $C_{1-6}$ alkyl;

$R^2$ is selected from the group consisting of $C_{1-18}$ alkyl and $C_{2-18}$ alkenyl:

$R^3$ is $C_{1-18}$ alkyl;

subscript y is an integer ranging from 0 to 17;

subscript z is an integer ranging from 0 to 17; and the fatty olefin metathesis product is at least 97% Z.

21. The method of embodiment 20, wherein the acylating agent is acetic anhydride.

22. The method of embodiment 20 or embodiment 21, wherein the alkenol of Formula II is about 1% to about 50% E.

23. A method for synthesizing a fatty olefin metathesis product according to Formula I:

(I)

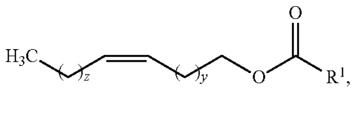

the method comprising reducing an unsaturated fatty carboxyl derivative according to Formula IIa (IIa)

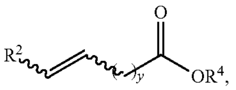

to form an alkenol according to Formula II (II)

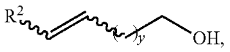

contacting an acylating agent with the alkenol to form an olefin metathesis reaction partner according to Formula III (III)

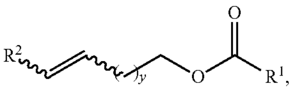

and contacting the olefin metathesis reaction partner with an internal olefin according to Formula IV (IV)

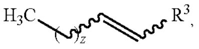

in the presence of a Z-selective ruthenium catalyst a Z-selective osmium catalyst to form the fatty olefin metathesis product; wherein:

$R^1$ is selected from the group consisting of H and $C_{1-6}$ alkyl;

$R^2$ is selected from the group consisting of $C_{1-18}$ alkyl and $C_{2-18}$ alkenyl;

$R^3$ is $C_{1-18}$ alkyl;

$R^4$ is selected from the group consisting H and $C_{1-18}$ alkyl;

subscript y is an integer ranging from 0 to 17;

subscript z is an integer ranging from 0 to 17; and the fatty olefin metathesis product is at least 97% Z.

24. The method of embodiment 23, wherein reducing the unsaturated fatty carboxyl derivative of Formula IIa to form the alkenol of Formula II comprises contacting the unsaturated fatty carboxyl derivative with a base in the presence of a hydrogenation catalyst and hydrogen gas.

25. The method of embodiment 23, wherein reducing the unsaturated fatty carboxyl derivative of Formula IIa to form the alkenol of Formula II comprises contacting the unsaturated fatty carboxyl derivative with a reducing agent.

26. The method of embodiment 25, wherein the reducing agent is sodium bis(2-methoxyethoxy)aluminumhydride.

27. The method of any one if embodiments 23-26, wherein the acylating agent is acetic anhydride.

28. The method of any one of embodiments 23-27, wherein the alkenol of Formula II is about 1% to about 50% E.

29. The method of any one of embodiments 2-28, wherein $R^1$ is $C_{1-3}$ alkyl, $R^2$ is $C_{1-12}$ is alkyl, $R^3$ is $C_{1-12}$ alkyl, y is an integer ranging from 5 to 15, and z is an integer ranging from 0 to 7.

30. The method of an one of embodiments 10, 11, 23 and 24, wherein $R^1$ is $C_{1-3}$ alkyl, is $C_{1-12}$ alkyl, $R^3$ is $C_{1-12}$ alkyl, $R^4$ is $C_{1-3}$ alkyl, y is 7, and z is an integer ranging from 1 to 5.

31. The method of any one of embodiments 10, 12, 23, and 25, wherein $R^1$ is $C_{1-3}$ alkyl, $R^2$ is $C_{1-12}$ alkyl, $R^3$ is $C_{1-12}$ alkyl, $R^4$ is H, y is an integer ranging from 5 to 15, and z is an integer ranging from 1 to 5.

32. The method of any one of embodiments 2-7 wherein:

the metathesis reaction partner according to Formula III is a fatty $C_{12}$-$C_{30}$ olefin acetate;

the internal olefin according to Formula IV is a $C_4$-$C_{20}$ internal olefin; and the fatty olefin metathesis product according to Formula I is a $C_8$-$C_{28}$ (Z)-unsaturated fatty ester acetate.

33. The method of any one of embodiments 2-7 and 32, wherein:

the olefin metathesis reaction partner according to Formula III is (Z)-octadec-9-en-1-yl acetate;

the internal olefin according to Formula IV is (Z)-dec-5-ene; and the fatty olefin metathesis product according to Formula I is (Z)-tetradec-9-en-1-yl acetate.

34. The method of an one embodiments 2-7 and 32, wherein:

the olefin metathesis reaction partner according to Formula III is (Z)-octadec-9-en-1-yl acetate;

the internal olefin according to Formula IV is (Z)-hex-3-ene; and the fatty olefin metathesis product according to Formula I is (Z)-dodec-9-en-1-yl acetate.

35. The method of any one of embodiments 2-7 and 32, wherein:

the olefin metathesis reaction partner according to Formula III is (ZI-icos-11-en-1-yl acetate;

the internal olefin according to Formula IV is (Z)-hex-3-ene; and the fatty olefin metathesis product according to Formula I is (Z)-tetradec-11-en-1-yl acetate.

36. The method of any one of embodiments 8-31, wherein the alkenol according to Formula II is a $C_{10}$-$C_{28}$ fatty alkenol;

the olefin metathesis reaction partner according to Formula III is an acetate ester of the $C_{10}$-$C_{28}$ fatty alkenol;

the internal olefin according to Formula IV is a $C_4$-$C_{20}$ internal olefin; and the fatty olefin metathesis product according to Formula I is a $C_8$-$C_{28}$ (Z)-unsaturated fatty ester acetate.

37. The method of any one of embodiments 10-36, wherein:

the alkenol according to Formula II is (Z)-octadec-9-en-1-ol;

the olefin metathesis reaction partner according to Formula III is (Z)-octadec-9-en-1-yl acetate;

the internal olefin according to Formula IV is (Z)-dec-5-ene; and the fatty olefin metathesis product according to Formula I is (Z)-tetradec-9-en-1-yl acetate.

38. The method of any one of embodiments 10-36, wherein:

the alkenol according to Formula II is (Z)-octadec-9-en-1-ol;

the olefin metathesis reaction partner according to Formula is (Z)-octadec-9-en-1-yl acetate;

the internal olefin according to Formula IV is (Z)-hex-3-ene; and the fatty olefin metathesis product according to Formula I is (Z)-dodec-9-en-1-yl acetate.

39. The method of any one of embodiments 10-36, wherein:

the alkenol according to Formula II (Z)-icos-11-en-1-ol;

the olefin metathesis reaction partner according to Formula III is (Z)-icos-11-en-1-yl acetate;

the internal olefin according to Formula IV is (Z)-hex-3-ene; and the fatty olefin metathesis product according to Formula I is (Z)-tetradec-11-en-1-yl acetate.

40. The method of any one of embodiments 1-38, wherein the synthesis of the fatty olefin metathesis product comprises contacting the olefin metathesis reaction partner with a pretreatment reagent prior to contacting with the internal olefin.

41. The method of embodiment 40, wherein the pretreatment reagent selected from the group consisting of alumina, triethyl aluminum, and magnesium aluminum isopropoxide.

42. The method of any one of embodiments 10-12 and 23-25, wherein the unsaturated fatty carboxyl derivative is derived from a natural oil.

43. The method of embodiment 42, wherein the natural oil is selected from the group consisting of almond oil, canola oil, avocado oil, argan oil, rapeseed oil, coconut oil, corn oil, cottonseed oil, grape seed oil, olive oil, palm oil, peanut oil, hemp oil, macadamia oil, safflower oil, sesame oil, soybean oil, sunflower oil, linseed oil, palm kernel oil, tung oil, jatropha oil, jojoba oil, mustard oil, pennycress oil, camelina oil, castor oil, and combinations thereof.

44. The method of embodiment 42 or embodiment 43, further comprising distilling the unsaturated fatty carboxyl derivative according to Formula IIa, the alkenol according to Formula II, or the olefin metathesis reaction partner of Formula III prior to metathesis to remove a plant-based impurity.

45. The method of embodiment 44, wherein the plant-based impurity comprises one or more proteins.

46. The method of any one of embodiments 2 to 45, wherein the Z-selective metathesis catalyst has a structure according to Formula V:

(V)

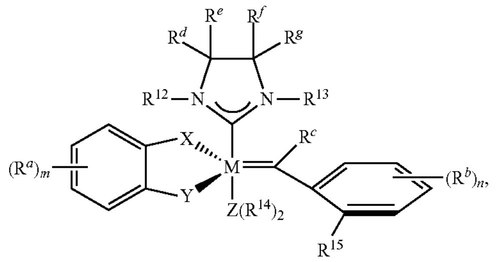

wherein:

M is selected from the group consisting of ruthenium and osmium;

X and Y are independently selected front the group consisting of S and O;

Z is selected from the group consisting of O, S(=O), N, and halogen;

each subscript m and subscript n is an integer independently selected from 0, 1, 2, 3, and 4;

each $R^a$ is independently selected from the group consisting of halogen, $C_1$-$C_6$ alkyl alkoxy, aryl, and heteroaryl; or one $R^a$ is taken together with an adjacent $R^a$ to form an unsubstituted or substituted bicyclic ring, or an unsubstituted or substituted polycyclic ring;

each $R^b$ is independently selected from the group consisting of halogen, $C_1$-$C_6$ alkyl, alkoxy, aryl, and heteroaryl; or one $R^b$ is taken together with an adjacent $R^b$ to form an unsubstituted or substituted bicyclic ring, or an unsubstituted or substituted polycyclic ring;

$R^c$ is selected from the group consisting of hydrogen and $C_1$-$C_6$ alkyl;

each $R^d$, $R^e$, $R^f$, and $R^g$ is independently selected from the group consisting of hydrogen and $C_1$-$C_6$ alkyl;

$R^{12}$ and $R^{13}$ are independently selected from the group consisting of 2,4,6-tri-iso-propylphenyl, 2,6-di-iso-propylphenyl, 2,6-di-adamantylphenyl, 2-iso-propyl-6-tert-butylphenyl, 2,4,6-tri-tert-butylphenyl, and 2,6-di-tert-butylphenyl;

each $R^{14}$ is independently selected from the group consisting of hydrogen, methyl, ethyl, n-propyl, iso-propyl, n-butyl, tert-butyl, cyclohexyl, benzyl, and phenyl; and $R^{15}$ is selected from the group consisting of hydrogen, halogen, and $C_1$-$C_6$ alkyl, or $R^{15}$ and one $R^{14}$ are taken together to form a bond.

47. The method of embodiment 46, wherein:

M is ruthenium;

X and Y are S;

Z is selected from the group consisting of O and S(=O);

subscript m is 2;

subscript n is 0;

each $R^a$ is independently selected from the group consisting of halogen, $C_1$-$C_6$ alkyl, and aryl;

$R^c$ is hydrogen;

each $R^d$, $R^e$, $R^f$, and $R^g$ is hydrogen; and each $R^{14}$ is independently selected from the group consisting of methyl, iso-propyl benzyl, and tert-butyl.

48. The method of embodiment 46 or 47, wherein the metathesis catalyst is selected from the group consisting of:

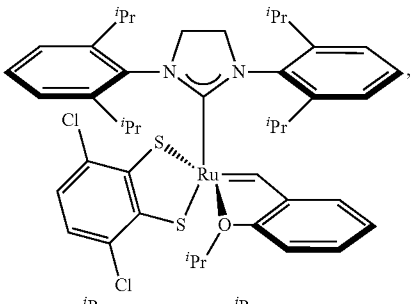

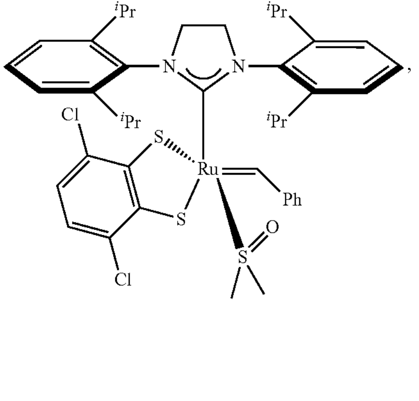

and

-continued

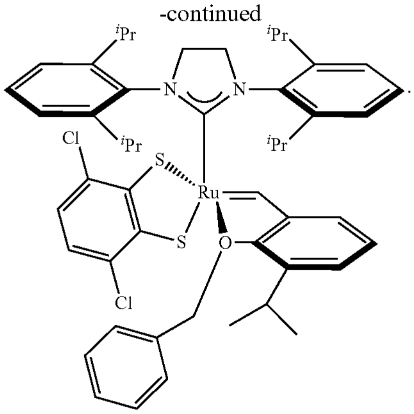

Although the foregoing has been described in some detail by way of illustration and example for purposes of clarity and understanding, one of skill in the art will appreciate that certain changes and modifications can be practiced within the scope of the appended claims. All publications, patents, patent applications, and sequence accession numbers cited herein are hereby incorporated by reference in their entirety for all purposes.

What is claimed is:

1. A method for synthesizing a Z-enriched fatty olefin metathesis product, the method comprising contacting an olefin metathesis reaction partner with an internal olefin in the presence of a Z-selective group 8 transition metal metathesis catalyst to form the Z-enriched fatty olefin metathesis product, wherein:

the olefin metathesis reaction partner comprises a mixture of Z olefins and E olefins in a starting Z:E ratio, the fatty olefin metathesis product comprises a mixture of Z olefins and E olefins in a product Z:E ratio, and the product Z:E ratio is higher than the starting Z:E ratio, wherein:

the fatty olefin metathesis product is an acylated alkenol of Formula I:

(I)

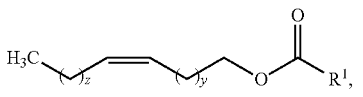

the metathesis reaction partner is a compound of Formula III (III)

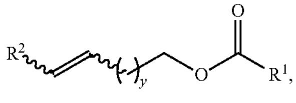

the internal olefin is a compound of Formula IV (IV)

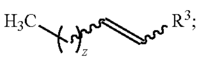

$R^1$ is selected from the group consisting of H and $C_{1-6}$ alkyl;

$R^2$ is selected from the group consisting of $C_{1-18}$ alkyl and $C_{2-18}$ alkenyl;

$R^3$ is $C_{1-18}$ alkyl;

subscript y is an integer ranging from 0 to 17;

subscript z is an integer ranging from 0 to 17; and the Z-selective metathesis catalyst has a structure according to Formula V:

(V)

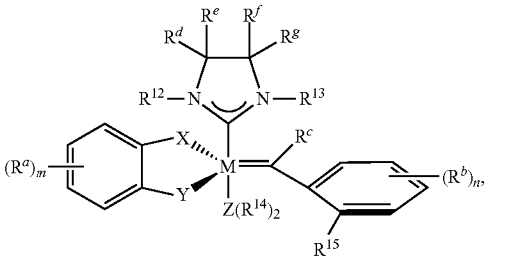

wherein:

M is selected from the group consisting of ruthenium and osmium;

X and Y are independently selected from the group consisting of S and O;

Z is selected from the group consisting of S(═O), O, N, and halogen;

subscript m is an integer selected from 2, 4, 3, 1, and 0;

subscript n is an integer selected from 0, 1, 2, 3, or 4;

each $R^a$ is independently selected from the group consisting of halogen, $C_1$-$C_6$ alkyl, alkoxy, aryl, and heteroaryl; or one $R^a$ is taken together with an adjacent $R^a$ to form an unsubstituted or substituted bicyclic ring, or an unsubstituted or substituted polycyclic ring;

each $R^b$ is independently selected from the group consisting of halogen, $C_1$-$C_6$ alkyl, alkoxy, aryl, and heteroaryl; or one $R^b$ is taken together with an adjacent $R^b$ to form an unsubstituted or substituted bicyclic ring, or an unsubstituted or substituted polycyclic ring;

$R^c$ is selected from the group consisting of hydrogen and $C_1$-$C_6$ alkyl;

each $R^d$, $R^e$, $R^f$ and $R^g$ is independently selected from the group consisting of hydrogen and $C_1$-$C_6$ alkyl;

$R^{12}$ and $R^{13}$ are independently selected from the group consisting of 2,6-di-iso-propylphenyl, 2,4,6-tri-iso-propylphenyl, 2,6-di-adamantylphenyl, 2-iso-propyl-6-tert-butylphenyl, 2,4,6-tri-tert-butylphenyl, and 2,6-di-tert-butylphenyl;

each $R^{14}$ is independently selected from the group consisting of methyl, ethyl, n-propyl, iso-propyl, n-butyl, tert-butyl, cyclohexyl, benzyl, phenyl, and hydrogen; and $R^{15}$ is selected from the group consisting of hydrogen, halogen, and $C_1$-$C_6$ alkyl or $R^{15}$ and one $R^{14}$ are taken together to form a bond, wherein the fatty olefin metathesis product is present in an amount of at least 97% Z.

2. The method of claim 1, wherein the fatty olefin metathesis product is more than 99% Z.

3. The method of claim 1, wherein the metathesis reaction partner is about 1% to about 50% E.

4. The method of claim 1, wherein:

M is ruthenium;

X and Y are S;

Z is selected from the group consisting of S(═O) and O;

subscript m is 2;

subscript n is 0;

each $R^a$ is independently selected from the group consisting of halogen, $C_1$-$C_6$ alkyl, and aryl;

$R^c$ is hydrogen;

each $R^d$, $R^e$, $R^f$, and $R^g$ is hydrogen; and each $R^{14}$ is independently selected from the group consisting of methyl, iso-propyl, benzyl, and tert-butyl.

5. The method of claim 4, wherein the metathesis catalyst is selected from the group consisting of:

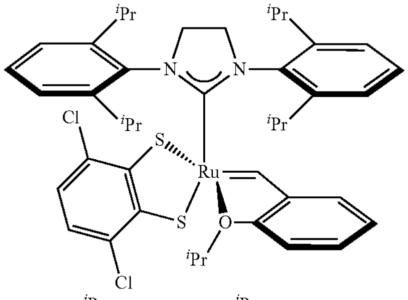

,

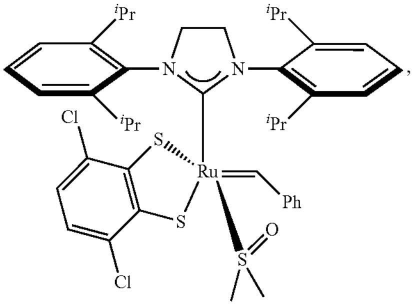

, and

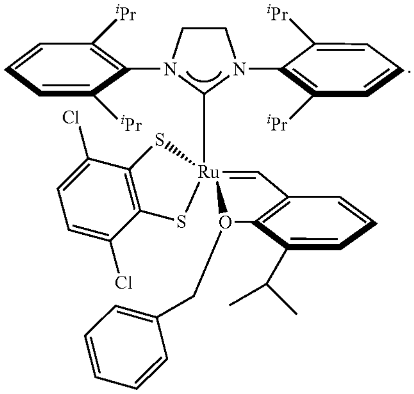

.

6. The method of claim 1, wherein the synthesis of the fatty olefin metathesis product comprises forming the olefin metathesis reaction partner of Formula III by contacting an acylating agent with an alkenol according to Formula II (II)

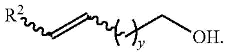

7. The method of claim 6, wherein the acylating agent is acetic anhydride.

8. The method of claim 6, wherein the synthesis of the fatty olefin metathesis reaction partner comprises forming the alkenol of Formula II by reducing an unsaturated fatty carboxyl derivative according to Formula IIa (IIa)

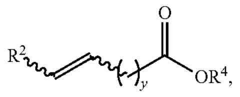

wherein $R^4$ is selected from the group consisting of H and $C_{1-8}$ alkyl.

9. The method of claim 8, wherein forming the alkenol of Formula II comprises contacting the unsaturated fatty carboxyl derivative with a base in the presence of a hydrogenation catalyst and hydrogen gas.

10. The method of claim 8, wherein forming the alkenol of Formula II comprises contacting the unsaturated fatty carboxyl derivative with a reducing agent.

11. The method of claim 10, wherein the reducing agent is sodium bis(2-methoxyethoxy)aluminum hydride.

12. The method of claim 8, wherein the unsaturated fatty carboxyl derivative is derived from a natural oil.

13. The method of claim 12, wherein the natural oil is selected from the group consisting of almond oil, canola oil, avocado oil, argan oil, rapeseed oil, coconut oil, corn oil, cottonseed oil, grape seed oil, olive oil, palm oil, peanut oil, hemp oil, macadamia oil, safflower oil, sesame oil, soybean oil, sunflower oil, linseed oil, palm kernel oil, tung oil, jatropha oil, jojoba oil, mustard oil, pennycress oil, camelina oil, castor oil, and combinations thereof.

14. The method of claim 12, further comprising distilling the unsaturated fatty carboxyl derivative prior, the alkenol, or the olefin metathesis reaction partner prior to metathesis to remove a plant-based impurity.

15. The method of claim 1, wherein the synthesis of the fatty olefin metathesis product comprises forming the internal olefin by contacting a terminal olefin with a metathesis catalyst to form the internal olefin.

16. The method of claim 15, wherein the internal olefin is a compound of Formula VIa:

(VIa)

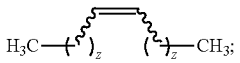

and the terminal olefin is a compound of Formula IVb:

(IVb)

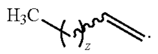

17. The method of claim 15, wherein the metathesis catalyst for forming the internal olefin is a Z-selective ruthenium catalyst or a Z-selective tungsten catalyst.

18. The method of claim 1, wherein $R^1$ is $C_{1-3}$ alkyl, $R^2$ is $C_{1-12}$ alkyl, $R^3$ is $C_{1-12}$ alkyl, y is an integer ranging from 5 to 15, and z is an integer ranging from 0 to 7.

19. The method of claim 1, wherein:

the metathesis reaction partner according to Formula III is a fatty $C_{12}$-$C_{30}$ olefin acetate;

the internal olefin according to Formula IV is a $C_4$-$C_{20}$ internal olefin; and the fatty olefin metathesis product according to Formula I is a $C_8$-$C_{28}$ (Z)-unsaturated fatty ester acetate.

20. The method of claim 1, wherein:

the olefin metathesis reaction partner according to Formula III is (Z)-octadec-9-en-1-yl acetate;

the internal olefin according to Formula IV is (Z)-dec-5-ene; and the fatty olefin metathesis product according to Formula I is (Z)-tetradec-9-en-1-yl acetate.

21. The method of claim 1, wherein:

the olefin metathesis reaction partner according to Formula III is (Z)-octadec-9-en-1-yl acetate;

the internal olefin according to Formula IV is (Z)-hex-3-ene; and the fatty olefin metathesis product according to Formula I is (Z)-dodec-9-en-1-yl acetate.

22. The method of claim 1, wherein:

the olefin metathesis reaction partner according to Formula III is (Z)-icos-11-en-1-yl acetate;

the internal olefin according to Formula IV is (Z)-hex-3-ene; and the fatty olefin metathesis product according to Formula I is (Z)-tetradec-11-en-1-yl acetate.

23. The method of claim 1, wherein the synthesis of the fatty olefin metathesis product comprises contacting the olefin metathesis reaction partner with a pretreatment reagent prior to contacting with the internal olefin.

24. The method of claim 23, wherein the pretreatment reagent is selected from the group consisting of alumina, triethyl aluminum, and magnesium aluminum isopropoxide.

* * * * *